(12) United States Patent
Ittah et al.

(10) Patent No.: US 10,981,959 B2
(45) Date of Patent: *Apr. 20, 2021

(54) COMPOSITIONS AND METHODS FOR FABRICATING SYNTHETIC DRAGLINE SPIDER SILK

(71) Applicant: SEEVIX MATERIAL SCIENCES LTD., Jerusalem (IL)

(72) Inventors: Shmulik Ittah, Mevaseret Zion (IL); Meni Shimel, Kiryat Ono (IL); Uri Gat, Beit Hakerem (IL)

(73) Assignee: SEEVIX MATERIAL SCIENCES LTD., Jerusalem (IL)

( * ) Notice: Subject to any disclaimer, the term of this patent is extended or adjusted under 35 U.S.C. 154(b) by 34 days.

This patent is subject to a terminal disclaimer.

(21) Appl. No.: 15/751,375

(22) PCT Filed: Aug. 10, 2016

(86) PCT No.: PCT/IL2016/050874
§ 371 (c)(1),
(2) Date: Feb. 8, 2018

(87) PCT Pub. No.: WO2017/025964
PCT Pub. Date: Feb. 16, 2017

(65) Prior Publication Data
US 2019/0002510 A1  Jan. 3, 2019

Related U.S. Application Data

(60) Provisional application No. 62/317,572, filed on Apr. 3, 2016, provisional application No. 62/293,880, filed on Feb. 11, 2016, provisional application No. 62/203,102, filed on Aug. 10, 2015.

(51) Int. Cl.
*C07K 14/435* (2006.01)
*C12N 15/86* (2006.01)
*C12N 15/866* (2006.01)

(52) U.S. Cl.
CPC ........ *C07K 14/43518* (2013.01); *C12N 15/86* (2013.01); *C12N 15/866* (2013.01); *C07K 2319/21* (2013.01); *C12N 2710/14043* (2013.01)

(58) Field of Classification Search
CPC .......... C07K 14/43518; C07K 2319/21; C12N 15/86; C12N 15/866; C12N 2710/14043
See application file for complete search history.

(56) References Cited

U.S. PATENT DOCUMENTS

| | | | | |
|---|---|---|---|---|
| 7,057,023 B2 * | 6/2006 | Islam | ........................ | D01F 4/00 530/350 |
| 8,030,024 B2 | 10/2011 | Scheibel et al. | | |
| 8,461,301 B2 | 6/2013 | Gat et al. | | |
| 2005/0054830 A1 * | 3/2005 | Islam | ............... | C07K 14/43513 530/353 |
| 2007/0196429 A1 | 8/2007 | Scheibel et al. | | |
| 2012/0022005 A1 | 1/2012 | Gat et al. | | |
| 2016/0298265 A1 | 10/2016 | Lewis et al. | | |
| 2019/0002510 A1 | 1/2019 | Ittah et al. | | |

FOREIGN PATENT DOCUMENTS

| | | | |
|---|---|---|---|
| CN | 101018806 B | 8/2007 | |
| CN | 101133080 A | 2/2008 | |
| CN | 101253193 B | 8/2008 | |
| CN | 101395178 A | 3/2009 | |
| EP | 1609801 A1 | 12/2005 | |
| JP | 2008507260 A | 3/2008 | |
| WO | 2006002827 | 1/2006 | |
| WO | 2006002853 A1 | 1/2006 | |
| WO | WO-2011063990 A2 * | 6/2011 | ................ A61P 3/02 |
| WO | 2014037453 A1 | 3/2014 | |
| WO | 2017025964 | 2/2017 | |

OTHER PUBLICATIONS https://www.bioinformatics.org/sms/prot_mw.html, The Sequence Manipulation Suite: Protein Molecular Weight, accessed on Dec. 2, 2019.*
Bo An et al.,"Physical and biological regulation of neuron regenerative growth and network formation on recombinant dragline silks", Elsevier, Biomaterials 48, Apr. 2015, pp. 137-146.
Ittah, S., et al.; "A Proposed Model for Dragline Spider Silk Self-Assembly: Insights from the Effect of the Repetitive Domain Size on Fiber Properties"; Biopolymers; Issue 93, vol. 5, pp. 458-468, 2010.
Ittah, S., et al.; "A Model for the Structure of the C-Terminal Domain of Dragline Spider Silk and the Role of Its Conserved Cysteine"; Biomacromolecules; Issue 8, vol. 9, pp. 2768-2773, 2007.
Ittah, S., et al..; "An Essential Role for the C-Terminal Domain of a Dragline Spider Silk Protein in Directing Fiber Formation"; Biomacromolecules; Issue 7, vol. 6, pp. 1790-1795, 2006.
Huemmerich, D., et al..; "Novel Assembly Properties of Recombinant Spider Dragline Silk Proteins"; Current Biology; vol. 14, pp. 2070-2074, 2004.
Gatesy, J., et al.; "Extreme Diversity, Conservation, and Convergence of Spider Silk Fibroin Sequences"; Science; vol. 291 (5513), pp. 2603-2605, 2001.
Rising, et al; "Spider silk proteins: recent advances in recombinant production, structure-function relationships and biomedical applications"; Cellular and Molecular Life Sciences vol. 68, pp. 169-184, 2010.
Lewicka, et al; "Recombinant spider silk matrices for neural stem cell cultures", Biomaterials, vol. 33, No. 31, pp. 7712-7717, Aug. 3, 2012.
Knight, et al; "Advances in 3D cell culture technologies enabling tissue-like structures to be created in vitro", Journal of Anatomy, vol. 227, No. 6, pp. 746-756. Nov. 20, 2014.
Final Office Action (translated) for Japanese Patent Application No. 2018-527035, 8 pp., dated Jun. 30, 2020.

* cited by examiner

*Primary Examiner* — James H Alstrum-Acevedo
*Assistant Examiner* — Erinne R Dabkowski
(74) *Attorney, Agent, or Firm* — The Roy Gross Law Firm, LLC; Roy Gross

(57) ABSTRACT

Compositions comprising a mixture of proteins derived from MaSP, nucleic acids encoding same and method for the preparation of synthetic dragline spider silk are provided. The compositions of the invention comprise a mixture of proteins of differing molecular weight, wherein each protein of said mixture comprises, independently, multiple repeats of a repetitive region of a MaSP (major ampullate spidroin) protein or a functional homolog, variant, derivative or fragment thereof.

12 Claims, 7 Drawing Sheets

Specification includes a Sequence Listing.

Lower focus field | Middle focus field | Upper focus field
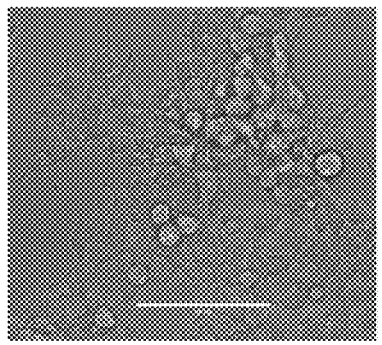 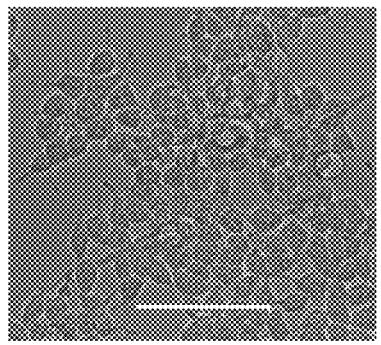 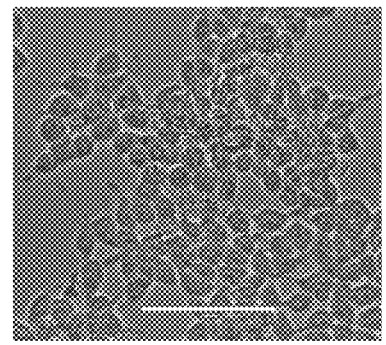
Fig. 5A          Fig. 5B          Fig. 5C
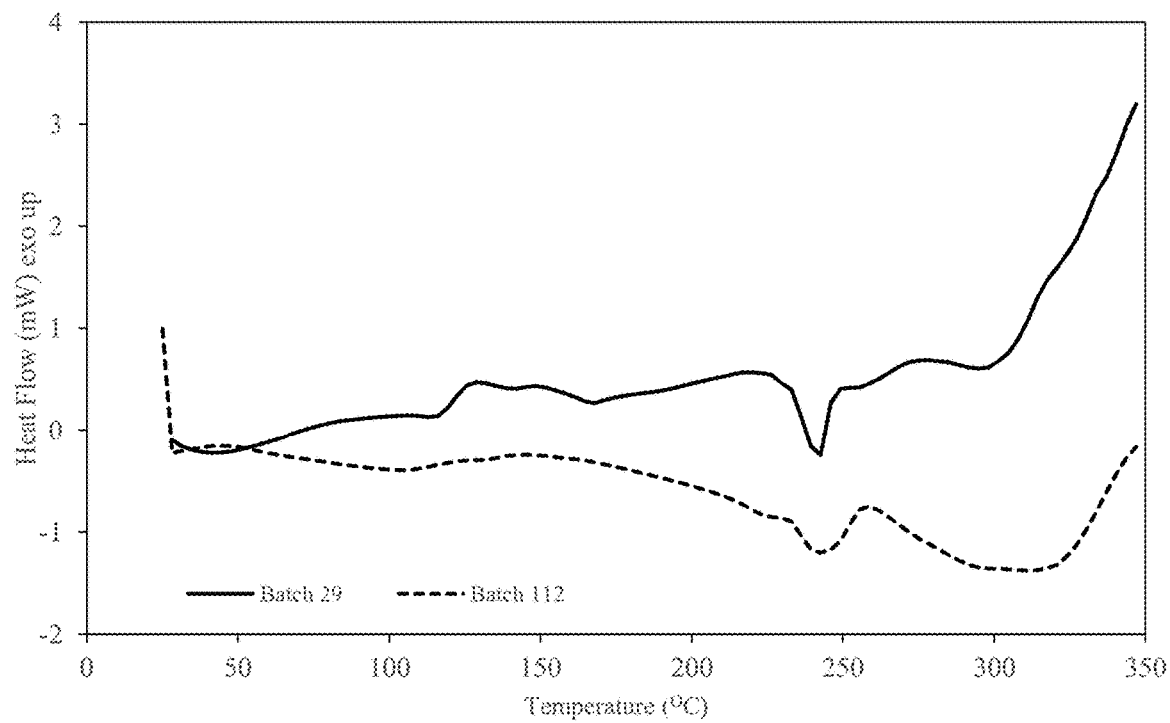
Fig. 6

COMPOSITIONS AND METHODS FOR FABRICATING SYNTHETIC DRAGLINE SPIDER SILK

RELATED APPLICATIONS

This application is a National Phase of PCT Patent Application No. PCT/IL2016/050874 having International filing date of Aug. 10, 2016 entitled COMPOSITIONS AND METHODS FOR FABRICATING SYNTHETIC DRAGLINE SPIDER SILK, which claims the benefit of priority of U.S. Patent Application Nos. 62/203,102 filed on Aug. 10, 2015, 62/293,880 filed on Feb. 11, 2016 and 62/317,572 filed on Apr. 3, 2016. The contents of the above applications are all incorporated by reference as if fully set forth herein in their entirety.

FIELD OF INVENTION

The present invention is directed to compositions comprising a mixture of proteins derived from a MaSP (major ampullate spidroin) protein, for the preparation of synthetic dragline spider silk.

BACKGROUND OF THE INVENTION

Dragline spider silk is known in the art as the silk used by the orb-web weaving spiders to construct the frame and radii of their webs as well a life line when they fall or escape danger. To be able to perform these tasks, the dragline fiber displays a remarkably high toughness due to combination of high elasticity and strength, which places it as the toughest fiber, whether natural or man-made. For instance, dragline is six times as strong as high-tensile steel in its diameter and three times tougher than Kevlar that is one of the strongest synthetic fibers ever made.

Dragline silk consists of two main polypeptides, mostly referred to as major ampullate spidroin (MaSp) 1 and 2, and also to ADF-3 and ADF-4 in *Araneus diadematus*. These proteins have apparent molecular masses in the range of 200-720 kDa, depending on sample age and conditions of analysis. The known dragline silk spidroins are composed of highly iterated blocks of alternating alanine-rich segments, forming crystalline β-sheets in the fiber, and glycine-rich segments which are more flexible and mainly lack ordered structure. The C-terminal region is non-repetitive, highly conserved between species, and adopts α-helical conformation. The N-terminal region of dragline silk proteins was also found to be highly conserved between different spidroins, and also between different spider species.

Numerous attempts have been made to synthetically create spider silk, such as through genetic engineering using bacteria, yeast, plants and mammalian cells in tissue culture and even transgenic goats.

U.S. Pat. No. 8,461,301 relates to, inter alia, isolated amino acid sequence comprising multiple repeats of a semi-synthetic spider silk protein domain, or any functional homolog, variant, derivative, fragment or mutant thereof. This publication is incorporated herein by reference in its entirety.

Additional publications relating to dragline spider silk include, but are not limited to, Ittah, S., et al. Biopolymers, 93 (5), 458-468, 2010; Ittah, S., et al. Biomacromolecules, 8 (9), 2768-2773, 2007; Ittah, S., et al., Biomacromolecules, 7 (6), 1790-1795, 2006; and Huemmerich, D., Ittah, S., et al., Current Biology, 14, 2070-2074, 2004. These publications are incorporated herein by reference in their entirety.

There is an unmet need for improved compositions and methods for producing fibers with mechanical properties similar to the natural spider silk.

SUMMARY OF THE INVENTION

The present invention is directed to compositions comprising a mixture of proteins having differing molecular weight and derived from a MaSP protein, such as for the fabrication of synthetic dragline spider silk.

According to some aspects, there is provided a composition comprising a mixture of proteins comprising m types of proteins of differing molecular weight, wherein each protein in said mixture comprises, independently, n repeats of a repetitive region derived from a MaSP protein, or a functional homolog, variant, derivative or fragment thereof, wherein m and n are, independently, an integer between 2 to 70.

In some embodiments, said MaSP protein is a protein selected from the group consisting of: MaSP-1, MaSP-2, ADF-4 and ADF-3. In some embodiments, said MaSP protein is a protein selected from MaSP-1 and ADF-4.

In some embodiments, said n is identical for each type of protein in said mixture. In another embodiment, n is an integer equal to or between 4 and 32. In another embodiment, m is an integer equal to or between 4 and 32. In another embodiment, the ratio of 'n' to 'm' is in the range of 2:1-1:2. In another embodiment, 'n' and 'm' are equal.

In another embodiment, each repeat has a molecular weight in the range of 2 kDa to 3.5 kDa. In another embodiment, each repeat has a molecular weight in the range of 2.6 kDa to 3 kDa.

In another embodiment, the composition comprises two or more proteins of said mixture having molecular weight increment of 2 kDa to 3.5 kDa. In another embodiment, the composition comprises two or more proteins of said mixture having molecular weight increment of 2.6 kDa to 3 kDa.

In some embodiments, said repeats are of a homolog, variant, derivative of a repetitive region of a MaSP protein or fragment thereof. In some embodiments, said repeats are of a homolog, variant, derivative of a repetitive region of a MaSP1 protein or fragment thereof. In some embodiments, said repeats are of a homolog, variant, derivative of a repetitive region of an ADF-4 protein or fragment thereof.

In some embodiments, said repetitive region has a first moiety and contiguous thereto a second moiety, the first moiety is an amino acid sequence of 5-30 amino acids comprising at least 50% alanine residues, the second moiety is an amino acid sequence of 20-60 amino acids comprising at least 80% residues selected from the group consisting of glycine, serine, proline and tyrosine.

In some embodiments, the second moiety of said repetitive region comprises at-most two glutamine residues.

In some embodiments, said repetitive region has the amino acid sequence as set forth in SEQ ID NO: 1

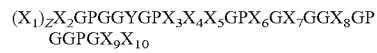

wherein $X_1$ is, independently, at each instance A or G wherein at least 50% of $(X_1)_Z$ is A, Z is an integer between 5 to 30; $X_2$ is S or G; $X_3$ is G or E; $X_4$ is G, S or N; $X_5$ is Q or Y; $X_6$ is G or S; $X_7$ is P or R; $X_8$ is Y or Q; $X_9$ is G or S; and $X_{10}$ is S or G.

In some embodiments, said repetitive region comprises the amino acid sequence as set forth in SEQ ID NO: 33:

wherein $X_1$ is, independently, at each instance A or G wherein at least 50% of $(X_1)_Z$ is A, Z is an integer between 5 to 30; $X_2$ is S-G, or absent; $X_3$ is G-Q or absent; $X_4$ is G or absent; $X_5$ is S or G; $X_6$ is S-P, G-R or absent.

In another embodiment, said repetitive region comprises the amino acid sequence as set forth in SEQ ID NO: 34 (PGGYGP).

In another embodiment, said repetitive region has the amino acid sequence as set forth in anyone of SEQ ID NO: 2-4. In another embodiment, said homolog shares at least 70% homology with any one of SEQ ID NO: 1-3.

In another embodiment, said repetitive region has the amino acid sequence as set forth in anyone of SEQ ID NO: 2-4 and 35-44. In another embodiment, said homolog shares at least 70% homology with any one of SEQ ID NO: 1-3, 33, and 35-44.

In another embodiment, said repetitive region comprises the amino acid sequence as set forth in SEQ ID NO: 2 (SGPGGYGPGSQGPSGPGGYGPGGPGSS). In another embodiment, said repetitive region comprises the amino acid sequence as set forth in SEQ ID NO: 3 (AAAAAAAASGPGGYGPGSQGPSGPG-GYGPGGPGSS). In another embodiment, said repetitive region comprises the amino acid sequence as set forth in SEQ ID NO: 35 (SGPGGYGPGSQGPSGPG-GYGPGGPGSSAGAGAGAAA). In another embodiment, said repetitive region comprises the amino acid sequence as set forth in SEQ ID NO: 36 (SGPGGYGPGSQGPSGPG-GYGPGGPGSSAGAGAGA). In another embodiment, said repetitive region comprises a ratio of 1:2-1:16, 1:2-1:8 or 1:4 between SEQ ID NO: 35 (SGPG-GYGPGSQGPSGPGGYGPGGPGSSAGAGAGAAA) and SEQ ID NO: 36 (SGPGGYGPGSQGPSGPG-GYGPGGPGSSAGAGAGA).

In another embodiment, said repetitive region comprises the amino acid sequence as set forth in SEQ ID NO: 37 (SGSGPGGYGPGGQGPGGYGPGGQGPYGPG). In another embodiment, said repetitive region comprises the amino acid sequence as set forth in SEQ ID NO: 38 (SGSGPGGYGPGGQGPGGYGPGGQGPYGP-GAAAAAAA). In another embodiment, said repetitive region comprises the amino acid sequence as set forth in SEQ ID NO: 39 (GGSGPGGYGPGGQGPG-GYGPGGQGPYGPG). In another embodiment, said repetitive region comprises the amino acid sequence as set forth in SEQ ID NO: 40 (GGSGPGGYGPGGQGPG-GYGPGGQGPYGPGAAAAAAA). In another embodiment, said repetitive region comprises a ratio of 1:2-1:16, 1:2-1:8 or 1:4 between SEQ ID NO: 38 (SGSGPG-GYGPGGQGPGGYGPGGQGPYGPGAAAAAAA) and SEQ ID NO: 40 (GGSGPGGYGPGGQGPG-GYGPGGQGPYGPGAAAAAAA).

In another embodiment, said repetitive region comprises the amino acid sequence as set forth in SEQ ID NO: 41 (SGPGQGGYGGPGGQGPGRGGYGPGAGS). In another embodiment, said repetitive region comprises the amino acid sequence as set forth in SEQ ID NO: 42 (SGPGQG-GYGGPGGQGPGRGGYGPGAGSAAAAAAAA). In another embodiment, said repetitive region comprises the amino acid sequence as set forth in SEQ ID NO: 43 (GGPGQGGYGGPGGQGPGRGGYGPGAGS). In another embodiment, said repetitive region comprises the amino acid sequence as set forth in SEQ ID NO: 44 (GGPGQG-GYGGPGGQGPGRGGYGPGAGSAAAAAAAA). In another embodiment, said repetitive region comprises a ratio of 1:2-1:16, 1:2-1:8 or 1:4 between SEQ ID NO: 42 (SGPGQGGYGGPGGQGPGRGGYGP-GAGSAAAAAAAA) and SEQ ID NO: 44 (GGPGQG-GYGGPGGQGPGRGGYGPGAGSAAAAAAAA).

In another embodiment, said repetitive region comprises the amino acid sequence as set forth in SEQ ID NO: 4 (AAAAAAAASGPGGYGPENQGPSGPG-GYGPGGPGSS).

In another embodiment, each protein of said mixture further comprises a single N-terminal region selected from the group consisting of: SEQ ID NO: 5 (MSYYHHHHHHDYDIPTTENLYFQGAMDPE-FKGLRRRAQLV); SEQ ID NO: 6 (MSYYHHHHHHDY-DIPTTENLYFQGAMDPEFKGLRRRAQLVRPL-SNLDNA); SEQ ID NO: 7 (MSYYHHHHHHDYDIPTTENLYFQGAMDPE-FKGLRRRAQLVDPPGCRNSARAGSS), or any functional homolog, variant, derivative, or fragment thereof. In another embodiment, said homolog of said N-terminal region shares at least 70% homology with any one of SEQ ID NOs: 5-7.

In another embodiment, each protein of said mixture further comprises a single C-terminal region having the amino acid sequence as set forth in SEQ ID NO: 9 (GPSGP-GAYGPSPSASASVAASRLSSPAASSRVS-SAVSSLVSSGPTNGAAVSGALNSLVS QISASNPGLSGCDALVQALLELVSALVAILSSAS-IGQVNVSSVSQSTQMISQALS), or any functional homolog, variant, derivative, fragment or mutant thereof. In another embodiment, said homolog of said C-terminal region shares at least 70% homology with SEQ ID NO: 9.

In some embodiments, one or more proteins of said mixture further comprises at least one tag sequence.

In some embodiments, said mixture of proteins further comprises ADF-3 or MASP-2 proteins, or a functional homolog, variant, derivative or fragment thereof. In some embodiments, said ADF-3 or MASP-2 proteins constitute about 1-50% of the molecular weight said mixture of proteins, or any integer there between. In one embodiment, said ADF-3 protein has the GenBank Accession No. AAC47010.1.

In some embodiments, the composition further comprises a carrier, diluent or excipient.

According to some aspects, the invention provides an isolated nucleic acid sequence encoding two or more proteins of said the mixture of proteins of the present invention. According to some aspects, the invention provides an expression vector comprising the nucleic acid sequence of the present invention, wherein said nucleic acid sequence is under expression control of an operably linked promoter and, optionally, regulatory sequences. According to some aspects, the invention provides host cell transformed with the expression vector of the present invention.

According to some aspects, the invention provides a fiber comprising the composition of the invention. According to some aspects, the invention provides an article comprising the composition and/or the fiber of the invention.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 5A-C show multi-layered HEK293 cell growth on the fibers of the invention.

FIG. 6 shows a DSC curve depicting the fingerprint of the fiber of the invention.

DETAILED DESCRIPTION OF THE INVENTION

Figure 1A:
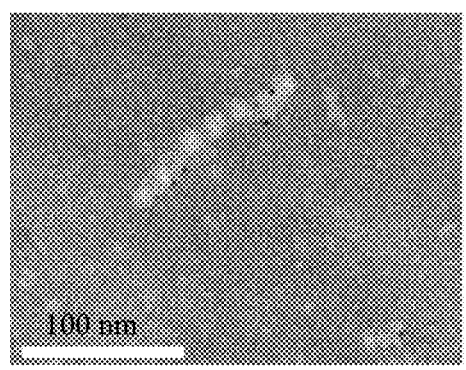
FIGS. 1A-I depict the nano-fibers of the invention, using IMMUNO-TEM (transmission electron microscopy) characterization (FIGS. 1A-C), light microscopy of the assembled fibers using three varying constructs: C1, C2 and C3 (FIGS. 1D-F, respectively) and confocal microscopy (FIGS. 1G-I).
Figure 1B:
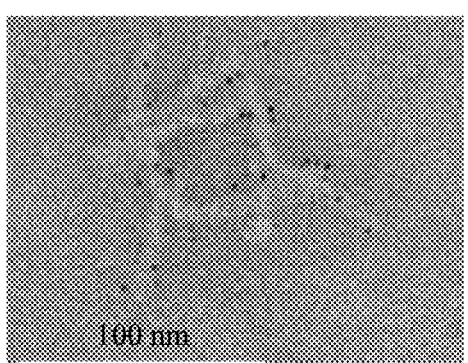

The present invention provides, in some embodiments, compositions comprising a mixture of proteins having a differing molecular weight, nucleic acid sequences encoding same, expression vectors and cells, useful for the preparation of synthetic dragline spider silk. The invention further provides articles and fibers comprising said compositions.

The present invention is based in part on the unexpected finding that artificial dragline spider silk, synthesized using a mixture of proteins of differing molecular weight and derived from a MaSP protein, has exceptional mechanical properties similar and in some properties preferable to the natural dragline spider silk.

As demonstrated hereinbelow, the artificial dragline spider silk of the invention showed unexpected thermal properties (see, FIG. 6). Specifically, the fiber of the invention showed a DSC peak at about 265° C. to 320±5° C., indicating beneficial thermal properties relative to native dragline spider silk.

According to some aspects, there is provided a composition comprising a mixture of proteins comprising m types of proteins of differing molecular weight, wherein each protein in said mixture comprises, independently, n repeats of a repetitive region of a MaSP protein or a functional homolog, variant, derivative or fragment thereof, wherein m and n are, independently, an integer between 2 to 70.

As used herein, the term "mixture of proteins" or "protein mixture" refers to a plurality of proteins, such as at least 2, at least 3, at least 4, at least 5, at least 6, at least 7, at least 8, at least 9 or at least 10 types of proteins, wherein each type of protein has a relatively unique and uniform molecular weight. As used herein, the term "unique" refers to the molecular weight of each type of protein in said protein mixture being distinct from other types of proteins in said mixture. As used herein, the term "uniform" refers to the molecular weight of each type of protein in said protein mixture being at least 95% identical to with the same types of proteins in said mixture. As used herein, the term "relatively" refers to a variation of not more than one amino acid residue within each type of protein.

The terms "major ampullate spidroin protein" and "spidroin protein" are used interchangeably throughout the description and encompass all known major ampullate spidroin proteins, typically abbreviated "MaSP", or "ADF" in the case of *Araneus diadematus*. These major ampullate spidroin proteins are generally of two types, 1 and 2. These terms furthermore include non-natural proteins, as disclosed herein, with a high degree of identity and/or similarity to at least the repetitive region of the known major ampullate spidroin proteins. Additional suitable spider silk proteins include MaSP2, MiSP, MiSp2, AcSP, FLYS, FLAS, and piriform.

As used herein, the term "repetitive region", "repetitive sequence" or "repeat" refer to a recombinant protein sequence derived from repeat units which naturally occur multiple times in spider silk amino acid sequences (e.g., in the MaSP-1 peptide). One skilled in the art will appreciate that the primary structure of the spider silk proteins is considered to consist mostly of a series of small variations of a unit repeat. The unit repeats in the naturally occurring proteins are often distinct from each other. That is, there is little or no exact duplication of the unit repeats along the length of the protein.

In some embodiments, the synthetic spider silks of the invention are made wherein the primary structure of the protein comprises a number of exact repetitions of a single unit repeat or a direct repeat. The term "direct repeat" as used herein is a repeat in tandem (head-to-tail arrangement) with a similar repeat. In another embodiment, said repeat used to form the synthetic spider silk of the invention is a direct repeat. In some embodiments, said repeat is not found in nature (i.e., is not a naturally occurring amino acid sequences). In some embodiments, said single unit repeat (or alternatively direct repeat) comprises not more than one variation within its amino acid sequence.

In additional embodiments, synthetic spider silks of the invention comprise a number of repetitions of one unit repeat together with a number of repetitions of a second unit repeat. Such a structure would be similar to a typical block copolymer. Unit repeats of several different sequences can also be combined to provide a synthetic spider silk protein having properties suited to a particular application.

An exemplary sequence comprising repetitive sequences is ADF-4:

```
(SEQ ID NO: 10)
AAAAAAASGSGGYGPENQGPSGPVAYGPGGPVSSAAAAAAAGSGPGGYGP

ENQGPSGPGGYGPGGSGSSAAAAAAAASGPGGYGPGSQGPSGPGGSGGYG

PGSQGPSGPGASSAAAAAAAASGPGGYGPGSQGPSGPGAYGPGGPGSSAA

ASGPGGYGPGSQGPSGPGGSGGYGPGSQGPSGPGGPGASAAAAAAAAASG

PGGYGPGSQGPSGPGAYGPGGPGSSAAASGPGGYGPGSQGPSGPGAYGPG

GPGSSAAAAAAAGSGPGGYGPGNQGPSGPGGYGPGGPGSSAAAAAAASGP

GGYGPGSQGPSGPGVYGPGGPGSSAAAAAAAGSGPGGYGPGNQGPSGPGG

YGPGGSGSSAAAAAAAASGPGGYGPGSQGPSGPGGSGGYGPGSQGPSGPG

ASSAAAAAAAASGPGGYGPGSQGPSGPGAYGPGGPGSSAAASGPGGYGPG

SQGPSGPGAYGPGGPGSSAAAAAAASGPGGYGPGSQGPSGPGGSRGYGPG

SQGPGGPGASAAAAAAAAASGPGGYGPGSQGPSGPGYQGPSGPGAYGPSP

SASAS.
```

In some embodiments, the synthetic repetitive sequence of the invention is based on (e.g., has a high percentage identity, as defined hereinbelow) one or more repetitive sequences derived from ADF-4 (SEQ ID NO: 10). In some embodiments, the synthetic repetitive sequence of the invention is based on (e.g., has a high percentage identity) one or more repetitive sequences derived from any one of SEQ ID NO: 18-32. As used herein, the term "based on" refers to a sequence having a high percentage of homology to a repetitive sequence. As use herein, high percentage of homology includes anyone of: at least 70%, at least 75%, at least 80%, at least 85%, at least 90%, at least 91%, at least 92%, at least 93%, at least 94%, at least 95%, at least 96%, at least 97%, at least 98%, or 99% identity over a specified region of an ADF-4 sequence.

In some embodiments, each repetitive sequence comprises up to 60 amino acids, up to 55 amino acids, up to 50 amino acids, up to 49 amino acids, up to 48 amino acids, up to 47 amino acids, up to 46 amino acids, up to 45 amino acids, up to 44 amino acids, up to 43 amino acids, up to 42 amino acids, up to 41 amino acids, up to 40 amino acids, up to 39 amino acids, up to 38 amino acids, up to 37 amino acids, up to 36 amino acids or up to 35 amino acids, wherein possibility represents a separate embodiment of the present invention. In some embodiments, each repetitive sequence comprises 5 to 60 amino acids, 10 to 55 amino acids, 15 to 50 amino acids, 20 to 45 amino acids, 25 to 40 amino acids, acids, 25 to 39 amino acids or 28 to 36 amino acids, wherein possibility represents a separate embodiment of the present invention. In some embodiments, each repetitive sequence comprises 30 to 40 amino acids, 31 to 39 amino acids, 32 to 38 amino acids, 33 to 37 amino acids, 34 to 36 amino acids, wherein possibility represents a separate embodiment of the present invention. In an additional embodiment, each repetitive sequence comprises 35 amino acids.

In some embodiments, n is an integer equal to any one of 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69 and 70.

In some embodiments, m is an integer equal to any one of 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69 and 70.

In another embodiment, the ratio of 'n' to 'm' is in the range of 2:1-1:2. In another embodiment, 'n' and 'm' are equal.

In some embodiments, said 'n' is identical for each type of protein in said mixture. The term "n is identical for each type of protein in said mixture" as used herein relates to the number of repetitive sequence for each type of protein, i.e., for one or more proteins having an identical molecular weight. As a non-limiting example, for a mixture of proteins having 16 types of proteins of differing molecular weight, each group of proteins has a different number of repetitive sequences.

In some embodiments, the various groups of proteins of said mixture have an inverse proportion between the number of repetitive sequence for each type of protein and the molar ratio of said group. In some embodiments, for each group of proteins (e.g., having an identical number of repeats), the lower the molecular weight of said proteins, the higher the molar ratio of said group.

In another embodiment, each repeat has a molecular weight in the range of 2 kDa to 3.5 kDa, in the range of 2.1 kDa to 3.4 kDa, in the range of 2.2 kDa to 3.3 kDa, in the range of 2.4 kDa to 3.2 kDa, in the range of 2.5 kDa to 3.1 kDa, in the range of 2.6 kDa to 3 kDa, or in the range of 2.7 kDa to 2.9 kDa, wherein each possibility represents a separate embodiment of the present invention. In another embodiment, each repeat has a molecular weight in the range of about 2.8 kDa.

In another embodiment, the composition comprises two or more proteins of said mixture having molecular weight increment of 2 kDa to 3.5 kDa, of 2.1 kDa to 3.4 kDa, of 2.2 kDa to 3.3 kDa, of 2.4 kDa to 3.2 kDa, of 2.5 kDa to 3.1 kDa, of 2.6 kDa to 3 kDa, or of 2.7 kDa to 2.9 kDa, wherein each possibility represents a separate embodiment of the present invention. In another embodiment, the composition comprises two or more proteins of said mixture having molecular weight increment of about 2.8 kDa.

In some embodiments, said repetitive region has a first moiety and a second moiety, wherein the first moiety and the second moiety are contiguous (i.e., immediately adjacent to each other). Typically, the first moiety and the second moiety are linked by a peptide bond.

In some embodiments, the first moiety of said repetitive region is an amino acid sequence of 5-30 amino acids comprising at least 95%, at least 90%, at least 85%, at least 80%, at least 75%, at least 60%, at least 55%, or at least 50% alanine residues.

In some embodiments, the first moiety may comprise one or more glycine residues. In some embodiments, the first moiety comprises up to 5%, up to 10%, up to 15%, up to 20%, up to 25%, up to 30%, up to 45%, or up to 50% glycine residues.

In some embodiments, the first moiety comprises between one to fifteen repeats of an alanine-glycine dipeptide, such as in the formula of: $(AG)_{1-15}$.

In some embodiments, the first moiety comprises between one to fifteen repeats of a glycine-alanine dipeptide, such as in the formula of: $(GA)_{1-15}$.

In some embodiments, the second moiety of said repetitive region is an amino acid sequence of 20-60 amino acids comprising at least 80% residues selected from the group consisting of glycine, serine, proline and tyrosine.

In some embodiments, the second moiety of said repetitive region is an amino acid sequence of 20-60 amino acids comprising at least 50%, at least 55%, at least 60%, at least 65%, at least 70%, at least 75%, at least 80%, at least 85%, at least 90%, at least 95% residues selected from the group consisting of glycine, serine, proline and tyrosine. In some embodiments, the second moiety of said repetitive region comprises not more than one or two glutamine residues. One skilled in the art will appreciate that the exact quantity and order of the glycine, serine, proline and tyrosine residues in the repetitive region may differ as long as the sequence forms self-assembling fibers.

In some embodiments, said repetitive region comprises:
(i) 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49% or 50% alanine residues, or any range therebetween;
(ii) 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49% or 50%, 51%, 52%, 53%, 54%, 55%, 56%, 57%, 58%, 59% or 60% glycine residues, or any range therebetween;
(iii) 10%, 11%, 12%, 13%, 14%, 15%, 16%, 17%, 18%, 19%, 20%, 21%, 22%, 23%, 24%, 25%, 26%, 27%, 28%, 29% or 30% serine residues, or any range therebetween;
(iv) 10%, 11%, 12%, 13%, 14%, 15%, 16%, 17%, 18%, 19%, 20%, 21%, 22%, 23%, 24%, 25%, 26%, 27%, 28%, 29% or 30% proline residues, or any range therebetween;

(v) 1%, 2%, 3%, 4%, 5%, 6%, 7%, 8%, 9% or 10% tyrosine residues, or any range therebetween;
(vi) 1%, 2%, 3%, 4%, 5%, 6%, 7%, 8%, 9% or 10% glutamine residues, or any range therebetween; and
(vii) 0%, 1%, 2%, 3%, 4%, 5%, arginine residues, or any range therebetween.

In some embodiments, said repetitive region comprises 13-42% of alanine residues, 25-55% glycine residues, 10-18% serine residues, 12-21% proline residues, 4-7% tyrosine residues, 4-7% glutamine residues, and 0-3% arginine residues.

In some embodiments, said repetitive region of a MaSP1 protein has the amino acid sequence as set forth in SEQ ID NO: 1

$(X_1)_Z X_2 GPGGYGPX_3X_4X_5GPX_6GX_7GGX_8GPG GPGX_9X_{10}$ wherein $X_1$ is, independently, at each instance A or G wherein at least 50% of $(X_1)_Z$ is A, Z is an integer between 5 to 30; $X_2$ is S or G; $X_3$ is G or E; $X_4$ is G, S or N; $X_5$ is Q or Y; $X_6$ is G or S; $X_7$ is P or R; $X_8$ is Y or Q; $X_9$ is G or S; and $X_{10}$ is S or G.

In some embodiments, said repetitive region has the amino acid sequence as set forth in SEQ ID NO: 8

$(X_1)_Z X_2 GPGGYGPGX_3X_4GPX_5GX_6GGX_7GPG GPGX_8X_9$ wherein $X_1$ is, independently, at each instance A or G wherein at least 50% of $(X_1)_Z$ is A, Z is an integer between 5 to 30; $X_2$ is S or G; $X_3$ is G or S; $X_4$ is Q or Y; $X_5$ is G or S; $X_6$ is P or R; $X_7$ is Y or Q; $X_8$ is G or S; and $X_9$ is S or G.

In some embodiments, Z (of SEQ ID NO: 1 or 8), is an integer between 6 to 11, an integer between 6 to 10 or an integer between 7 to 9. In one embodiment, Z is an integer selected from 5, 6, 7, 8, 9, 10, 11, and 12. In another embodiment, Z is 8.

In another embodiment, said repetitive region of a MaSP1 protein comprises the amino acid sequence as set forth in SEQ ID NO: 2 (SGPGGYGPGSQGPSGPG-GYGPGGPGSS). In another embodiment, said repetitive region of a MaSP1 protein comprises the amino acid sequence as set forth in SEQ ID NO: 3 (AAAAAAAASGPGGYGPGSQGPSGPG-GYGPGGPGSS).

In another embodiment, said homolog shares at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99% homology with SEQ ID NO: 1.

In another embodiment, said homolog shares at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99% homology with SEQ ID NO: 2.

In another embodiment, said homolog shares at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98% or at least 99% homology with SEQ ID NO: 3.

In another embodiment, said repetitive region of a MaSP1 protein comprises the amino acid sequence as set forth in SEQ ID NO: 4. In another embodiment, said repetitive region of a MaSP1 protein has the amino acid sequence as set forth in SEQ ID NO: 10.

In another embodiment, each protein of said mixture further comprises a single N-terminal region selected from the group consisting of: SEQ ID NO: 5 (MSYYHHHHHHDYDIPTTENLYFQGAMDPE-FKGLRRRAQLV); SEQ ID NO: 6 (MSYYHHHHHHDY-DIPTTENLYFQGAMDPEFKGLRRRAQLVRPL-SNLDNA); SEQ ID NO: 7 (MSYYHHHHHHDYDIPTTENLYFQGAMDPE-FKGLRRRAQLVDPPGCRNSARAGSS), or any functional homolog, variant, derivative, or fragment thereof. In another embodiment, said homolog of said C-terminal region shares at least 70% homology with any one of SEQ ID NOs: 5-7.

In another embodiment, each protein of said mixture further comprises a single C-terminal region a SEQ ID NO: 9 (GPSGPGAYGPSPSASASVAASRLSSPAASSRVS-SAVSSLVSSGPTNGAAVSGALNSLVS QISASNPGLSGCDALVQALLELVSALVAILSSAS-IGQVNVSSVSQSTQMISQALS), or any functional homolog, variant, derivative, fragment or mutant thereof. In another embodiment, said homolog of said N-terminal region shares at least 70% homology with SEQ ID NO: 9.

In some embodiments, one or more proteins of said mixture further comprises at least one tag sequence. Non-limiting examples of tags which may be used in the present invention include a His tag, a HA tag, a T7 tag, and the like. An exemplary His tag comprises six His residues or consists of six His residues as set forth in SEQ ID NO: 11 (HHHHHH). In another embodiment, the tag is a HA tag comprising or consisting of the amino acid sequence as set forth in SEQ ID NO: 12 (YPYDVPDYA). In another embodiment, the tag is a T7 tag comprising or consisting of the amino acid sequence as set forth in SEQ ID NO: 13 (MASMTGGQQMG). The skilled person is well aware of alternative suitable tags or other fusion partners.

"Amino acid" as used herein, refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. "Amino acid analogs" refers to compounds that have the same fundamental chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups or modified peptide backbones, but retain the same basic chemical structure as a naturally occurring amino acid. "Amino acid mimetics" refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission.

"Amino acid sequence" or "peptide sequence" is the order in which amino acid residues, connected by peptide bonds, lie in the chain in peptides and proteins. The sequence is generally reported from the N-terminal end containing free amino group to the C-terminal end containing free carboxyl group Amino acid sequence is often called peptide, protein sequence if it represents the primary structure of a protein, however one must discern between the terms "amino acid sequence" or "peptide sequence" and "protein", since a protein is defined as an amino acid sequence folded into a specific three-dimensional configuration and that had typically undergone post-translational modifications, such as phosphorylation, acetylation, glycosylation, sulfhydryl bond formation, cleavage and the likes.

As used herein, "isolated" or "substantially purified", in the context of synthetic spider silk amino-acid sequences or nucleic acid molecules encoding the same, as exemplified by the invention, means the amino-acid sequences or polynucleotides have been removed from their natural milieu or have been altered from their natural state. As such "isolated" does not necessarily reflect the extent to which the amino-acid sequences or nucleic acid molecules have been purified. However, it will be understood that such molecules that have been purified to some degree are "isolated". If said molecules do not exist in a natural milieu, i.e. it does not exist in nature, the molecule is "isolated" regardless of where it is present. By way of example, amino-acid sequences or polynucleotides that do not naturally exist in humans are "isolated" even when they are present in humans.

The term "isolated" or "substantially purified", when applied to an amino acid sequence or nucleic acid, denotes that the amino acid sequence or nucleic acid is essentially free of other cellular components with which they are associated in the natural state. It may be in a homogeneous state, or alternatively in either a dry or aqueous solution. Purity and homogeneity are typically determined using analytical chemistry techniques such as polyacrylamide gel electrophoresis or high performance liquid chromatography. An amino acid sequence or nucleic acid which is the predominant species present in a preparation is substantially purified.

In some embodiments, said repeats are of a homolog, variant, derivative of a repetitive region of a MaSP1 protein or fragment thereof. In some embodiments, said repeats are of a homolog, variant, derivative of a repetitive region of an ADF-4 protein or fragment thereof. In one exemplary embodiment, said repeat comprises or consists of a polynucleotide sequence as set forth in any one of SEQ ID NO: 45-47.

As used herein, the term "functional" as in "functional homolog, variant, derivative or fragment", refers to an amino acid sequence which possesses biological function or activity that is identified through a defined functional assay. More specifically, the defined functional assay is the formation of self-assembling fibers in cells expressing said functional homolog, variant, derivative or fragment.

An amino acid sequence or a nucleic acid sequence is said to be a homolog of a corresponding amino acid sequence or a nucleic acid, when the homology is determined to be at least 50%, at least 55%, at least 60%, at least 65%, at least 70%, at least 75%, at least 80%, at least 85%, at least 90%, at least 92%, at least 94%, at least 96%, at least 98% or at least 99%.

Homology, as used herein, may be determined on the basis of percentage identity between two amino acid (peptide) or DNA sequences. In general the two sequences to be compared are aligned to give a maximum correlation between the sequences. The alignment of the two sequences is examined and the number of positions giving an exact amino acid (or nucleotide) correspondence between the two sequences determined, divided by the total length of the alignment multiplied by 100 to give a percentage identity figure. This percentage identity figure may be determined over the whole length of the sequences to be compared, which is particularly suitable for sequences of the same or very similar lengths and which are highly homologous, or over shorter defined lengths, which is more suitable for sequences of unequal length or which have a lower level of homology. Methods for comparing the identity of two or more sequences are well known in the art. Thus, for instance, programs available in the Wisconsin Sequence Analysis Package, version 9.1, for example the programs GAP and BESTFIT, may be used to determine the percentage identity between two amino acid sequences and the percentage identity between two polynucleotides sequences. BESTFIT uses the "local homology" algorithm of Smith and Waterman and finds the best single region of similarity between two sequences. BESTFIT is more suited to comparing two polypeptide or two polynucleotide sequences which are dissimilar in length, the program assuming that the shorter sequence represents a portion of the longer. In comparison, GAP aligns two sequences finding a "maximum similarity" according to the algorithm of Needleman and Wunsch. GAP is more suited to comparing sequences which are approximately the same length and an alignment is expected over the entire length. Preferably the parameters "Gap Weight" and "Length Weight" used in each program are 50 and 3 for polynucleotide sequences and 12 and 4 for polypeptide sequences, respectively. Preferably, percentage identities and similarities are determined when the two sequences being compared are optimally aligned.

The terms "identical", "substantial identity", "substantial homology" or percent "identity", in the context of two or more amino acids or nucleic acids sequences, refer to two or more sequences or subsequences that are the same or have a specified percentage of amino acid residues or nucleotides that are the same (i.e., about 60% identity, or at least 65%, at least 70%, at least 75%, at least 80%, at least 85%, at least 90%, at least 91%, at least 92%, at least 93%, at least 94%, at least 95%, at least 96%, at least 97%, at least 98%, or 99% identity over a specified region (e.g., amino acid sequence SEQ ID NO: 2 or 3), when compared and aligned for maximum correspondence over a comparison window or designated region) as measured using a BLAST or BLAST 2.0 sequence comparison algorithms with default parameters described below, or by manual alignment and visual inspection. Such sequences are then said to be "substantially identical". This definition also refers to, or may be applied to, the compliment of a test sequence. The definition also includes sequences that have deletions and/or additions, as well as those that have substitutions. The preferred algorithms can account for gaps and the like.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

It should be appreciated that the invention further encompasses amino acid sequence comprising n repeats of a variant of any one of SEQ ID NO: 1, 2, or 3. As used herein, the term "variant" or "substantially similar" comprises sequences of amino acids or nucleotides different from the specifically identified sequences, in which one or more (e.g., 1, 2, 3, 4, 5, 6, 7, 8, 9, 10, 20 or 25) amino acid residues or nucleotides are deleted, substituted or added. The variants may be allelic variants occurring naturally or variants of non-natural origin. The variant or substantially similar sequences refer to fragments of amino acid sequences or nucleic acids that may be characterized by the percentage of the identity of their amino acid or nucleotide sequences with the amino acid or nucleotide sequences described herein, as determined by common algorithms used in the state-of-the-art. The preferred fragments of amino acids or nucleic acids are those having a sequence of amino acids or nucleotides with at least around 40 or 45% of sequence identity, preferentially around 50% or 55% of sequence identity, more preferentially around 60% or 65% of sequence identity, more preferentially around 70% or 75% of sequence identity, more preferentially around 80% or 85% of sequence identity, yet more preferentially around 90%, 91%, 92%, 93%, 94%, 95%, 96%, 97%, 98% or 99% of sequence identity when compared to the sequence of reference.

The terms derivatives and functional derivatives as used herein mean the amino acid sequence of the invention with any insertions, deletions, substitutions and modifications.

It should be appreciated that by the term "insertions", as used herein it is meant any addition of amino acid residues to the sequence of the invention, of between 1 to 50 amino acid residues, specifically, between 20 to 1 amino acid residues, and more specifically, between 1 to 10 amino acid residues. Most specifically, 1, 2, 3, 4, 5, 6, 7, 8, 9 and 10 amino acid residues. Further, the amino acid sequence of the invention may be extended at the N-terminus and/or C-terminus thereof with various identical or different amino acid residues.

Amino acid "substitutions" are the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

In another embodiment, the repeat sequence of the invention has 17 or fewer, 16 or fewer, 15 or fewer, 14 or fewer, 13 or fewer, 12 or fewer, 11 or fewer, 10 or fewer, 9 or fewer, 8 or fewer, or 7 or fewer amino acid substitutions to the sequence of any one of SEQ ID NO: 2 or 3. In one embodiment, the repeat sequence of the invention has at least 2, at least 3, at least 4, at least 5, at least 6, at least 7, at least 8, at least 9, at least 10, at least 11, at least 12, or at least 13 amino acid substitutions to the sequence of any one of SEQ ID NO: 2 or 3.

With respect to amino acid sequences, one of skill will recognize that individual substitutions, deletions or additions to an amino acid, nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologues, and alleles of the invention.

For example, substitutions may be made wherein an aliphatic amino acid (G, A, I, L, or V) is substituted with another member of the group, or substitution such as the substitution of one polar residue for another, such as arginine for lysine, glutamic for aspartic acid, or glutamine for asparagine. Each of the following eight groups contains other exemplary amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M).

Conservative nucleic acid substitutions are nucleic acid substitutions resulting in conservative amino acid substitutions as defined above.

Variants of the amino acid sequences of the invention may have at least 80% sequence similarity, at least 85% sequence similarity, 90% sequence similarity, or at least 95%, 96%, 97%, 98%, or 99% sequence similarity at the amino acid level, with a repeating unit denoted by aby one of SEQ ID NO: 2 or 3.

The amino acid sequence of the invention may comprise n repeats of SEQ ID NO. 1 or SEQ ID NO. 3 or of any fragment thereof. A "fragment" constitutes a fraction of the amino acid or DNA sequence of a particular region. A fragment of the peptide sequence is at least one amino acid shorter than the particular region, and a fragment of a DNA sequence is at least one base-pair shorter than the particular region. The fragment may be truncated at the C-terminal or N-terminal sides, or both. An amino acid fragment may comprise at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 24, at least 26, at least 27, at least 28, at least 29, at least 30, at least 31, at least 32, at least 33 or at least 34 amino acids of SEQ ID NO. 1 or 3.

Mutants of the amino acid sequences of the invention are characterized in the exchange of one (point mutant) or more, about up to 10, of its amino acids against one or more of another amino acid. They are the consequence of the corresponding mutations at the DNA level leading to different codons.

Still further, the invention concerns derivatives of the amino acid sequence of the invention. Derivatives of the amino acid sequences of the invention are, for example, where functional groups, such as amino, hydroxyl, mercapto or carboxyl groups, are derivatised, e.g. glycosylated, acylated, amidated or esterified, respectively. In glycosylated derivatives an oligosaccharide is usually linked to asparagine, serine, threonine and/or lysine. Acylated derivatives are especially acylated by a naturally occurring organic or inorganic acid, e.g. acetic acid, phosphoric acid or sulphuric acid, which usually takes place at the N-terminal amino group, or at hydroxy groups, especially of tyrosine or serine, respectively. Esters are those of naturally occurring alcohols, e.g. methanol or ethanol. Further derivatives are salts, especially pharmaceutically acceptable salts, for example metal salts, such as alkali metal and alkaline earth metal salts, e.g. sodium, potassium, magnesium, calcium or zinc salts, or ammonium salts formed with ammonia or a suitable organic amine, such as a lower alkylamine, e.g. triethylamine, hydroxy-lower alkylamine, e.g. 2-hydroxyethylamine, and the like.

According to some aspects, the invention provides an isolated nucleic acid sequence encoding two or more proteins of said the mixture of proteins of the present invention. According to some embodiments, the invention provides an isolated nucleic acid sequence encoding the protein mixture of the present invention.

"Nucleic acid" refers to a molecule which can be single stranded or double stranded, composed of monomers (nucleotides) containing a sugar, phosphate and either a purine or pyrimidine. In bacteria, lower eukaryotes, and in higher animals and plants, "deoxyribonucleic acid" (DNA) refers to the genetic material while "ribonucleic acid" (RNA) is involved in the translation of the information from DNA into proteins.

Due to the degenerative nature of the genetic code it is clear that a plurality of different nucleic acid sequences can be used to code for the amino acid sequences of the invention. It should be appreciated that the codons comprised in the nucleic acid sequence of the invention may be optimized for expression in Sf9 host cells.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA. Within the context of the present invention, genes and DNA coding regions are codon-optimized for optimal expression in host cells, and in a specific example, Sf9 *Spodoptera frugiperda* insect cells.

The term "expression" as used herein is intended to mean the transcription and translation to gene product from a gene coding for the sequence of the gene product. In the expression, a DNA chain coding for the sequence of gene product is first transcribed to a complementary RNA which is often a messenger RNA and, then, the thus transcribed messenger RNA is translated into the above-mentioned gene product if the gene product is a protein.

In some embodiments, the invention relates to one or more expression vectors comprising a nucleic acid sequence encoding the proteins mixture of the invention. In some embodiments, the invention relates to one or more expression vectors comprising a nucleic acid sequence encoding at least a portion of the proteins mixture of the invention (e.g., two or more group of proteins having a differing molecular weight). The amino acid sequence encoded by the nucleic acid sequence comprised within the expression vector of the invention may optionally further comprise at least one of a C-terminal region (e.g., denoted as SEQ ID NO: 9); and an N-terminal region (e.g., selected from SEQ ID NO: 5-7). It should be noted that the nucleic acid sequence is under expression control of operably linked promoter and, optionally, regulatory sequences.

As used herein, a "vector", "expression vector" or "plasmid" as referred to herein is an extra-chromosomal element often carrying genes which are not part of the central metabolism of the cell, and usually in the form of circular double-stranded DNA molecules. It may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification and selection of cells which have been transformed or transfected with the vector. As used herein, "transformation" or "transfection" is the acquisition of new genes in a cell by the incorporation of nucleic acid. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined, namely, the expression of the synthetic spider silk proteins.

In specific embodiments, the vector is a viral vector, most specifically a baculovirus vector system or a vaccinia virus vector system. Examples of such commercially available baculovirus systems Baculo-Gold®, Flash-Bac® and the bac to bac system. Further viral vector systems may also be used in this invention. From case to case, a modification of the vector may be needed. Examples for further viral vectors are adenoviruses and all negative-strand RNA-viruses, e.g. rabies, measles, RSV, etc.

In one embodiment, a baculovirus system as used for expressing the synthetic silk protein of the invention. Baculoviruses are a family of large rod-shaped viruses that can be divided to two genera: nucleopolyhedroviruses and granuloviruses. They have a restricted range of hosts that they can infect that is typically restricted to a limited number of closely related insect species. Because baculoviruses are not harmful to humans they are a safe option for use in research and commercial or industrial applications. Baculovirus expression in insect cells represents a robust method for producing recombinant glycoproteins, a significant advantage over prokaryotic expression which is lacking in terms of glycosylation, and consequently, proper protein folding.

As indicated above, the expression vector of the invention is operably linked to a promoter. The terms "promoter" and "promoter region" refer to a sequence of DNA, usually upstream of (5' to) the protein coding sequence of a structural gene, which controls the expression of the coding region by providing the recognition for RNA polymerase and/or other factors required for transcription to start at the correct site. Promoter sequences are necessary but not always sufficient to drive the expression of the gene. Theterm "suitable promoter" will refer to any eukaryotic or prokaryotic promoter capable of driving the expression of a synthetic spider silk variant gene.

Promoters which are useful to drive expression of heterologous DNA fragments in Sf9 are numerous and familiar to those skilled in the art. Virtually any promoter capable of driving the gene encoding a silk variant protein is suitable for the present invention. For example, polyhedrin, basic protein, p10, OpIE2 and gp4 promoters may be suitable promoters for said expression.

A coding sequence and regulatory sequences are said to be "operably linked" or "operably joined" when they are covalently linked in such a way as to place the expression or transcription of the coding sequence under the influence or control of the regulatory sequences. If the regulatory sequence is positioned relative to the gene such that the regulatory sequence is able to exert a measurable effect on the amount of gene product produced, then the regulatory sequence is operably linked to the gene. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribing and 5' non-translating sequences involved with initiation of transcription and translation respectively, such as a TATA box, capping sequence, CAAT sequence. Especially, such 5' non-transcribing regulatory sequences will include a promoter region which includes a promoter sequence for transcriptional control of the operably joined gene. Regulatory sequences may also include enhancer sequences or upstream activator sequences, as desired.

"Regulation" and "regulate" refer to the modulation of gene expression controlled by DNA sequence elements located primarily, but not exclusively upstream of (5' to) the transcription start of a gene. Regulation may result in an all or none response to stimulation, or it may result in variations in the level of gene expression.

In a further aspect, the invention provides a host cell transformed with the expression vector according to the invention.

"Cells", "host cells" or "recombinant host cells" are terms used interchangeably herein. It is understood that such terms refer not only to the particular subject cells but to the progeny or potential progeny of such a cell. Because certain modification may occur in succeeding generation due to either mutation or environmental influences, such progeny may not, in fact, be identical to the parent cell, but are still included within the scope of the term as used herein.

"Host cell" as used herein refers to cells which can be recombinantly transformed with naked DNA or expression vectors constructed using recombinant DNA techniques. A drug resistance or other selectable marker is intended in part to facilitate the selection of the transformants. Additionally, the presence of a selectable marker, such as drug resistance marker may be of use in keeping contaminating microorganisms from multiplying in the culture medium. Such a pure culture of the transformed host cell would be obtained by culturing the cells under conditions which require the induced phenotype for survival.

The host cells of the invention are transformed or transfected with the expression vector descried herein to express the synthetic spider silk protein of the invention. "Transformation", as used herein, refers to a process in which a cell's genotype is changed as a result of the cellular uptake of exogenous DNA or RNA, and, for example, the transformed cell expresses a recombinant form of the desired synthetic spider silk protein. The term "transfection" means the introduction of a nucleic acid, e.g., naked DNA or an expression vector, into a recipient cells by nucleic acid-mediated gene transfer.

In one specific embodiment, the host cells transformed with the expression vector according to the invention are insect cells. As insect cells, *Lepidoptera* insect cells may be used, more specifically cells from *Spodoptera frugiperda* and from *Trichoplusia ni*. Most specifically, the insect cell is a Sf9, Sf21 or high 5 cells.

In some embodiments, the silk protein of the invention are devoid of post translational modifications.

In some embodiments, the silk protein of the invention are biodegradable. This characteristic may be of importance, for example, in the field of medicine, whenever the silk proteins are intended for an in vivo use, in which biological degradation is desired. This characteristic may in particular find application in suture materials and wound closure and coverage systems.

According to some aspects, the invention provides an expression vector comprising the nucleic acid sequence of the present invention, wherein said nucleic acid sequence is under expression control of an operably linked promoter and, optionally, regulatory sequences.

Fibers

According to some aspects, the invention provides a fiber comprising the composition of the invention.

A "fiber" as used herein, is meant a fine cord of fibrous material composed of two or more filaments twisted together. By "filament" is meant a slender, elongated, threadlike object or structure of indefinite length, ranging from microscopic length to lengths of a mile or greater. Specifically, the synthetic spider silk filament is microscopic, and is proteinaceous. By "biofilament" is meant a filament created from a protein, including recombinantly produced spider silk protein. The term "fiber" does not encompass unstructured aggregates or precipitates.

In some embodiments, the fiber has a thickness diameter of at least 50 nm. In some embodiments, the fiber has a thickness diameter of at most 350 nm. In some embodiments, the fiber has a thickness diameter of at least 50-350 nm, or any numerical value therebetween. As demonstrated herein (see, FIG. 1) the final fiber is composed of nanofibers with a diameter of 5-10 nm.

In some embodiments, the fiber has a considerable extension in length compared to its thickness, preferably above 20 am.

By "micro fiber" is meant a filament having a fineness of less than 1 denier (denier is defined as the mass in grams per 9,000 meters).

In some embodiments, the fiber of the proteins is characterized by size of at least one dimension thereof (e.g., diameter, length).

For example, and without limitation, the diameter of the fiber is between 10 nm-1 μm, 20-100 nm, or 10-50 nm.

In some embodiments, the fiber is composed of nanofibrils. In some embodiments, the nano-fibrils have a diameter of e.g., 1 nm, about 2 nm, about 3 nm, about 4 nm, about 5 nm, about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 21 nm, about 22 nm, about 23 nm, about 24 nm, about 25 nm, about 26 nm, about 27 nm, about 28 nm, about 29 nm, about 30 nm, about 31 nm, about 32 nm, about 33 nm, about 34 nm, about 35 nm, about 36 nm, about 37 nm, about 38 nm, about 40 nm, about 42 nm, about 44 nm, about 46 nm, about 48 nm, or 50 nm, including any value or range therebetween. In one embodiment, the nano-fibrils have a diameter of 3-7 nm. In one embodiment, the nano-fibrils have a diameter of 4-6 nm.

In some embodiments, the length of the disclosed fiber is between 1-200 μm, 10-100 μm, 100 to 500 μm or 200-500 μm.

By one embodiment, the fiber of the invention assembles by self-assembly. By "self-assembly" it is meant that monomers of said fibers, i.e., the synthetic spider silk protein of the invention, bind each other spontaneously, in an energetically favorable manner, under normal physiologic conditions, or at room temperature, to create the macromolecular fiber structure having the properties described herein. Furthermore, the fibers of the invention are extremely resilient, and once assembled, may withstand extreme chemical assaults, such as solubilization in 10% SDS and boiling for at least 1 hour.

"Tenacity" or "tensile strength" refers to the amount of weight a filament can bear before breaking. The maximum specific stress that is developed is usually in the filament, yarn or fabric by a tensile test to break the materials. According to specific embodiments, the fiber of the invention has tensile strength of about 100-3000 MPa (MPa=N/mm2), about 300-3000 MPa, about 500-2700 MPa, about 700-2500 MPa, about 900-2300 MPa, about 1100-2000 MPa, about 1200-1800 MPa, about 1300-1700 MPa or about 1400-1600 MPa. More specifically, about 1500 MPa.

"Toughness" refers to the energy needed to break the fiber. This is the area under the stress strain curve, sometimes referred to as "energy to break" or work to rupture. According to particular embodiments, the fiber of the invention a toughness of about 20-1000 MJ/m3, about 50-950 MJ/m3, about 100-900 MJ/m3, about 120-850 MJ/m3, about 150-800 MJ/m3, about 180-700 MJ/m3, about 180-750 MJ/m3, about 250-700 MJ/m3, about 280-600 MJ/m3, about 300-580 MJ/m3, about 310-560 MJ/m3, about 320-540 MJ/m3 or about 350-520 MJ/m3, most specifically about 350-520 MJ/m3.

"Elasticity" refers to the property of a body which tends to recover its original size and shape after deformation. Plasticity, deformation without recovery, is the opposite of elasticity. On a molecular configuration of the fiber, recoverable or elastic deformation is possible by stretching (reorientation) of inter-atomic and inter-molecular structural bonds. Conversely, breaking and re-forming of intermolecular bonds into new stabilized positions causes non-recoverable or plastic deformations.

"Extension" refers to an increase in length expressed as a percentage or fraction of the initial length.

By "fineness" is meant the mean diameter of a fiber or filament (e.g., a biofilament), which is usually expressed in microns (micrometers).

In some embodiments, the disclosed composition is characterized by a defined differential scanning calorimetry (DSC) pattern. In some embodiments, by "DSC pattern" it is meant to refer to the position of the peaks. In some embodiments, by "peak" it is meant to refer to exothermic peak. Hereinthroughout, "the position of the peaks" or "peak position" refers to the peaks along the temperature axis in a thermogram pattern, and, in some embodiments, may refers to the peak position at any peak intensity. One skilled in the art will appreciate that the data obtained in DSC measurements depend, in part, on the instrument used and the environmental conditions at the time measurements are carried out (e.g., humidity).

In some embodiments, the disclosed composition is characterized by a DSC pattern exhibiting at least an endothermic peak in the range of from 250° C. to 330° C. In some embodiments, the disclosed composition is characterized by a DSC pattern exhibiting at least an endothermic peak in the range of from 290° C. to 310° C. In some embodiments, the disclosed composition is characterized by a DSC pattern exhibiting at least an endothermic peak in the range of from 295° C. to 305° C.

In some embodiments, the disclosed composition is characterized by a DSC pattern exhibiting an endothermic peak at least in the range of from 260° C. to 320° C. and 220° C. to 250° C. In some embodiments, the disclosed composition is further characterized by an additional DSC exothermic peak in the range of from 120° C. to 160° C.

In some embodiments, the disclosed composition is devoid of DSC peaks in the range of about −100° C. to about 220° C. In some embodiments, the disclosed compound is devoid of DSC peaks in the range of about −100° C. to about 25° C. In some embodiments, the disclosed composition is characterized by at least a DSC pattern exhibiting devoid of an exothermic peak in the range of 40° C. to 70° C.

In some embodiments, the disclosed compound is devoid of DSC peaks in the range of about −100° C. to about −50° C. In some embodiments, the disclosed compound is devoid of DSC peaks in the range of about −50° C. to about 0° C. In some embodiments, the disclosed compound is devoid of DSC peaks in the range of about −0° C. to about −25° C.

Compositions

According to particular embodiments, the composition may be provided in the form of a gel, foam, or a coating used to coat stents and implants, or in forms useful for tissue engineering purposes. In other embodiments, the composition of the invention is a pharmaceutical composition.

It should be noted that the pharmaceutical composition of the invention may comprise at least one of the amino acid sequence, the recombinant protein and the fiber of the invention and be administered directly to the subject to be treated. Formulations typically comprise at least one active ingredient, as defined above, together with one or more acceptable carriers thereof.

Formulations are particularly suitable for topical administration, or for use as coating for invasive medical devices or as scaffolding for tissue engineering, however subcutaneous, intradermal, intramuscular, intraperitoneal, intravenous and even oral, rectal, nasal, or parenteral administration routes are not overlooked.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

The pharmaceutical compositions of the invention generally comprise a buffering agent, an agent who adjusts the osmolarity thereof, and optionally, one or more pharmaceutically acceptable carriers, excipients and/or additives as known in the art. Supplementary active ingredients can also be incorporated into the compositions. The carrier can be solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

As used herein "pharmaceutically acceptable carrier" includes any and all solvents, dispersion media, coatings, antibacterial and antifungal agents and the like. The use of such media and agents for pharmaceutical active substances is well known in the art. Except as any conventional media or agent is incompatible with the active ingredient, its use in the therapeutic composition is contemplated.

The pharmaceutical composition of the invention comprising at least one of the amino acid sequence, the recombinant protein and the fiber of the invention may be especially suited for the production of transdermal patches, i.e., a transdermal delivery systems, elastic wound dressing, sutures, coatings or medical fabrics requiring resilience, elasticity, tenacity which are non-toxic.

In yet further embodiments, the composition of the invention may be a cosmetic composition. The term "cosmetic composition" relates to a composition having beneficial skin or other superficial tissue esthetic properties, such as improving or enhancing skin tone and color, hair color and shine, hiding superficial tissue imperfections such as blemishes and scars, or preventing future or cumulative damage such as sunlight damage and skin aging.

Dermatological or cosmetic compositions for the treatment according to the invention are applied topically on the epidermis as ointment pomades, lotions, creams and gels, and on mucous membranes as water emulsions such as creams, lotions or gels. The cosmetic products may be produced using such a composition include products such as shaving cream, hand cream, shampoo, soap, conditioner, body cream, sun skin-protection, face cream, or body lotion. The ratio of components in the cosmetic composition according to this invention can be adjusted according to the intended application of the cosmetic composition.

Tissue Scaffolding

In another aspect, the invention provides a composition, said composition comprising (i) cells; and (ii) a cell scaffold material comprising at least one fiber of the invention.

In another aspect, the invention provides a method for the cultivation of cells, the method comprising:

providing a sample of cells to be cultured;

applying said sample to a cell scaffold material comprising at least one fiber of the invention; and maintaining said cell scaffold material having cells applied thereto under conditions suitable for cell culture.

In the context of the present invention, the terms "cultivation" of cells, "cell culture" are to be interpreted broadly, such that they encompass for example situations in which cells divide and/or proliferate, situations in which cells are maintained in a differentiated state with retention of at least one functional characteristic exhibited by the cell type when present in its natural environment, and situations in which stem cells are maintained in an undifferentiated state.

In some embodiments, the cultivation methods or cell composition may be performed in conditions comprising cell culture and/or media containing specific growth factors or extracellular matrix (ECM) components. In other embodiments, the cultivation or preparation methods may be performed in conditions comprising maintaining the cell scaffold material having cells applied thereto in a serum-free medium. The possibility to culture cells in a serum-free medium affords a cost-efficient and controlled alternative to the use of serum-containing media and/or media containing specific growth factors or extracellular matrix (ECM) components.

In some embodiments of the methods and cell compositions described herein, the cells are eukaryotic cells. In some embodiments of the methods and cell compositions described herein, the eukaryotic cells are mammalian cells, for example human cells. In other embodiments, the eukaryotic cells are non-mammalian cells, such as insect or yeast cells.

Non-limiting examples of mammalian cells that may be cultivated or prepared by the methods or included in the cell composition according to the invention. In some embodiments, said cells are hepatocytes, fibroblasts, keratinocytes and endothelial cells. In some embodiments, said cells are stem cells and cells from islets of Langerhans including beta cells. In some embodiments, said cells are progenitor cells selected from the group consisting of neural progenitor cells, mesenchymal progenitor cells and hematopoietic progenitor cells. In some embodiments, said cells are adult stem cells selected from the group consisting of hematopoietic, neural, mesenchymal, mammary, endothelial, epithelial and olfactory stem cells, in particular selected from the group consisting of hematopoietic, neural and mesenchymal stem cells.

In some embodiments, the compositions of the invention are used as a tissue adhesive. The "tissue adhesive (also designated as tissue sealant or tissue glue)", as used herein, allows to connect, particularly reconnect, tissue layers, e.g. at least two tissue layers, with each other. Particularly, the tissue adhesive can provide a close, especially form-fit, connection between tissue layers, or in the event that the tissue layers are distant from each other, the tissue adhesive can fill the gap between the tissue layers, replace the missing tissue layers and/or bridge the missing tissue layers.

Non-limiting examples of tissue that may be cultivated or prepared by the methods or using the cell composition according to the invention include connective tissue, muscle tissue, nervous tissue, epithelial tissue, and combinations thereof, e.g. multiple (different) tissues, or any organ, e.g. stomach, small intestine, large intestine, bowel, rectum, oesophagus, lung, spleen, brain, heart, kidney, liver, skin, glands such as lymph and thyroid glands, eye, or pancreas.

In some embodiments, the composition further comprises a cell-binding motif. In connection with the cultivation of certain cells in certain conditions, the presence of a cell-binding motif may improve or maintain cell viability. In some embodiments, the cell-binding motif is an oligopeptide coupled to the fiber of the invention via at least one peptide bond. For example, it may be coupled to the N-terminal or the C-terminal of the proteins within the fiber of the invention, or at any position within the amino acid sequence of the rest of the mixture of proteins described herein. With regard to the selection of oligopeptidic cell-binding motifs, the skilled person is aware of several alternatives. Said oligopeptide may for example comprise an amino acid sequence selected from the group consisting of RGD, RGE, IKVAV, YIGSR, EPDIM and NKDIL. RGD, IKVAV and YIGSR are general cell-binding motifs, whereas EPDIM and NKDIL are known as keratinocyte-specific motifs that may be particularly useful in the context of cultivation of keratinocytes. The coupling of an oligopeptide cell-binding motif to a protein within the fiber is readily accomplished by the skilled person using standard genetic engineering or chemical coupling techniques. Thus, in some embodiments, the cell-binding motif is introduced via genetic engineering, i.e. forming part of a genetic fusion between nucleic acid encoding the "wild-type" protein and the cell-binding motif.

In some embodiments, the cells in contact with the fibers of the invention are in a multi-layered form. A multi-layered cell culture or a 3D cell culture includes at least 2 layers of cells, such as that at least 10% of the cells in one layer are in contact with at least 10% of the cells in another layer. In some embodiments, a multi-layered cell culture or a 3D cell culture includes at least 3 layers of cells.

In some embodiments, at least 10% of the cells in one layer within a multi-layered cell culture or a 3D cell culture are in contact with at least 10% of the cells in another layer within the same multi-layered cell culture or 3D cell culture. In some embodiments, at least 20% of the cells in one layer within a multi-layered cell culture or a 3D cell culture are in contact with at least 20% of the cells in another layer within the same multi-layered cell culture or 3D cell culture. In some embodiments, at least 30% of the cells in one layer within a multi-layered cell culture or a 3D cell culture are in contact with at least 30% of the cells in another layer within the same multi-layered cell culture or 3D cell culture. In some embodiments, at least 40% of the cells in one layer within a multi-layered cell culture or a 3D cell culture are in contact with at least 40% of the cells in another layer within the same multi-layered cell culture or 3D cell culture. In some embodiments, at least 50% of the cells in one layer within a multi-layered cell culture or a 3D cell culture are in contact with at least 50% of the cells in another layer within the same multi-layered cell culture or 3D cell culture. In some embodiments, at least 60% of the cells in one layer within a multi-layered cell culture or a 3D cell culture are in contact with at least 60% of the cells in another layer within the same multi-layered cell culture or 3D cell culture. In another embodiment, the phrase "in contact" is in physical contact. In another embodiment, the phrase "in contact" is in cell to cell interaction.

In another embodiment, the phrase "3D culture (three dimensional culture)" refers to a culture in which the cells are disposed to conditions which are compatible with cell growth while allowing the cells to grow in more than one layer.

Articles

In a further aspect, the invention provides an article comprising of at least one fiber composed of a recombinant protein according to the invention.

The term "article" or "an article of manufacture" is includes manufactured items which are tangible, movable and independent objects. More specifically, herein the term "article" refers to such manufactured items which comprise or incorporate at least one of the amino acid sequence, the recombinant protein and the fiber of the invention. Non-limiting example of such articles include: synthetic spider-silk coated stents and sutures, dermal patches, tissue scaffold material, fabrics, vests, bullet-proof vests, ropes, threads, cosmetics, etc.

Examples of such articles are threads used for surgical sutures, or threads used for weaving garments or the articles may be scaffolds used for various tissue engineering aspects.

Other examples of articles according to the invention include medical devices such as medical adhesive strips, skin grafts, replacement ligaments, and surgical mesh; and in a wide range of industrial and commercial products, such as clothing fabric, bullet-proof vest lining, container fabric, bag or purse straps, cable, rope, fishing line, adhesive binding material, non-adhesive binding material, strapping material, automotive covers and parts, aircraft construction material, weatherproofing material, flexible partition material, sports equipment; and, in fact, in nearly any use of fiber or fabric for which high tensile strength and elasticity are desired characteristics. Adaptability and use of the stable fiber product in other forms, such as a dry spray coating, bead-like particles, or use in a mixture with other compositions is also contemplated by the present invention.

The recombinant spider silk proteins of the present invention may be added to cellulose and keratin and collagen products and thus, the present invention is also directed to a paper or a skin care and hair care product, comprising cellulose and/or keratin and/or collagen and the spider silk proteins of the present invention. Papers and skin care and hair care products, in which the proteins of the present invention are incorporated are showing improved characteristics, in particular improved tensile strength or tear strength.

Composites

The present invention provides, in some embodiments, composites comprising: (a) a mixture of proteins having a differing molecular weight useful for the preparation of synthetic dragline spider silk; and (b) a polymer.

In some embodiments, the term "composite" refers to a material which is composed of two or more substances having different characteristics and in which each substance retains its identity while contributing desirable properties to the whole.

In some embodiments, the term "material" refers to a solid material. In some embodiments, the term "material" refers to a semi-solid material (e.g., a gel).

In some embodiments, the disclosed composites exhibit superior mechanical properties.

In some embodiments, there is provided fiber comprising the mixture of proteins.

In some embodiments, a plurality of the fibers are attached to one another via the linker.

In some embodiments, the term "polymer", as used hereinthroughout, describes a substance, e.g., an organic substance, but alternatively an inorganic substance, composed of a plurality of repeating structural units (referred to interchangeably as backbone units or monomeric units) covalently connected to one another and forming the polymeric backbone of the polymer. The term "polymer" as used herein encompasses organic and inorganic polymers and further encompasses one or more of a homopolymer, a copolymer or a mixture thereof (e.g., a blend). The term "homopolymer" as used herein describes a polymer that is made up of one type of monomeric units and hence is composed of homogenic backbone units. The term "copolymer" as used herein describes a polymer that is made up of more than one type of monomeric units and hence is composed of heterogenic backbone units. The heterogenic backbone units can differ from one another by the pendant groups thereof.

For the sake of simplicity, the terms "polymer" and "polymeric backbone" as used hereinthroughout interchangeably, relate to both homopolymers, copolymers and mixtures thereof.

In some embodiments the polymer is hydrophobic. In some embodiments the polymer is UV cured.

In some embodiments, the disclosed composite is biostable. In some embodiments, the disclosed composite is biocleavable.

In some embodiments, the term "biostable" describes a compound or a polymer that remains intact under physiological conditions (e.g., is not degraded in vivo, and hence is non-biodegradable or non-biocleavable).

In some embodiments, the term "biodegradable" describes a substance which can decompose under physiological and/or environmental condition(s) into breakdown products. Such physiological and/or environmental conditions include, for example, hydrolysis (decomposition via hydrolytic cleavage), enzymatic catalysis (enzymatic degradation), and mechanical interactions. This term typically refers to substances that decompose under these conditions such that 50 weight percent of the substance decompose within a time period shorter than one year.

In some embodiments, the term "biodegradable" as used in the context of embodiments of the invention, also encompasses the term "bioresorbable", which describes a substance that decomposes under physiological conditions to break down products that undergo bioresorption into the host-organism, namely, become metabolites of the biochemical systems of the host-organism.

In some embodiments, the polymer is or comprises a synthetic polymer. In some embodiments, the polymer is or comprises a natural polymer. A natural polymer may refer to a polymer made of, without limitation, a natural source such as plants, animal and mineral sources, or can be woven from natural fibers such as cotton, linen, jute, flax, ramie, sisal and hemp, hair, and wool.

Further exemplary natural polymer comprises polylactide, collagen Keratin, cellulose, actine, myosine, chitin, *Bombyx mori* silk.

In some embodiments, the polymer is a thermoplastic polymer. In some embodiments, the polymer is a thermoset. In some embodiments, the polymer is an epoxy. In some embodiments, the polymer is polyester (e.g., aliphatic polyesters). In some embodiments, the polymer is selected from the group consisting of polyamides, polyurethane, and Nylons. In some embodiments, the polymer is a cross-linked polymer. In some embodiments, the polymer is copolymer. In some embodiments, the polymer is in the form of a hydrogel.

In some embodiments, the polymeric materials are two or more component-materials (e.g., copolymer). As demonstrated in the Example section that follows, component (also referred to as "part") A may be the main (base) polymer, and part B may be e.g., a hardener or a catalyst.

Hardener chemical families vary with the polymer base, but includes amines, isocyanates, peroxides and few others.

Copolymer may be produced by a mechanism selected from radical polymerization process (e.g., using Azobisisobutyronitrile (abbreviated AIBN)), a step-growth polymerization and a chain growth polymerization.

The term "epoxy", as used herein, refers to a reactive group which is a three membered heterocyclic molecule with one oxygen and two methylene groups, having a molecular formula of —$C_2H_3O$.

Production Methods

In some embodiments, there is provided a method for producing the protein mixture of the invention. In specific embodiments, the method of the invention comprises the steps of:

a. providing an expression vector comprising a nucleic acid sequence encoding said amino acid sequence, wherein said nucleic acid is under expression control of operably linked promoter and, optionally, regulatory sequences;

b. transforming a host cell with the expression vector of (a);

c. providing conditions for expression of heterologous proteins by the host cell of (b); and d. isolating the expressed proteins, thereby obtaining the synthetic amino acid sequences of the invention.

It is appreciated that while the invention generally relates to synthetic spider silk proteins or any fragments or parts thereof derived from *Araneus diadematus* dragline silk, many other spider species may be used to derive synthetic spider silk in a similar manner. More preferably, the dragline proteins are derived from one or more of the following spiders: *Arachnura higginsi, Araneus circulissparsus, Araneus diadematus, Argiope picta*, Banded Garden Spider (*Argiope trifasciata*), Batik Golden Web Spider (*Nephila antipodiana*), Beccari's Tent Spider (*Cyrtophora beccarii*), Bird-dropping Spider (*Celaenia excavata*), Black-and-White Spiny Spider (*Gasteracantha kuhlii*), Black-and-yellow Garden Spider (*Argiope aurantia*), Bolas Spider (*Ordgarius furcatus*), Bolas Spiders Magnificent Spider (*Ordgarius magnificus*), Brown Sailor Spider (*Neoscona nautica*), Brown-Legged Spider (*Neoscona rufofemorata*), Capped Black-Headed Spider (*Zygiella calyptrata*), Common Garden Spider (*Parawixia dehaani*), Common Orb Weaver (*Neoscona oxancensis*), Crab-like Spiny Orb Weaver (*Gasteracantha cancriformis* (elipsoides)), Curved Spiny Spider (*Gasteracantha arcuata*), *Cyrtophora moluccensis, Cyrtophora parnasia, Dolophones conifera, Dolophones turrigera*, Doria's Spiny Spider (*Gasteracantha doriae*), Double-Spotted Spiny Spider (*Gasteracantha mammosa*), Double-Tailed Tent Spider (*Cyrtophora exanthematica*), *Aculeperia ceropegia, Eriophora pustulosa*, Flat Anepsion (*Anepsion depressium*), Four-spined Jewel Spider (*Gasteracantha quadrispinosa*), Garden Orb Web Spider (*Eriophora transmarina*), Giant Lichen Orbweaver (*Araneus bicentenarius*), Golden Web Spider (*Nephila maculata*), Hasselt's Spiny Spider (*Gasteracantha hasseltii*), *Tegenaria atrica, Heurodes turrita*, Island Cyclosa Spider (*Cyclosa insulana*), Jewel or Spiny Spider (*Astracantha minax*), Kidney Garden Spider (*Araneus mitificus*), Laglaise's Garden Spider (*Eriovixia laglaisei*), Long-Bellied Cyclosa Spider (*Cyclosa bifida*), Malabar Spider (*Nephilengys malabarensis*), Multi-Coloured St Andrew's Cross Spider (*Argiope versicolor*), Ornamental Tree-Trunk Spider (*Herennia ornatissima*), Oval St. Andrew's Cross Spider (*Argiope aemula*), Red Tent Spider (*Cyrtophora unicolor*), Russian Tent Spider (*Cyrtophora hirta*), Saint Andrew's Cross Spider (*Argiope keyserlingi*), Scarlet Acusilas (*Acusilas coccineus*), Silver Argiope (*Argiope argentata*), Spinybacked Orbweaver (*Gasteracantha cancriformis*), Spotted Orbweaver (*Neoscona domiciliorum*), St. Andrews Cross (*Argiope aetheria*), St. Andrew's Cross Spider (*Argiope Keyserlingi*), Tree-Stump Spider (*Poltys illepidus*), Triangular Spider (*Arkys clavatus*), Triangular Spider (*Arkys lancearius*), Two-spined Spider (*Poecilopachys australasia*), *Nephila* species, e.g. *Nephila clavipes, Nephila senegalensis, Nephila madagascariensis* and many more.

Furthermore, the synthetic spider silk may be enhanced not only by selection of a different spider species to be derived from, but also by the use of various compounds other than protein. Pyrrolidine has hygroscopic properties and helps to keep the thread moist. It occurs in especially high concentration in glue threads. Potassium hydrogen phosphate releases protons in aqueous solution, resulting in a pH of about 4, making the silk acidic and thus protecting it from fungi and bacteria that would otherwise digest the protein. Potassium nitrate is believed to prevent the protein from denaturing in the acidic milieu.

As used herein the term "about" refers to ±10%.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments. The word "optionally" is used herein to mean "is provided in some embodiments and not provided in other embodiments". Any particular embodiment of the invention may include a plurality of "optional" features unless such features conflict.

As used herein and in the appended claims, the singular forms "a," "and," and "the" include plural referents unless the context clearly dictates otherwise. Thus, for example, reference to "MaSp" includes a plurality of such genes and variants and reference to "the peptide" includes reference to one or more peptides known to those skilled in the art, and so forth.

Also, the use of "or" means "and/or" unless stated otherwise. Similarly, "comprise," "comprises," "comprising" "include," "includes," and "including" are interchangeable and not intended to be limiting. It is to be further understood that where descriptions of various embodiments use the term "comprising," those skilled in the art would understand that in some specific instances, an embodiment can be alternatively described using language "consisting essentially of" or "consisting of."

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

EXAMPLES

Materials and Methods

Plasmids:

DNA sequence in a PCR-ScriptAmpSK(+) plasmid obtained from Geneart (Regensburg, Germany). pFastBacHTa obtained from Invitrogen.

Restriction Enzymes:

PstI, HindIII, NsiI, obtained from (New England Biolabs, MA, USA).

Transfection and Transformation:

Competent *E. coli* DH10BAC cells, containing bacmid and a helper plasmid were from Invitrogen. ESCORT transfection reagent obtained from Sigma-Aldrich.

Media:

ESF 921 Insect cell culture medium, Protein free, obtained from Expression Systems.

Cells:

SF9—*Spodoptera frugiperda* insect cells grown in suspension (ATCC#: CRL-1711).

Antibodies:

Mouse anti-His6 monoclonal antibody obtained from Roche. Texas Red conjugated anti-mouse secondary IgG obtained from Jackson laboratories.

Dyes:

NanoVan (Nanoprobes, NY, USA).

Imaging:

Olympus BX51 fluorescence microscope. Magnafire SP camera was from Optronics.

Experimental Procedures

Synthesis of a Sequence Encoding for a Single Repeat Unit of a Dragline Spider Silk Protein:

A 35 amino acid long sequence representing an average consensus sequence of the 15 repeats constituting the repetitive region of ADF-4 (Genbank entry U47856) was designed. The average consensus sequence peptide sequence is: SGPGGYGPGSQGPSGPGGYGPGGPGS-SAAAAAAAA (SEQ ID NO 14), which is encoded by the 105 DNA base pair sequence: 5'-TCTGGTCCTGGAGGT-TATGGCCCAGGAAGCCAAGGACCATCTGGTCCAG-GAGGATATGGTCCAGGCGGACCTGGCTCTAGTG CAGCAGCTGCCGCAGCAGCTGCA-3' (SEQ ID NO: 15). The above synthetic DNA was obtained in a PCR-ScriptAmpSK(+) plasmid. The sequence was optimized for expression according to the codon usage of *Spodoptera frugiperda*, cells of which are used for the synthesis of the spider silk proteins and fibers.

In certain experiments, three constructs having varying amino acid sequences were performed, each having a unique amino acid sequence:

C1 (SEQ ID NO: 35 and 36): SGPG-GYGPGSQGPSGPGGYGPGGPGSSAGAGAGAXaaA (Xaa depicting either Ala or Gly)

C2 (SEQ ID NO: 38 and 40): XaaGSGPG-GYGPGGQGPGGYGPGGQGPYGPGAAAAAAA (Xaa depicting either Ser or Gly)

C3 (SEQ ID NO: 42 and 44): XaaGPGQG-GYGGPGGQGPGRGGYGPGAGSAAAAAAAAA (Xaa depicting either Ser or Gly).

The polynucleotide sequence encoding a single repeat of the three (C1-C3) constructs are provided as SEQ ID NO: 45-47, respectively.

Donor Plasmid Construction:

The ScriptAmpSK(+) plasmid was excised with Xba I and Xho I, and a 136-bp sequence containing the basic repeat sequence flanked with Nsi I and Pst I restriction sites was isolated and cloned into the multiple cloning site (MCS) of the baculoviral donor plasmid pFastBacHTa. Thus, the basic donor plasmid coding for an artificial 49 amino acid N-terminal domain and a 35 amino acid core domain was generated.

Multimerization of the Single Repeat:

The basic module coding for one repeat (monomer) of spider silk protein is flanked by the restriction enzymes sites NsiI and PstI, which are compatible. In the first step the monomer is released by double restriction and is inserted in frame into the same donor plasmid cut with PstI. Only if the insert is ligated in the correct sense orientation will a double cut release a dimer (the restriction site between the two repeats was eliminated upon ligation). In a second step the dimer was released and then reinserted in the same fashion to obtain a vector with four repeats. In following steps, this procedure was reiterated to obtain a donor plasmid containing multiple synthetic repeats. Constraints resulting from the molecular biology tools employed and the repetitive nature of the sequence limit the maximum achievable number of identical repeats.

Ligation of the Native C-Terminal Domain Downstream to the Synthetic Repeats:

Insertion of the C-terminal domain of ADF4 114 amino acids took place using PCR with the following primers: A sense primer having the sequence 5'-ATATG CTGCAGGCCCTAGTGGTCCTGGA-3' (SEQ ID NO: 16) containing a PstI restriction site (underlined) and an antisense primer having the sequence 5'-TCGAC AAGCTTGGTACCGCA-3' (SEQ ID NO: 17) coding for a 3' HindIII restriction site (underlined). The donor plasmid vectors with different number of repeats and the PCR product were excised with PstI and HindIII, purified and ligated, resulting in a pFastBacHTa donor plasmid coding for a His6 tag which is part of an artificial N terminal domain, followed by a varied number of identical repeats (the inventors obtained constructs containing 1, 2, 4, 8, 12, 16, 20, 24, 32 repeats of the nucleic acid sequence) and the native C terminal domain.

Cell Culture:

Sf9 cells were propagated at 27° C. in ESF 921 serum-free insect cell culture medium. Sf9 cells were grown either as monolayers on cover slips in 6 well plates or in shaker flasks agitated at 130 rpm.

Production of Recombinant Baculovirus:

Competent *E. coli* DH10BAC cells, containing bacmid (baculovirus shuttle vector plasmid) and a helper plasmid, were used to generate recombinant bacmids according to the manufacturer's protocol (Invitrogen). Insertion of the gene into the bacmid was verified by PCR. Sf9 cells were transfected with recombinant bacmid DNA using ESCORT transfection reagent in 6-well plates. The cells were incubated for 5 h at 27° C., rinsed and incubated for another 72 h. Media were harvested, centrifuged, and the virus containing supernatant was used for 2-3 successive infections resulting in amplification of the virion titer.

Expression of Synthetic ADF-4 Based Proteins:

Sf9 cells ($3*10^6$ cells/ml) were infected with the recombinant viruses at various MOIs (multiplicity of infection) ranging from 0.1 to 10. Four days post infection cells were harvested by centrifugation at 16000 g for 10 min.

Purification of Synthetic Fibers:

Infected cells were harvested 4 days post infection and centrifuged for 10 min at 16000 g. Cell pellet was resuspended in a 0.25% SDS solution, incubated at R.T for 30 min and protein assemblies were sedimented as above. Typical yields of purified fibers were about 150 mg/L of Sf9 insect cell culture. Purified fibers were resuspended at desired solution and volume.

Differential Scanning Calorimeter (DSC) Measurement:

Thermal analysis was performed on 3-6 mg fibroin samples using a Mettler DSC 822e thermo analyzer and an aluminum sample pan under an inert nitrogen atmosphere. The thermo grams ranged from 10 C.° to 400 C.° at 5 C.°/min heating rate.

Immunocytochemistry:

Cells grown on cover slips at 50% confluency were infected with recombinant viruses at MOI=10. Three days post infection cells were fixed with methanol at −20° C. Cover slips were incubated with mouse anti-His6 monoclonal antibody at a 1:300 dilution followed by Texas Red conjugated anti-mouse secondary IgG at 1:500 dilutions. Cells were observed with an Olympus BX51 fluorescence microscope and images were taken with a Magnafire SP camera or analyzed by confocal microscopy.

Transmission Electron Microscopy (TEM):

For ultra-structural analysis, purified filaments were adsorbed onto 300 mesh copper holey carbon grids, as is, or negatively stained with vanadium (NanoVan1, Nanoprobes), viewed and photographed by a Tecnai T12 microscope, operated at 120 kV.

Example 1

Characterization of Nano-Fibers Composing the Micro-Fiber

Figure 1C:
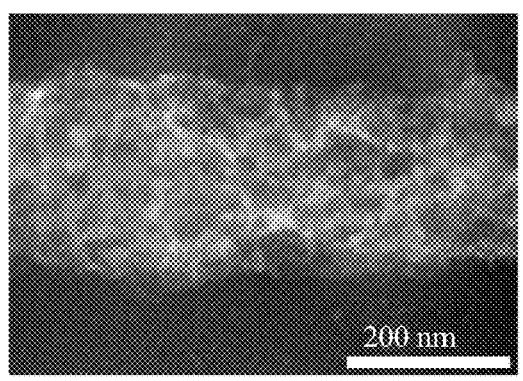
Figure 1D:
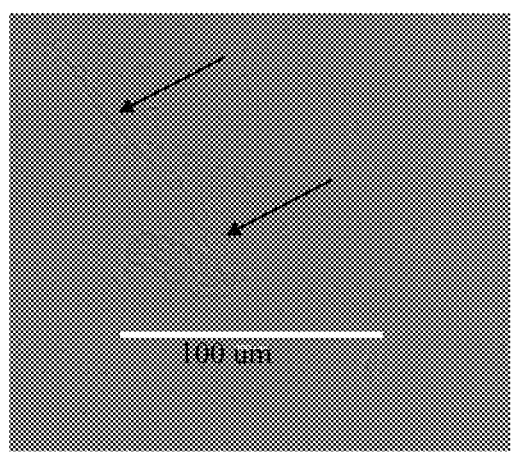
Figure 1E:
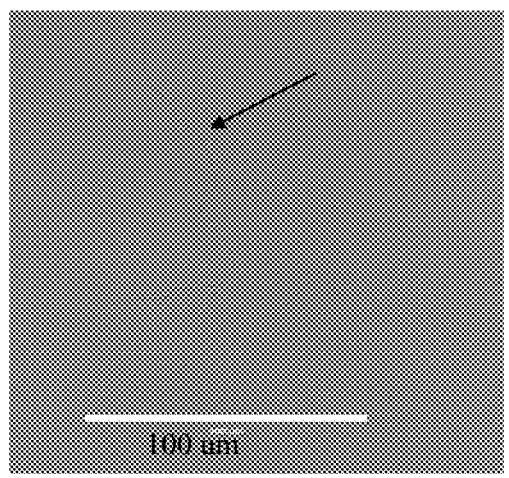
Figure 1F:
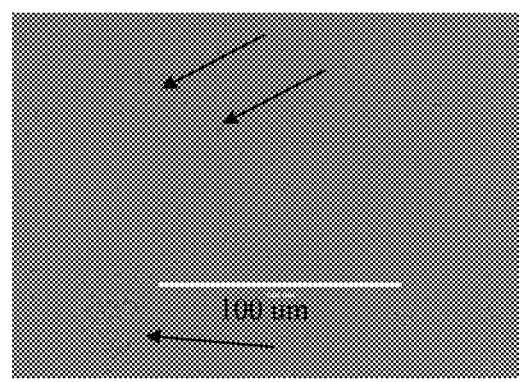
Figure 1G:
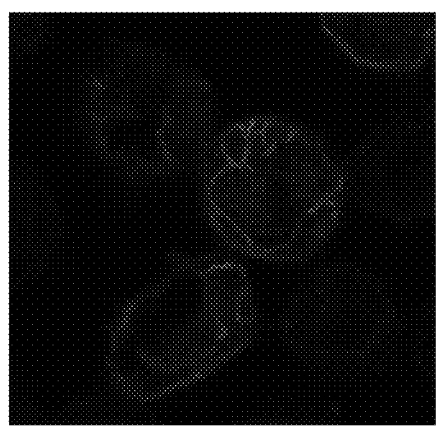
Figure 1H:
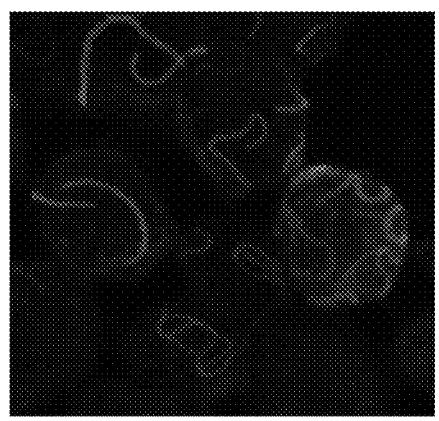
Figure 1I:
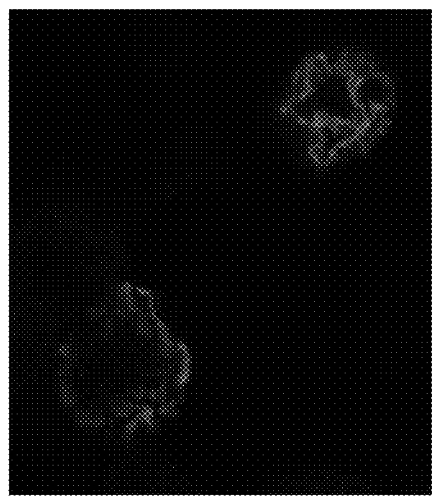

Gold particles (Ni-NTA-Nanoprobes), having a diameter of 1.8 nanometer, were bound to the N-terminal $His_6$ tag of each of the monomers of the instant invention. An immune-TEM observation revealed a two-step assembly process in which the monomers first interact with each other in a head to tail fashion, thus creating a nano-fibril with a diameter of approximately five nanometer as a first stage (FIG. 1A). Consequently, the nano-fibrils interact with each other in a non-oriented fashion (FIG. 1B), thus creating a fiber with a diameter of approximately 150 nanometer (FIG. 1C).

Further, the phenotypes of the various assembled fibers based on three independent constructs (C1, C2 and C3) were examined using light microscopy and fluorescent labeled fibers using confocal microscopy. As shown in FIGS. 1D-I, the monomers of construct C1 self-assembled to create a coiled fiber inside the expressing cell cytosol. The diameter of this fiber ranged between 100 to 200 nm, and the length ranged between 10 to 150 µm. The monomers of construct C2 self-assembled to create fibers having a diameter ranging between 100 to 200 nm, while their length ranges between 10 to 50 µm. The monomers of construct C3 self-assembled to various phenotypes: (i) Globular aggregates with an average diameter of 1 µm; (ii) Fibers covered with aggregates with an average diameter of 500 nm; (iii) Fibers with a smooth surface, similar to constructs C1 and C2.

Example 2

A Unique Laddering Phenomenon Characterizes the Fibers of the Invention

The monomers containing varying number of repeats (0, 1, 2, 3, 4, 8, 12, 16, 20, 24, 32) flanked by non-repetitive N-terminal and C-terminal domains tend to self-assemble and become insoluble. Therefore, in order to determine the molecular weight (MW) of the monomers, the fibers were purified and disassembled with 6M Guanidine SCN. Sequentially, the Guanidine solution was dialyzed against 8M Urea (using pierce dialysis cassette with MW cutoff of 10 KDa), sample buffer was added and the sample was analyzed in a denaturing 10% acryl amid gel.

Coomassie blue staining was performed on disassembled fibers from three different sources:

(1) Ladder of bands from gene composed of N-terminal domain, 24 identical repeats (2.7 KDa), C-terminal domain;

(2) Ladder of bands from gene composed of N-terminal domain, 16 identical repeats (2.7 KDa), C-terminal domain; and (3) Ladder of bands from gene composed of N-terminal domain, 15 non identical repeats (taken from the native sequence of *Araneus Diadematus*), C-terminal domain.

Figure 2A:
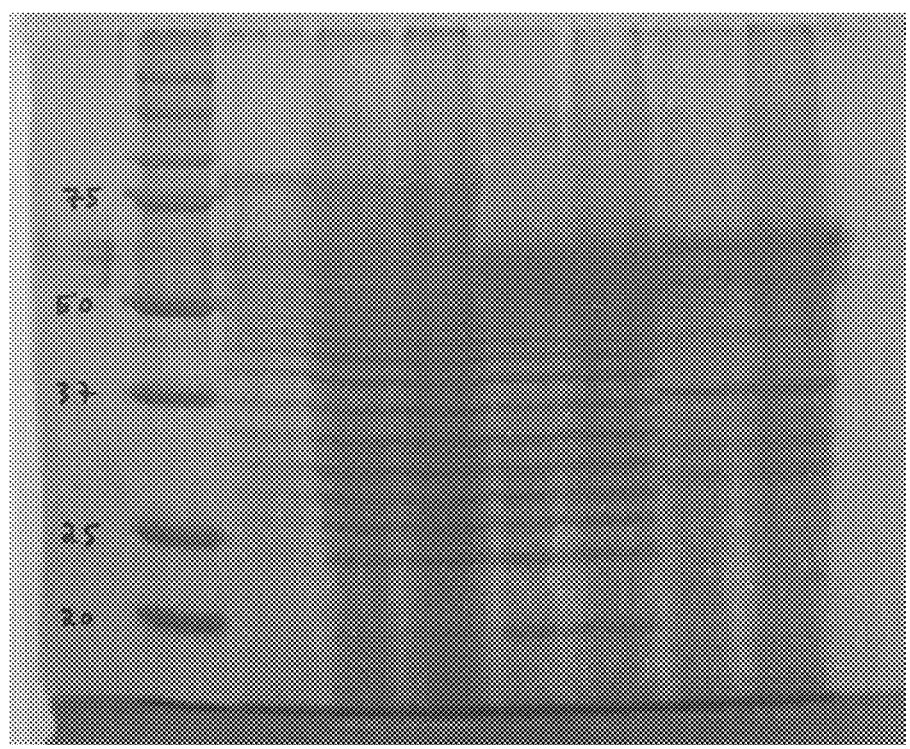
FIGS. 2A-C illustrate a laddering pattern of the protein repetitive unites using Coomassie blue staining and Western blot analysis.

As can be observed (FIG. 2A), while in the artificial constructs case (1, 2) there is a constant gradient related to the molar ratio of the different bands which favors the lighter versions of the bands, it is not the case at the ladder of the native sequence (3). For instance, the band that correlates to 38 KDa at the ladder originated from the native sequence is much more dense than the surrounding bands (above and beneath).

This observation strongly indicates a the importance of the source of the different repetitive zones. While at the artificial sequence case the repeats are identical, at the native sequence case the repeats differ by at least their overall size and poly-Alanine stretch length. Furthermore, the described difference correlate to the different assembly properties, different thermal stability and different mechanical properties that exist between fibers originated from the native repetitive sequence and the ones originated from the artificial repetitive sequences disclosed herein.

SDS-PAGE and Western Blotting Analysis:

As described above, Sf9 cells were transfected with constructs of Bacmid DNA and harvested 72 h post transfection.

Cell pellets were separated by SDS-PAGE using 10% gel and transferred to nitrocellulose by semi-dry blotting. Blocking was performed for one hour with milk powder in PBS×1, 0.5% Tween20. The membrane was incubated with mouse anti-His6 monoclonal antibody (1:2000) and goat anti mouse HRP conjugated (1:5000) as a secondary antibody. ECL was used to directly detect HIS-tagged constructs.

Figures 2B, 2C:
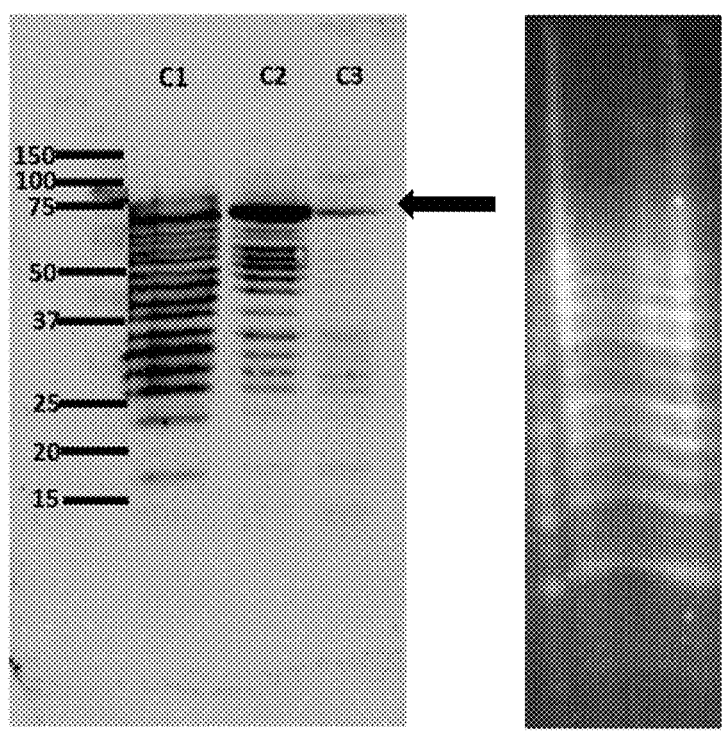

Western blot using primary antibody against the N-terminal $His_6$ tag verified the presence of the N-terminal domain in each of the observed bands (FIG. 2B). All three proteins (depicted as C1, C2 and C3) gave rise to the laddering phenomenon. All three protein's strongest band (depicted by an arrow) corresponds to the calculated M·W of the proteins originated from construct 1, 2 and 3 (61.41, 62.84, and 62.16 KDa respectively)

A fluorophore binding specifically to Cysteine (only one cysteine exist in our protein, located at the C-terminal domain) by disulfide bond was employed to verify the presence of the C-terminal domain at all of the observed bands of the ladder (FIG. 2C).

Northern blot of mRNA extracted from Sf9 cells infected with a baculovirus coding for the full length proteins under the polyhedrin promoter revealed an mRNA of a size correlating to the full length protein size. The extracted mRNA was next used as a template for RT-PCR, resulting in cDNA which in turn served as template to PCR resulting a ladder of DNA bands. Sequencing of isolated DNA bands from the above described ladder was performed using primers with complement sequence to the first and last 18 bases of the full sequence of the full protein. The sequencing revealed the presence of varying number of repeats flanked by the full N and C-terminal domains sequence.

The above findings taken together with the RNA secondary structure led to the surprising discovery of a novel protein synthesis control in which the repeats area at the mRNA adopts a hairpin structure, while the ribosome slips over this hairpin. As a result of the alternating size of this hairpin an array of proteins is synthesized by one mRNA. These proteins differ from one another only by the number of the repeats they contain, thus enabling the female spider to express an array of fibroin monomers based on one gene.

Example 3

Dissolved Purified Fibers can be Electrospun into a Continuous Fiber

Synthetic fibers isolated from SF9 infected cells, were dehydrated (under conditions of 55 degrees Celsius (C), overnight). Hexafluoro-2-propanol (HFIP) was added to the dry fibers to a final concentration of 23% Weight/Volume of dope. An electrospinning protocol was performed as follows: injection rate: 0.5 ml/hour, voltage: 18 kiloVolt, distance between the end of the nozzle and the collector: 16 centimeters, humidity: 40%, temperature: 28° C.

Figure 3A:
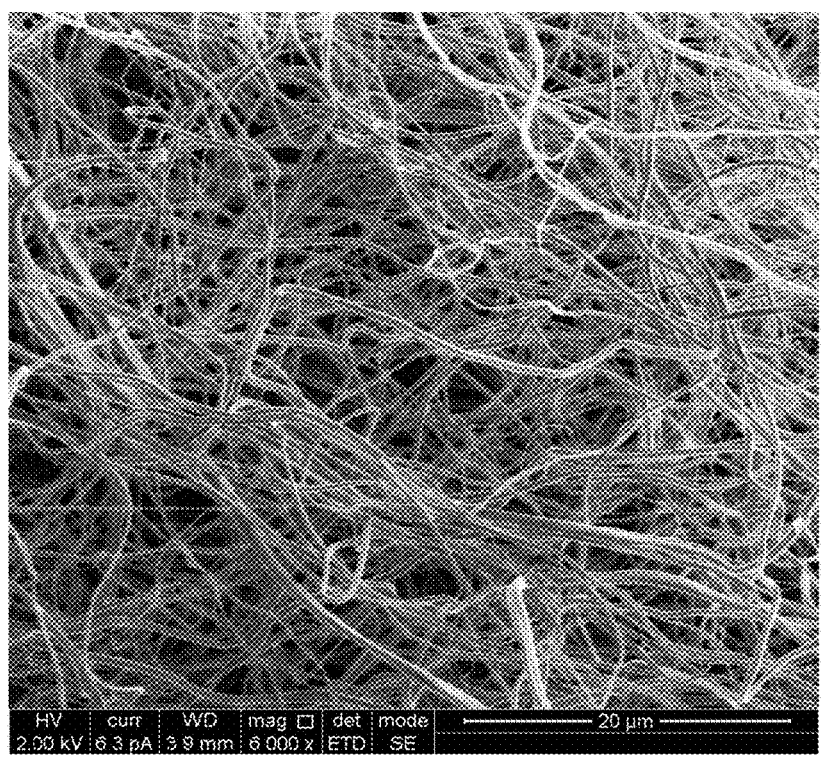
FIGS. 3A-B are a high resolution scanning electron microscopy (HR-SEM) (3A) and differential scanning calorimetry (DSC) (3B) of an electrospun fiber.
Figure 3B:
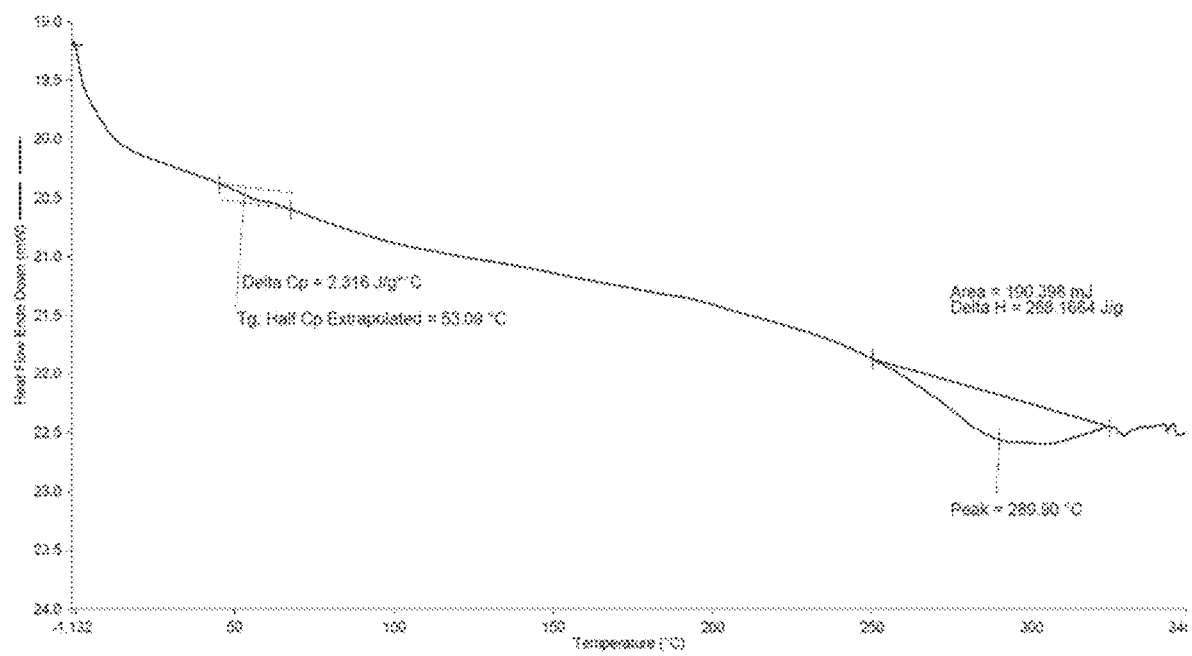

The above protocol resulted in a mesh of continuous fiber with an average diameter of 100 nanometer (FIG. 3A). DSC examination of this fiber revealed an endothermic peak at 289° C., indicating the presence of the nanocrystals based on the poly alanine stretches as in the synthetic fiber (FIG. 3B).

Example 4

Lyophilization of Purified Fibers and Linear Characterization

Figure 4A:
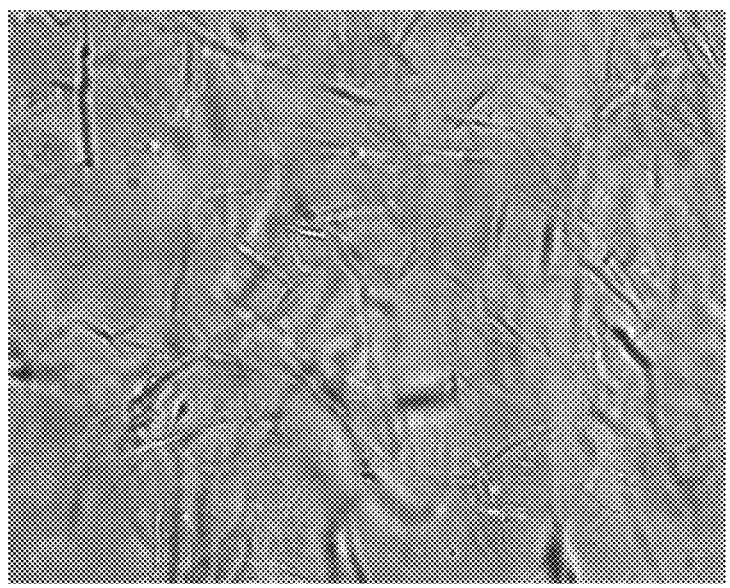
FIGS. 4A-B show lyophilized fibers embedded in a transparent matrice (4A) and a corresponding DSC curve (4B).

Purified fibers were suspended in double-distilled water (DDW) at 0.5% weight/volume, frozen by liquid nitrogen (in a temperature of −200° C.) followed by lyophilization for approximately 24 hours. The above procedure resulted in a white powder containing dry fibers. Deeper examination of these fibers revealed that they were linearized, keeping their diameter and were easily dispersed at a variety of matrices while adopting a linear structure (FIG. 4A) as well as preserving their mechanical properties.

Figure 4B:
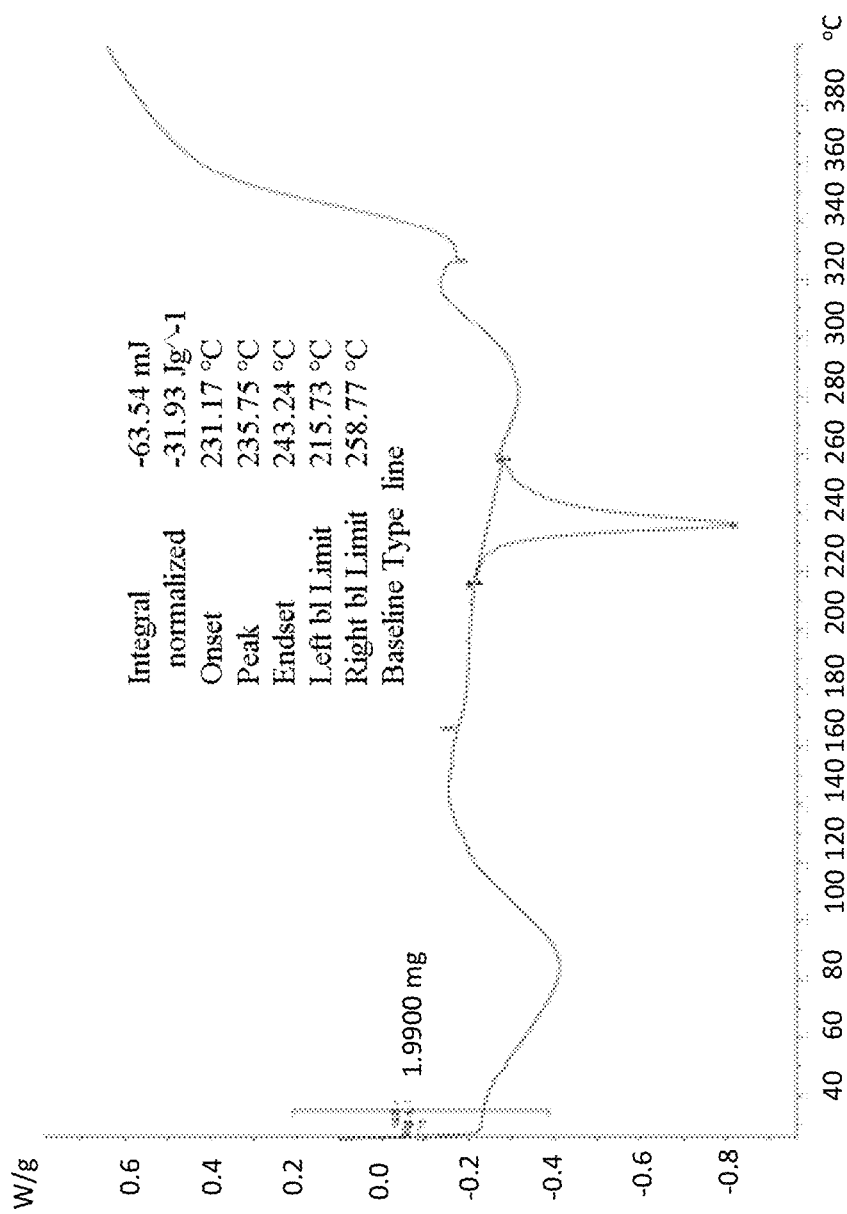

Notably, in comparison to the native dragline melting point (230° C.), the melting point of the synthetic fiber disclosed herein was measured to be hight at about 235° C. (FIG. 4B).

Example 5

Multi-Layered Cell Growth on the Fibers of the Invention

Fibers of the invention (1:25 in PBS) were added to wells of a sterile 96-well tissue culture plate. Following incubation (at 4° C.) and washing steps, HEK293 cells were plated into each fiber-coated well, followed by an incubation step (72 h at 37° C., 5% $CO_2$).

As seen in FIGS. 5A-C, HEK 293 cells were found to preferably adhere to the fibers of the invention rather to the tissue culture plate. Further, the fibers of the invention altered cell preference from layer growth to 3D growth.

Example 6

Thermal Fingerprint of the Fibers of the Invention

Several tests were conducted to characterize the thermal fingerprint of the fibers of the invention.

Fibers were weighed at 5-10 mg per test. Each test was performed on a pierced aluminum pan, volume 40 μL on a Mettler-Toledo DSC 2 system equipped with a liquid nitrogen cooling tank. The test was run from 25-350° C. at a 5° C./min heating rate after a water removal process of heating to 100° C. and maintaining that temperature for 5 min.

The results show that, unexpectedly, the thermal finger print showed a peak starting at 265±5° C. until 320±5° C. with a peak at ~300° C.

Additional tests showed a thermal finger print having 3 peaks:

1. Exothermic peak at −120-160° C.;
2. Endothermic peak at 230-260° C.;
3. Decomposition peak at 265±5° C. until 320±5° C.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

SEQUENCE LISTING

```
<160> NUMBER OF SEQ ID NOS: 47

<210> SEQ ID NO 1
<211> LENGTH: 28
<212> TYPE: PRT
<213> ORGANISM: artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: X is A or G
<220> FEATURE:
<221> NAME/KEY: MISC_FEATURE
<222> LOCATION: (2)..(2)
<223> OTHER INFORMATION: X is S or G
<220> FEATURE:
<221> NAME/KEY: MISC_FEATURE
<222> LOCATION: (10)..(10)
<223> OTHER INFORMATION: X is G or E
<220> FEATURE:
<221> NAME/KEY: MISC_FEATURE
<222> LOCATION: (11)..(11)
<223> OTHER INFORMATION: X is G, S or N
<220> FEATURE:
<221> NAME/KEY: MISC_FEATURE
<222> LOCATION: (12)..(12)
<223> OTHER INFORMATION: X is Q or Y
<220> FEATURE:
<221> NAME/KEY: MISC_FEATURE
<222> LOCATION: (15)..(15)
<223> OTHER INFORMATION: X is G or S
<220> FEATURE:
<221> NAME/KEY: MISC_FEATURE
<222> LOCATION: (17)..(17)
<223> OTHER INFORMATION: X is P or R
<220> FEATURE:
<221> NAME/KEY: MISC_FEATURE
<222> LOCATION: (20)..(20)
<223> OTHER INFORMATION: X is Y or Q
<220> FEATURE:
<221> NAME/KEY: MISC_FEATURE
<222> LOCATION: (27)..(27)
<223> OTHER INFORMATION: X is G or S
<220> FEATURE:
<221> NAME/KEY: MISC_FEATURE
<222> LOCATION: (28)..(28)
<223> OTHER INFORMATION: X is S or G

<400> SEQUENCE: 1

Xaa Xaa Gly Pro Gly Gly Tyr Gly Pro Xaa Xaa Xaa Gly Pro Xaa Gly
1               5                   10                  15

Xaa Gly Gly Xaa Gly Pro Gly Gly Pro Gly Xaa Xaa
            20                  25
```

```
<210> SEQ ID NO 2
<211> LENGTH: 27
<212> TYPE: PRT
<213> ORGANISM: artificial
<220> FEATURE:
<223> OTHER INFORMATION: synthetic

<400> SEQUENCE: 2

Ser Gly Pro Gly Gly Tyr Gly Pro Gly Ser Gln Pro Ser Gly Pro
1               5                   10                  15

Gly Gly Tyr Gly Pro Gly Gly Pro Gly Ser Ser
                20                  25

<210> SEQ ID NO 3
<211> LENGTH: 35
<212> TYPE: PRT
<213> ORGANISM: artificial
<220> FEATURE:
<223> OTHER INFORMATION: synthetic

<400> SEQUENCE: 3

Ala Ala Ala Ala Ala Ala Ala Ala Ser Gly Pro Gly Gly Tyr Gly Pro
1               5                   10                  15

Gly Ser Gln Gly Pro Ser Gly Pro Gly Gly Tyr Gly Pro Gly Gly Pro
                20                  25                  30

Gly Ser Ser
        35

<210> SEQ ID NO 4
<211> LENGTH: 35
<212> TYPE: PRT
<213> ORGANISM: artificial
<220> FEATURE:
<223> OTHER INFORMATION: synthetic

<400> SEQUENCE: 4

Ala Ala Ala Ala Ala Ala Ala Ala Ser Gly Pro Gly Gly Tyr Gly Pro
1               5                   10                  15

Glu Asn Gln Gly Pro Ser Gly Pro Gly Gly Tyr Gly Pro Gly Gly Pro
                20                  25                  30

Gly Ser Ser
        35

<210> SEQ ID NO 5
<211> LENGTH: 40
<212> TYPE: PRT
<213> ORGANISM: artificial
<220> FEATURE:
<223> OTHER INFORMATION: synthetic

<400> SEQUENCE: 5

Met Ser Tyr Tyr His His His His His His Asp Tyr Asp Ile Pro Thr
1               5                   10                  15

Thr Glu Asn Leu Tyr Phe Gln Gly Ala Met Asp Pro Glu Phe Lys Gly
                20                  25                  30

Leu Arg Arg Arg Ala Gln Leu Val
        35                  40

<210> SEQ ID NO 6
<211> LENGTH: 49
<212> TYPE: PRT
<213> ORGANISM: artificial
<220> FEATURE:
<223> OTHER INFORMATION: synthetic
```

<400> SEQUENCE: 6

Met Ser Tyr Tyr His His His His His Asp Tyr Asp Ile Pro Thr
1               5                   10                  15

Thr Glu Asn Leu Tyr Phe Gln Gly Ala Met Asp Pro Glu Phe Lys Gly
            20                  25                  30

Leu Arg Arg Arg Ala Gln Leu Val Arg Pro Leu Ser Asn Leu Asp Asn
        35                  40                  45

Ala

<210> SEQ ID NO 7
<211> LENGTH: 54
<212> TYPE: PRT
<213> ORGANISM: artificial
<220> FEATURE:
<223> OTHER INFORMATION: synthetic

<400> SEQUENCE: 7

Met Ser Tyr Tyr His His His His His Asp Tyr Asp Ile Pro Thr
1               5                   10                  15

Thr Glu Asn Leu Tyr Phe Gln Gly Ala Met Asp Pro Glu Phe Lys Gly
            20                  25                  30

Leu Arg Arg Arg Ala Gln Leu Val Asp Pro Pro Gly Cys Arg Asn Ser
        35                  40                  45

Ala Arg Ala Gly Ser Ser
        50

<210> SEQ ID NO 8
<211> LENGTH: 28
<212> TYPE: PRT
<213> ORGANISM: artificial
<220> FEATURE:
<223> OTHER INFORMATION: synthetic
<220> FEATURE:
<221> NAME/KEY: MISC_FEATURE
<222> LOCATION: (1)..(1)
<223> OTHER INFORMATION: X is A or G
<220> FEATURE:
<221> NAME/KEY: MISC_FEATURE
<222> LOCATION: (2)..(2)
<223> OTHER INFORMATION: X is S or G
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: X is S or G
<220> FEATURE:
<221> NAME/KEY: MISC_FEATURE
<222> LOCATION: (12)..(12)
<223> OTHER INFORMATION: X is Q or Y
<220> FEATURE:
<221> NAME/KEY: MISC_FEATURE
<222> LOCATION: (15)..(15)
<223> OTHER INFORMATION: X is S or G
<220> FEATURE:
<221> NAME/KEY: MISC_FEATURE
<222> LOCATION: (17)..(17)
<223> OTHER INFORMATION: X is P or R
<220> FEATURE:
<221> NAME/KEY: MISC_FEATURE
<222> LOCATION: (20)..(20)
<223> OTHER INFORMATION: X is Y or Q
<220> FEATURE:
<221> NAME/KEY: MISC_FEATURE
<222> LOCATION: (27)..(27)
<223> OTHER INFORMATION: X is G or S

```
<220> FEATURE:
<221> NAME/KEY: MISC_FEATURE
<222> LOCATION: (28)..(28)
<223> OTHER INFORMATION: X is G or S

<400> SEQUENCE: 8

Xaa Xaa Gly Pro Gly Gly Tyr Gly Pro Xaa Xaa Xaa Gly Pro Xaa Gly
1               5                   10                  15

Xaa Gly Gly Xaa Gly Pro Gly Gly Pro Gly Xaa Xaa
            20                  25

<210> SEQ ID NO 9
<211> LENGTH: 114
<212> TYPE: PRT
<213> ORGANISM: artificial
<220> FEATURE:
<223> OTHER INFORMATION: synthetic

<400> SEQUENCE: 9

Gly Pro Ser Gly Pro Gly Ala Tyr Gly Pro Ser Pro Ser Ala Ser Ala
1               5                   10                  15

Ser Val Ala Ala Ser Arg Leu Ser Ser Pro Ala Ala Ser Ser Arg Val
            20                  25                  30

Ser Ser Ala Val Ser Ser Leu Val Ser Ser Gly Pro Thr Asn Gly Ala
        35                  40                  45

Ala Val Ser Gly Ala Leu Asn Ser Leu Val Ser Gln Ile Ser Ala Ser
    50                  55                  60

Asn Pro Gly Leu Ser Gly Cys Asp Ala Leu Val Gln Ala Leu Leu Glu
65                  70                  75                  80

Leu Val Ser Ala Leu Val Ala Ile Leu Ser Ser Ala Ser Ile Gly Gln
                85                  90                  95

Val Asn Val Ser Ser Val Ser Gln Ser Thr Gln Met Ile Ser Gln Ala
            100                 105                 110

Leu Ser

<210> SEQ ID NO 10
<211> LENGTH: 555
<212> TYPE: PRT
<213> ORGANISM: artificial
<220> FEATURE:
<223> OTHER INFORMATION: synthetic

<400> SEQUENCE: 10

Ala Ala Ala Ala Ala Ala Ser Gly Ser Gly Gly Tyr Gly Pro Glu
1               5                   10                  15

Asn Gln Gly Pro Ser Gly Pro Val Ala Tyr Gly Pro Gly Gly Pro Val
            20                  25                  30

Ser Ser Ala Ala Ala Ala Ala Gly Ser Gly Pro Gly Gly Tyr
        35                  40                  45

Gly Pro Glu Asn Gln Gly Pro Ser Gly Pro Gly Gly Tyr Gly Pro Gly
    50                  55                  60

Gly Ser Gly Ser Ser Ala Ala Ala Ala Ala Ala Ser Gly Pro
65                  70                  75                  80

Gly Gly Tyr Gly Pro Gly Ser Gln Gly Pro Ser Gly Pro Gly Gly Ser
                85                  90                  95

Gly Gly Tyr Gly Pro Gly Ser Gln Gly Pro Ser Gly Pro Gly Ala Ser
            100                 105                 110

Ser Ala Ala Ala Ala Ala Ala Ala Ser Gly Pro Gly Gly Tyr Gly
        115                 120                 125
```

```
Pro Gly Ser Gln Gly Pro Ser Gly Pro Gly Ala Tyr Gly Pro Gly Gly
        130                 135                 140

Pro Gly Ser Ser Ala Ala Ala Ser Gly Pro Gly Gly Tyr Gly Pro Gly
145                 150                 155                 160

Ser Gln Gly Pro Ser Gly Pro Gly Gly Ser Gly Gly Tyr Gly Pro Gly
                165                 170                 175

Ser Gln Gly Pro Ser Gly Pro Gly Gly Pro Gly Ala Ser Ala Ala Ala
                180                 185                 190

Ala Ala Ala Ala Ala Ala Ser Gly Pro Gly Gly Tyr Gly Pro Gly Ser
        195                 200                 205

Gln Gly Pro Ser Gly Pro Gly Ala Tyr Gly Pro Gly Gly Pro Gly Ser
210                 215                 220

Ser Ala Ala Ala Ser Gly Pro Gly Gly Tyr Gly Pro Gly Ser Gln Gly
225                 230                 235                 240

Pro Ser Gly Pro Gly Ala Tyr Gly Pro Gly Gly Pro Gly Ser Ser Ala
            245                 250                 255

Ala Ala Ala Ala Ala Ala Gly Ser Gly Pro Gly Gly Tyr Gly Pro Gly
        260                 265                 270

Asn Gln Gly Pro Ser Gly Pro Gly Gly Tyr Gly Pro Gly Gly Pro Gly
        275                 280                 285

Ser Ser Ala Ala Ala Ala Ala Ala Ser Gly Pro Gly Gly Tyr Gly
290                 295                 300

Pro Gly Ser Gln Gly Pro Ser Gly Pro Gly Val Tyr Gly Pro Gly Gly
305                 310                 315                 320

Pro Gly Ser Ser Ala Ala Ala Ala Ala Gly Ser Gly Pro Gly
            325                 330                 335

Gly Tyr Gly Pro Gly Asn Gln Gly Pro Ser Gly Pro Gly Gly Tyr Gly
            340                 345                 350

Pro Gly Gly Ser Gly Ser Ser Ala Ala Ala Ala Ala Ala Ala Ala Ser
            355                 360                 365

Gly Pro Gly Gly Tyr Gly Pro Gly Ser Gln Gly Pro Ser Gly Pro Gly
        370                 375                 380

Gly Ser Gly Gly Tyr Gly Pro Gly Ser Gln Gly Pro Ser Gly Pro Gly
385                 390                 395                 400

Ala Ser Ser Ala Ala Ala Ala Ala Ala Ser Gly Pro Gly Gly
            405                 410                 415

Tyr Gly Pro Gly Ser Gln Gly Pro Ser Gly Pro Gly Ala Tyr Gly Pro
            420                 425                 430

Gly Gly Pro Gly Ser Ser Ala Ala Ala Ser Gly Pro Gly Gly Tyr Gly
        435                 440                 445

Pro Gly Ser Gln Gly Pro Ser Gly Pro Gly Ala Tyr Gly Pro Gly Gly
        450                 455                 460

Pro Gly Ser Ser Ala Ala Ala Ala Ala Ala Ser Gly Pro Gly Gly
465                 470                 475                 480

Tyr Gly Pro Gly Ser Gln Gly Pro Ser Gly Pro Gly Gly Ser Arg Gly
                485                 490                 495

Tyr Gly Pro Gly Ser Gln Gly Pro Gly Gly Pro Gly Ala Ser Ala Ala
                500                 505                 510

Ala Ala Ala Ala Ala Ala Ser Gly Pro Gly Gly Tyr Gly Pro Gly
        515                 520                 525

Ser Gln Gly Pro Ser Gly Pro Gly Tyr Gln Gly Pro Ser Gly Pro Gly
530                 535                 540
```

Ala Tyr Gly Pro Ser Pro Ser Ala Ser Ala Ser
545                 550             555

<210> SEQ ID NO 11
<211> LENGTH: 6
<212> TYPE: PRT
<213> ORGANISM: artificial
<220> FEATURE:
<223> OTHER INFORMATION: synthetic

<400> SEQUENCE: 11

His His His His His His
1               5

<210> SEQ ID NO 12
<211> LENGTH: 9
<212> TYPE: PRT
<213> ORGANISM: artificial
<220> FEATURE:
<223> OTHER INFORMATION: synthetic

<400> SEQUENCE: 12

Tyr Pro Tyr Asp Val Pro Asp Tyr Ala
1               5

<210> SEQ ID NO 13
<211> LENGTH: 11
<212> TYPE: PRT
<213> ORGANISM: artificial
<220> FEATURE:
<223> OTHER INFORMATION: synthetic

<400> SEQUENCE: 13

Met Ala Ser Met Thr Gly Gly Gln Gln Met Gly
1               5                   10

<210> SEQ ID NO 14
<211> LENGTH: 35
<212> TYPE: PRT
<213> ORGANISM: artificial
<220> FEATURE:
<223> OTHER INFORMATION: synthetic

<400> SEQUENCE: 14

Ser Gly Pro Gly Gly Tyr Gly Pro Gly Ser Gln Gly Pro Ser Gly Pro
1               5                   10                  15

Gly Gly Tyr Gly Pro Gly Gly Pro Gly Ser Ser Ala Ala Ala Ala Ala
            20                  25                  30

Ala Ala Ala
        35

<210> SEQ ID NO 15
<211> LENGTH: 105
<212> TYPE: DNA
<213> ORGANISM: Artificial
<220> FEATURE:
<223> OTHER INFORMATION: Synthetic

<400> SEQUENCE: 15
tctggtcctg gaggttatgg cccaggaagc caaggaccat ctggtccagg aggatatggt    60
ccaggcggac ctggctctag tgcagcagct gccgcagcag ctgca                  105

<210> SEQ ID NO 16
<211> LENGTH: 28
<212> TYPE: DNA

-continued

<213> ORGANISM: Artificial
<220> FEATURE:
<223> OTHER INFORMATION: Synthetic

<400> SEQUENCE: 16
atatgctgca ggccctagtg gtcctgga                                          28

<210> SEQ ID NO 17
<211> LENGTH: 20
<212> TYPE: DNA
<213> ORGANISM: Artificial
<220> FEATURE:
<223> OTHER INFORMATION: Synthetic

<400> SEQUENCE: 17
tcgacaagct tggtaccgca                                                   20

<210> SEQ ID NO 18
<211> LENGTH: 266
<212> TYPE: PRT
<213> ORGANISM: artificial
<220> FEATURE:
<223> OTHER INFORMATION: synthetic

<400> SEQUENCE: 18

Gly Ser Ala Met Gly Tyr Leu Trp Ile Gln Gly Gln Gly Tyr Gly
1               5                   10                  15

Gly Leu Gly Gln Gly Gly Tyr Gly Gln Gly Ala Gly Ser Ser Ala Ala
            20                  25                  30

Ala Ala Ala Ala Ala Ala Ala Ala Ala Gly Gly Gln Gly Gly Gln
        35                  40                  45

Gly Gln Gly Gly Tyr Gly Gln Gly Ser Gly Ser Ala Ala Ala Ala
    50                  55                  60

Ala Ala Ala Ala Ala Ala Ala Ala Ala Gly Arg Gly Gln Gly
65                  70                  75                  80

Gly Tyr Gly Gln Gly Ser Gly Gly Asn Ala Ala Ala Ala Ala Ala
                85                  90                  95

Ala Ala Ala Ala Ala Ala Ala Gly Gln Gly Gly Gln Gly Gly Tyr
            100                 105                 110

Gly Arg Gln Ser Gln Gly Ala Gly Ser Ala Ala Ala Ala Ala Ala
        115                 120                 125

Ala Ala Ala Ala Ala Ala Ala Gly Ser Gly Gln Gly Gly Tyr Gly Gly
    130                 135                 140

Gln Gly Gln Gly Gly Tyr Gly Gln Ser Ser Ala Ser Ala Ser Ala Ala
145                 150                 155                 160

Ala Ser Ala Ala Ser Thr Val Ala Asn Ser Val Ser Arg Leu Ser Ser
                165                 170                 175

Pro Ser Ala Val Ser Arg Val Ser Ser Ala Val Ser Ser Leu Val Ser
            180                 185                 190

Asn Gly Gln Val Asn Met Ala Ala Leu Pro Asn Ile Ile Ser Asn Ile
        195                 200                 205

Ser Ser Ser Val Ser Ala Ser Ala Pro Gly Cys Glu Val Ile Val Gln
    210                 215                 220

Ala Leu Leu Glu Val Ile Thr Ala Leu Val Gln Ile Val Ser Ser Ser
225                 230                 235                 240

Ser Val Gly Tyr Ile Asn Pro Ser Ala Val Asn Gln Ile Thr Asn Val
                245                 250                 255

Val Ala Asn Ala Met Ala Gln Val Met Gly

```
                260                 265

<210> SEQ ID NO 19
<211> LENGTH: 257
<212> TYPE: PRT
<213> ORGANISM: artificial
<220> FEATURE:
<223> OTHER INFORMATION: synthetic

<400> SEQUENCE: 19

Gly Ser Ala Met Ala Ser Gly Gln Gly Gly Gln Gly Gly Gln Gly Gln
1               5                   10                  15

Gly Gly Tyr Gly Gln Gly Ala Gly Ile Ser Ala Ala Ala Ala Ala Ala
            20                  25                  30

Ala Ala Ala Ala Ala Gly Ala Ala Gly Arg Gly Gln Gly Gly Tyr
        35                  40                  45

Gly Gln Gly Ala Gly Gly Asn Ala Ala Ala Ala Ala Ala Ala Ala
    50                  55                  60

Ala Ala Ala Ala Gly Gln Gly Gly Gln Gly Gly Tyr Gly Gly Gln
65                  70                  75                  80

Gly Leu Gly Gly Tyr Gly Gln Gly Ala Gly Ser Ser Ala Ala Ala Ala
                85                  90                  95

Ala Ala Ala Ala Gly Arg Gly Gln Ser Val Tyr Ala Ser Gly Gly Ala
            100                 105                 110

Gly Gln Gly Gly Tyr Gly Gly Leu Gly Gly Gln Gly Ala Gly Arg Gly
        115                 120                 125

Gly Gln Gly Ala Gly Ala Ala Ala Ala Ala Gly Gly Ser Gly Gln
    130                 135                 140

Gly Gly Tyr Gly Gly Val Gly Ser Gly Ala Ser Ala Ala Ser Ala Ala
145                 150                 155                 160

Ala Ser Arg Leu Ser Ser Pro Glu Ala Ser Ser Arg Val Ser Ser Ala
                165                 170                 175

Val Ser Asn Leu Val Ser Ser Gly Pro Thr Asn Ser Ala Ala Leu Ser
            180                 185                 190

Ser Thr Ile Ser Asn Val Val Ser Gln Ile Gly Ala Ser Asn Pro Gly
        195                 200                 205

Leu Ser Gly Cys Asp Val Leu Val Gln Ala Leu Leu Glu Val Val Ser
    210                 215                 220

Ala Leu Ile His Ile Leu Gly Ser Ser Ser Ile Gly Gln Val Asn Tyr
225                 230                 235                 240

Gly Ser Ala Gly Gln Ala Thr Gln Leu Val Gly Gln Ser Val Tyr Gln
                245                 250                 255

Ala

<210> SEQ ID NO 20
<211> LENGTH: 276
<212> TYPE: PRT
<213> ORGANISM: artificial
<220> FEATURE:
<223> OTHER INFORMATION: synthetic

<400> SEQUENCE: 20

Gly Ser Ala Met Gly Gln Gly Ser Gly Gly Asn Ala Ala Ala Ala Ala
1               5                   10                  15

Ala Ala Ala Ala Ala Ala Ala Ala Ser Gly Gln Gly Gly Gln Gly Gly
            20                  25                  30

Gln Gly Gln Gly Gly Tyr Gly Gln Gly Ala Gly Ile Ser Ala Ala Ala
```

-continued

```
                35                   40                  45
Ala Ala Ala Ala Ala Ala Ala Gly Ala Ala Gly Arg Gly Gln
             50                  55                  60
Gly Gly Tyr Gly Gln Gly Ala Gly Asn Ala Ala Ala Ala Ala
65                  70                  75                  80
Ala Ala Ala Ala Ala Ala Ala Gly Gln Gly Gln Gly Gly Tyr
                 85                  90                  95
Gly Gly Gln Gly Leu Gly Gly Tyr Gly Gln Ala Gly Ser Ser Ala
                100                 105                 110
Ala Ala Ala Ala Ala Ala Gly Arg Gly Gln Ser Val Tyr Ala Ser
             115                 120                 125
Gly Gly Ala Gly Gln Gly Gly Tyr Gly Gly Leu Gly Gly Gln Gly Ala
             130                 135                 140
Gly Arg Gly Gly Gln Gly Ala Gly Ala Ala Ala Ala Ala Gly Gly
145                 150                 155                 160
Ser Gly Gln Gly Gly Tyr Gly Gly Val Gly Ser Gly Ala Ser Ala Ala
                165                 170                 175
Ser Ala Ala Ala Ser Arg Leu Ser Ser Pro Glu Ala Ser Ser Arg Val
             180                 185                 190
Ser Ser Ala Val Ser Asn Leu Val Ser Ser Gly Pro Thr Asn Ser Ala
             195                 200                 205
Ala Leu Ser Ser Thr Ile Ser Asn Val Val Ser Gln Ile Gly Ala Ser
             210                 215                 220
Asn Pro Gly Leu Ser Gly Cys Asp Val Leu Val Gln Ala Leu Leu Glu
225                 230                 235                 240
Val Val Ser Ala Leu Ile His Ile Leu Gly Ser Ser Ile Gly Gln
                245                 250                 255
Val Asn Tyr Gly Ser Ala Gly Gln Ala Thr Gln Leu Val Gly Gln Ser
             260                 265                 270
Val Tyr Gln Ala
         275

<210> SEQ ID NO 21
<211> LENGTH: 269
<212> TYPE: PRT
<213> ORGANISM: artificial
<220> FEATURE:
<223> OTHER INFORMATION: synthetic

<400> SEQUENCE: 21

Gly Ser Ala Met Gly Tyr Leu Trp Ile Gln Gly Gln Gly Gly Tyr Gly
1               5                   10                  15
Gly Leu Gly Gln Gly Gly Tyr Gly Gln Gly Ala Gly Ser Ser Ala Ala
                20                  25                  30
Ala Ala Ala Cys Cys Ala Ala Ala Ala Gly Gly Gln Gly Gly Gln
             35                  40                  45
Gly Gln Gly Gly Tyr Gly Gln Gly Ser Gly Gly Ser Ala Ala Ala Ala
         50                  55                  60
Ala Ala Ala Ala Ala Ala Ala Ala Ala Gly Arg Gly Gln Gly
65                  70                  75                  80
Gly Tyr Gly Gln Gly Ser Gly Asn Ala Ala Ala Ala Ala Ala
                 85                  90                  95
Ala Ala Ala Ala Ala Ala Ala Gly Gln Gly Gly Gln Gly Gly Tyr
                100                 105                 110
Gly Arg Gln Ser Gln Gly Ala Gly Ser Ala Ala Ala Ala Ala Ala
```

```
            115                 120                 125
Ala Ala Ala Ala Ala Ala Gly Ser Gly Gln Gly Gly Tyr Gly Gly
        130                 135                 140
Gln Gly Gln Gly Gly Tyr Gly Gln Ser Ser Ala Ser Ala Ser Ala Ala
145                 150                 155                 160
Ala Ser Ala Ala Ser Thr Val Ala Asn Ser Val Ser Arg Leu Ser Ser
                165                 170                 175
Pro Ser Ala Val Ser Arg Val Ser Ser Ala Val Ser Ser Leu Val Ser
                180                 185                 190
Asn Gly Gln Val Asn Met Ala Ala Leu Pro Asn Ile Ile Ser Asn Ile
                195                 200                 205
Ser Ser Ser Val Ser Ala Ser Ala Pro Gly Ala Ser Gly Cys Glu Val
        210                 215                 220
Ile Val Gln Ala Leu Leu Glu Val Ile Thr Ala Leu Val Gln Ile Val
225                 230                 235                 240
Ser Ser Ser Ser Val Gly Tyr Ile Asn Pro Ser Ala Val Asn Gln Ile
                245                 250                 255
Thr Asn Val Val Ala Asn Ala Met Ala Gln Val Met Gly
                260                 265

<210> SEQ ID NO 22
<211> LENGTH: 269
<212> TYPE: PRT
<213> ORGANISM: artificial
<220> FEATURE:
<223> OTHER INFORMATION: synthetic

<400> SEQUENCE: 22

Gly Ser Ala Met Gly Tyr Leu Trp Ile Gln Gly Gln Gly Gly Tyr Gly
1               5                   10                  15
Gly Leu Gly Gln Gly Gly Tyr Gly Gln Gly Ala Gly Ser Ser Ala Ala
                20                  25                  30
Ala Ala Ala Ala Ala Ala Ala Ala Ala Gly Gly Gln Gly Gly Gln
        35                  40                  45
Gly Gln Gly Gly Tyr Gly Gln Gly Ser Gly Gly Ser Ala Ala Ala Ala
50                  55                  60
Ala Ala Ala Ala Ala Ala Ala Ala Ala Gly Arg Gly Gln Gly
65                  70                  75                  80
Gly Tyr Gly Gln Gly Ser Gly Gly Asn Ala Ala Ala Ala Ala Ala
                85                  90                  95
Ala Ala Ala Ala Ala Ala Gly Gln Gly Gly Gln Gly Gly Tyr
                100                 105                 110
Gly Arg Gln Ser Gln Gly Ala Gly Ser Ala Ala Ala Ala Ala Cys
        115                 120                 125
Cys Ala Ala Ala Ala Ala Gly Ser Gly Gln Gly Gly Tyr Gly Gly
        130                 135                 140
Gln Gly Gln Gly Gly Tyr Gly Gln Ser Ser Ala Ser Ala Ser Ala Ala
145                 150                 155                 160
Ala Ser Ala Ala Ser Thr Val Ala Asn Ser Val Ser Arg Leu Ser Ser
                165                 170                 175
Pro Ser Ala Val Ser Arg Val Ser Ser Ala Val Ser Ser Leu Val Ser
                180                 185                 190
Asn Gly Gln Val Asn Met Ala Ala Leu Pro Asn Ile Ile Ser Asn Ile
                195                 200                 205
Ser Ser Ser Val Ser Ala Ser Ala Pro Gly Ala Ser Gly Cys Glu Val
```

```
            210                 215                 220
Ile Val Gln Ala Leu Leu Glu Val Ile Thr Ala Leu Val Gln Ile Val
225                 230                 235                 240

Ser Ser Ser Val Gly Tyr Ile Asn Pro Ser Ala Val Asn Gln Ile
                245                 250                 255

Thr Asn Val Val Ala Asn Ala Met Ala Gln Val Met Gly
            260                 265
```

<210> SEQ ID NO 23
<211> LENGTH: 217
<212> TYPE: PRT
<213> ORGANISM: artificial
<220> FEATURE:
<223> OTHER INFORMATION: synthetic

<400> SEQUENCE: 23

```
Gly Ser Ala Met Gly Tyr Leu Trp Ile Gln Gly Gln Gly Tyr Gly
1               5                   10                  15

Gly Leu Gly Gln Gly Gly Tyr Gly Gln Gly Ala Gly Ser Ser Ala Ala
                20                  25                  30

Ala Ala Ala Ala Ala Ala Ala Ala Ala Gly Gly Gln Gly Gln
            35                  40                  45

Gly Gln Gly Gly Tyr Gly Gln Gly Ser Gly Ala Ala Ala Ala Ala
50                  55                  60

Ala Ala Ala Ala Ala Ala Ala Ala Gly Arg Gly Gln Gly Gly Tyr
65                  70                  75                  80

Gly Gln Gly Ser Gly Gly Asn Ala Ala Ala Ala Ala Ala Ala Ala
                85                  90                  95

Ala Ala Ala Ala Ala Gly Gln Gly Gly Gln Gly Gly Tyr Gly Arg
            100                 105                 110

Gln Ser Gln Gly Ala Gly Ser Ala Ala Ala Ala Ala Ala Ala Ala
            115                 120                 125

Ala Ala Ala Ala Ala Gly Ser Gly Gln Gly Gly Tyr Gly Gln Gly
        130                 135                 140

Gln Gly Gly Tyr Gly Gln Ser Ser Ala Ser Ala Ser Ala Ala Ala Ser
145                 150                 155                 160

Ala Ala Ser Thr Val Ala Asn Ser Val Ser Arg Leu Ser Ser Pro Ser
                165                 170                 175

Ala Val Ser Arg Val Ser Ser Ala Val Ser Ser Leu Val Ser Asn Gly
                180                 185                 190

Gln Val Asn Met Ala Ala Leu Pro Asn Ile Ile Ser Val Asn Val Val
            195                 200                 205

Ala Asn Ala Met Ala Gln Val Met Gly
        210                 215
```

<210> SEQ ID NO 24
<211> LENGTH: 3129
<212> TYPE: PRT
<213> ORGANISM: artificial
<220> FEATURE:
<223> OTHER INFORMATION: synthetic

<400> SEQUENCE: 24

```
Met Thr Trp Ser Thr Arg Leu Ala Leu Ser Phe Leu Phe Val Leu Cys
1               5                   10                  15

Thr Gln Ser Leu Tyr Ala Leu Ala Gln Ala Asn Thr Pro Trp Ser Ser
                20                  25                  30
```

```
Lys Ala Asn Ala Asp Ala Phe Ile Asn Ser Phe Ile Ser Ala Ala Ser
             35              40              45

Asn Thr Gly Ser Phe Ser Gln Asp Gln Met Glu Asp Met Ser Leu Ile
 50              55              60

Gly Asn Thr Leu Met Ala Ala Met Asp Asn Met Gly Arg Ile Thr
 65              70              75              80

Pro Ser Lys Leu Gln Ala Leu Asp Met Ala Phe Ala Ser Ser Val Ala
             85              90              95

Glu Ile Ala Ala Ser Glu Gly Gly Asp Leu Gly Val Thr Thr Asn Ala
            100             105             110

Ile Ala Asp Ala Leu Thr Ser Ala Phe Tyr Gln Thr Thr Gly Val Val
            115             120             125

Asn Ser Arg Phe Ile Ser Glu Ile Arg Ser Leu Ile Gly Met Phe Ala
130             135             140

Gln Ala Ser Ala Asn Asp Val Tyr Ala Ser Ala Gly Ser Ser Gly Gly
145             150             155             160

Gly Gly Tyr Gly Ala Ser Ser Ala Ser Ala Ser Ala Ser Ala Ala
            165             170             175

Ala Pro Ser Gly Val Ala Tyr Gln Ala Pro Ala Gln Ala Gln Ile Ser
            180             185             190

Phe Thr Leu Arg Gly Gln Gln Pro Val Ser Tyr Gly Gln Gly Gly Ala
            195             200             205

Gly Pro Gly Gly Ala Gly Ala Ala Ala Ala Ala Ala Ala Gly
210             215             220

Gly Ala Gly Gln Gly Gly Gln Gly Gly Tyr Gly Gln Gly Gly Tyr Gly
225             230             235             240

Gln Gly Gly Ala Gly Gln Gly Gly Ser Gly Ala Ala Ala Ala Ala
            245             250             255

Ala Ala Ala Gly Gly Thr Gly Gln Gly Gly Ala Gly Gln Gly Gly Ala
            260             265             270

Gly Ala Ala Ala Ala Ala Ala Ala Gly Gly Ala Gly Gln Gly
            275             280             285

Gly Gln Gly Gly Tyr Gly Gln Gly Gly Tyr Gly Gln Gly Gly Thr Gly
            290             295             300

Gln Gly Gly Ala Gly Ala Ala Ala Ala Ala Ala Ala Gly Ala
305             310             315             320

Gly Gln Gly Gly Gln Gly Gly Tyr Gly Gln Gly Gly Tyr Gly Gln Gly
            325             330             335

Gly Tyr Gly Gln Gly Gly Ser Gly Ala Ala Ala Ala Ala Ala
            340             345             350

Ala Gly Gly Ala Gly Gln Gly Gly Gln Gly Gly Tyr Gly Gln Gly Gly
            355             360             365

Tyr Gly Gln Gly Gly Ala Gly Gln Gly Gly Ala Gly Ala Ala Ala
370             375             380

Ala Ala Ala Ala Ala Gly Gly Ala Gly Gln Gly Gly Tyr Gly Arg Gly
385             390             395             400

Gly Ala Gly Gln Gly Gly Ala Ala Ala Ala Ala Ala Ala Ala Gly
            405             410             415

Ala Gly Gln Gly Gly Tyr Gly Gly Gly Ala Gly Gln Gly Gly Ser
            420             425             430

Gly Ala Ala Ala Ala Ala Ala Ala Gly Gly Ala Gly Gln Gly Gly
            435             440             445

Gln Gly Gly Tyr Gly Gln Gly Gly Tyr Gly Gln Gly Gly Ser Gly Ala
```

```
              450                 455                 460
Ala Ala Ala Ala Ala Ala Gly Gly Ala Gly Gln Gly Gly Gln Gly
465                 470                 475                 480
Gly Tyr Gly Gln Gly Gly Tyr Gly Gln Gly Gly Ala Gly Gln Gly Gly
                    485                 490                 495
Ala Gly Ala Gly Ala Ala Ala Ala Ala Gly Gly Ala Gly Gln Gly
                500                 505                 510
Gly Gln Gly Gly Tyr Gly Gln Gly Gly Tyr Gly Gln Gly Gly Ala Gly
            515                 520                 525
Gln Gly Gly Ala Gly Ala Ala Ala Ala Ala Ala Ala Gly Gly Ala
            530                 535                 540
Gly Gln Gly Gly Gln Gly Gly Tyr Gly Gln Gly Gly Tyr Gly Gln Gly
545                 550                 555                 560
Gly Ala Gly Gln Gly Gly Ala Gly Ala Ala Ala Ala Ala Ala Ala
                565                 570                 575
Gly Gly Ala Gly Gln Gly Gly Gln Gly Gly Tyr Gly Gln Gly Gly Tyr
                580                 585                 590
Gly Gln Gly Gly Ala Gly Gln Gly Gly Ala Ala Ala Ala Ala Ala
                595                 600                 605
Ala Ala Gly Gly Ala Gly Gln Gly Gly Tyr Gly Arg Gly Gly Ala Gly
610                 615                 620
Gln Gly Gly Ala Ala Ala Ala Gly Ala Gly Gln Gly Gly Tyr Gly
625                 630                 635                 640
Gly Gln Gly Ala Gly Gln Gly Gly Ala Gly Ala Ala Ala Ala Ala
                645                 650                 655
Ala Ala Gly Gly Ala Gly Gln Gly Gly Gln Gly Gly Tyr Gly Arg Gly
                660                 665                 670
Gly Tyr Gly Gln Gly Gly Ala Gly Gln Gly Gly Ala Gly Ala Ala Ala
            675                 680                 685
Ala Ala Ala Ala Ala Gly Gly Ala Gly Gln Gly Gly Gln Gly Gly Tyr
690                 695                 700
Gly Gln Gly Gly Tyr Gly Gln Gly Gly Ala Gly Gln Gly Gly Ala Ala
705                 710                 715                 720
Ala Ala Ala Ala Ala Gly Gly Ala Gly Gln Gly Gly Tyr Gly Arg
                725                 730                 735
Gly Gly Ala Gly Gln Gly Gly Ala Ala Ala Ala Ala Ala Ala Ala
                740                 745                 750
Gly Ala Gly Gln Gly Gly Tyr Gly Gly Gln Gly Ala Gly Gln Gly Gly
            755                 760                 765
Ala Gly Ala Ala Ala Ala Ala Ala Ala Gly Gly Ala Gly Gln Gly
            770                 775                 780
Gly Gln Gly Asp Tyr Gly Arg Gly Gly Tyr Gly Gln Gly Gly Ala Gly
785                 790                 795                 800
Gln Gly Gly Ala Gly Ala Ala Ala Ala Ala Ala Ala Gly Gly Ala
                805                 810                 815
Gly Gln Gly Gly Gln Gly Gly Tyr Gly Gln Gly Gly Tyr Gly Gln Gly
                820                 825                 830
Gly Ala Gly Gln Gly Gly Ala Ala Ala Ala Ala Ser Ala Ala Ala
            835                 840                 845
Gly Gly Ala Gly Gln Gly Gly Tyr Gly Arg Gly Gly Ala Gly Gln Gly
            850                 855                 860
Gly Ala Ala Ala Ala Ala Gly Ala Gly Gln Gly Gly Tyr Gly Gly Gln
865                 870                 875                 880
```

```
Gly Ala Gly Gln Gly Gly Ala Gly Ala Ala Ala Ala Ala Ala
            885                 890                 895

Gly Gly Ala Gly Gln Gly Gly Gln Gly Gly Tyr Gly Arg Gly Gly Tyr
        900                 905                 910

Gly Gln Gly Gly Ala Gly Gln Gly Gly Ala Gly Ala Ala Ala Ala
        915                 920                 925

Thr Ala Ala Gly Ala Gly Gln Gly Gly Gln Gly Gly Tyr Gly Gln
    930                 935                 940

Gly Gly Tyr Gly Gln Gly Gly Ala Gln Gly Gly Ala Ala Ala Ala
945                 950                 955                 960

Ala Ala Ala Ala Ala Gly Gly Ala Gly Gln Gly Gly Tyr Gly Arg Gly
            965                 970                 975

Gly Ala Gly Gln Gly Gly Ala Ala Ala Ala Ala Ala Ala Ala Gly
        980                 985                 990

Ala Gly Gln Gly Gly Tyr Gly Gly Gln Gly Ala Gly Gln Gly Gly Ala
        995                 1000                1005

Gly Ala Ala Ala Ala Ala Ala Gly Gly Ala Gly Gln Gly Gly Gln
    1010                1015                1020

Gly Gly Tyr Gly Arg Gly Gly Tyr Gly Gln Gly Gly Ala Gly Gln
    1025                1030                1035

Gly Gly Ala Gly Ala Ala Ala Ala Ala Ala Ala Gly Gly Ala
    1040                1045                1050

Gly Gln Gly Gly Gln Gly Gly Tyr Gly Gln Gly Gly Tyr Gly Gln
    1055                1060                1065

Gly Gly Ala Gly Gln Gly Gly Ala Ala Ala Ala Ala Ala Ala
    1070                1075                1080

Ala Gly Gly Ala Gly Gln Gly Gly Tyr Gly Arg Gly Gly Ala Gly
    1085                1090                1095

Gln Gly Gly Ala Ala Ala Ala Gly Ala Gly Gln Gly Gly Tyr
    1100                1105                1110

Gly Gly Gln Gly Ala Gly Gln Gly Gly Ala Gly Ala Ala Ala Ala
    1115                1120                1125

Ala Ser Arg Gly Ala Gly Gln Gly Gly Gln Gly Gly Tyr Gly Arg
    1130                1135                1140

Gly Gly Tyr Gly Gln Gly Gly Ala Gly Gln Gly Gly Ala Gly Ala
    1145                1150                1155

Ala Ala Ala Ala Ala Ala Gly Gly Ala Gly Gln Gly Gly Gln
    1160                1165                1170

Gly Gly Tyr Gly Gln Gly Gly Tyr Gly Gln Gly Gly Ala Gly Gln
    1175                1180                1185

Gly Gly Ala Ala Ala Ala Ala Ala Ala Gly Gly Ala Gly Gln
    1190                1195                1200

Gly Gly Tyr Gly Arg Gly Gly Ala Gly Gln Gly Gly Ala Ala Ala
    1205                1210                1215

Ala Ala Gly Ala Gly Gln Gly Gly Tyr Gly Gly Gln Gly Ala Gly
    1220                1225                1230

Gln Gly Gly Ala Gly Ala Ala Ala Ala Ala Ala Ala Gly Gly
    1235                1240                1245

Ala Gly Gln Gly Gly Gln Gly Gly Tyr Gly Arg Gly Gly Tyr Gly
    1250                1255                1260

Gln Gly Gly Ala Gly Gln Gly Gly Ala Gly Ala Ala Ala Ala Ala
    1265                1270                1275
```

-continued

```
Ala Ala Ala Gly Gly Ala Gly Gln Gly Gly Gln Gly Gly Tyr Gly
    1280                1285                1290

Gln Gly Gly Tyr Gly Gln Gly Gly Ala Gly Gln Gly Gly Ala Ala
    1295                1300                1305

Ala Ala Ala Ala Ala Ala Ala Gly Gly Ala Gly Gln Gly Gly Tyr
    1310                1315                1320

Gly Arg Gly Gly Ala Gly Gln Gly Gly Ala Ala Ala Ala Ala Ala
    1325                1330                1335

Ala Ala Ala Gly Ser Gly Gln Gly Gly Tyr Gly Gly Gln Gly Ala
    1340                1345                1350

Gly Gln Gly Gly Ala Gly Ala Ala Ala Ala Ala Ala Ala Ala Gly
    1355                1360                1365

Gly Ala Gly Gln Gly Gly Gln Gly Gly Tyr Gly Arg Gly Gly Tyr
    1370                1375                1380

Gly Gln Gly Gly Ala Gly Gln Gly Gly Ala Gly Ala Ala Ala Ala
    1385                1390                1395

Ala Ala Ala Ala Gly Gly Ala Gly Gln Gly Gly Gln Gly Gly Tyr
    1400                1405                1410

Gly Gln Gly Gly Tyr Gly Gln Gly Gly Ala Gly Gln Gly Gly Ala
    1415                1420                1425

Ala Ala Ala Ala Ala Ala Ala Ala Gly Gly Ala Gly Gln Gly
    1430                1435                1440

Gly Tyr Gly Arg Gly Gly Ala Gly Gln Gly Gly Ala Ala Ala Ala
    1445                1450                1455

Ala Gly Ala Gly Gln Gly Gly Tyr Gly Gly Gln Gly Ala Gly Gln
    1460                1465                1470

Gly Gly Ala Gly Ala Ala Ala Ala Ala Ala Ala Ala Gly Gly Ala
    1475                1480                1485

Gly Gln Gly Gly Gln Gly Gly Tyr Gly Arg Gly Gly Tyr Gly Gln
    1490                1495                1500

Gly Gly Ala Gly Gln Gly Gly Ala Gly Thr Ala Ala Ala Ala Ala
    1505                1510                1515

Ala Ala Gly Gly Ala Gly Gln Gly Gly Gln Gly Gly Tyr Gly Gln
    1520                1525                1530

Gly Gly Tyr Gly Gln Gly Gly Ala Gly Gln Gly Gly Ala Ala Ala
    1535                1540                1545

Ala Ala Ala Ala Ala Ala Gly Gly Ala Gly Gln Gly Gly Tyr Gly
    1550                1555                1560

Arg Gly Gly Ala Gly Gln Gly Gly Ala Ala Ala Ala Ala Ala Ala
    1565                1570                1575

Ala Ala Gly Ala Gly Gln Gly Gly Tyr Gly Gly Gln Gly Ala Gly
    1580                1585                1590

Gln Gly Gly Ala Gly Ala Ala Ala Ala Ala Ala Ala Ala Gly Gly
    1595                1600                1605

Ala Gly Gln Gly Gly Gln Gly Gly Tyr Gly Arg Gly Gly Tyr Gly
    1610                1615                1620

Gln Gly Gly Ala Gly Gln Gly Gly Ala Gly Ala Ala Ala Ala Ala
    1625                1630                1635

Ala Ala Ala Gly Gly Ala Ser Gln Gly Gly Gln Gly Gly Tyr Gly
    1640                1645                1650

Gln Gly Asp Tyr Gly Gln Gly Gly Ala Gly Gln Gly Gly Ala Ala
    1655                1660                1665

Ala Ala Ala Ala Ala Ala Gly Gly Ala Gly Gln Gly Gly Tyr Gly
```

-continued

```
            1670                1675                1680
Arg Gly Gly Ala Gly Gln Gly Gly Ala Ala Ala Ala Gly Ala
        1685                1690                1695
Gly Gln Gly Gly Tyr Gly Gly Gln Gly Ala Gly Gln Gly Gly Ala
    1700                1705                1710
Gly Ala Ala Ala Ala Ala Ala Ala Ala Gly Gly Ala Gly Arg Gly
    1715                1720                1725
Gly Gln Gly Gly Tyr Gly Arg Gly Gly Tyr Gly Gln Gly Gly Ala
    1730                1735                1740
Gly Gln Gly Gly Ala Gly Ala Ala Ala Ala Ala Ala Ala Gly
    1745                1750                1755
Gly Ala Gly Gln Gly Gly Gln Gly Gly Tyr Gly Gln Gly Gly Tyr
    1760                1765                1770
Gly Gln Gly Gly Thr Gly Gln Gly Gly Ala Ala Ala Ala Ala
    1775                1780                1785
Ala Ala Ala Gly Gly Ala Gly Gln Gly Gly Tyr Gly Arg Gly Gly
    1790                1795                1800
Ala Gly Gln Gly Gly Ala Ala Ala Ala Ala Ala Ala Ala Gly
    1805                1810                1815
Ala Gly Gln Gly Gly Tyr Gly Gly Gln Gly Ala Gly Gln Gly Gly
    1820                1825                1830
Ala Gly Ala Ala Ala Ala Ala Ala Ala Gly Gly Ala Gly Gln
    1835                1840                1845
Gly Gly Gln Gly Gly Tyr Gly Arg Gly Gly Tyr Gly Gln Gly Gly
    1850                1855                1860
Ala Gly Gln Gly Gly Ala Gly Ala Ala Ala Ala Ala Ala Ala
    1865                1870                1875
Gly Gly Ala Gly Gln Gly Gly Gln Gly Gly Tyr Gly Gln Gly Gly
    1880                1885                1890
Tyr Gly Gln Gly Gly Tyr Gly Gln Gly Gly Ala Gly Gln Gly Gly
    1895                1900                1905
Ala Ala Ala Ala Ala Ala Ala Gly Gly Ala Gly Gln Gly Gly
    1910                1915                1920
Tyr Gly Arg Gly Gly Ala Gly Gln Gly Gly Ala Ala Ala Ala Ala
    1925                1930                1935
Gly Ala Gly Gln Gly Gly Tyr Gly Gly Gln Gly Ala Gly Gln Gly
    1940                1945                1950
Gly Ala Gly Ala Ala Ala Ala Ala Ala Ala Gly Gly Ala Gly
    1955                1960                1965
Gln Gly Gly Gln Gly Gly Tyr Gly Arg Gly Gly Tyr Gly Gln Gly
    1970                1975                1980
Gly Ala Gly Gln Gly Gly Ala Gly Ala Ala Ala Ala Ala Ala
    1985                1990                1995
Ala Gly Gly Ala Gly Gln Gly Gly Gln Gly Gly Tyr Gly Gln Gly
    2000                2005                2010
Gly Tyr Gly Gln Gly Gly Ala Gly Gln Gly Gly Ala Ala Ala Ala
    2015                2020                2025
Ala Ala Ala Ala Ala Gly Gly Ala Gly Gln Gly Gly Tyr Gly Arg
    2030                2035                2040
Gly Gly Ala Gly Gln Gly Gly Ala Ala Ala Ala Ala Ala Ala
    2045                2050                2055
Ala Gly Ser Gly Gln Gly Gly Tyr Gly Gly Gln Gly Ala Gly Gln
    2060                2065                2070
```

Gly Gly Ala Gly Ala Ala Ala Ala Ala Ala Gly Gly Ala
    2075            2080              2085

Gly Gln Gly Gly Gln Gly Gly Tyr Gly Arg Gly Gly Tyr Gly Gln
    2090            2095              2100

Gly Gly Ala Gly Gln Gly Gly Ala Gly Ala Ala Ala Ala Ala
    2105            2110              2115

Ala Ala Gly Gly Ala Gly Gln Gly Gly Gln Gly Gly Tyr Gly Gln
    2120            2125              2130

Gly Gly Tyr Gly Gln Gly Gly Tyr Gly Gln Gly Gly Ala Gly Gln
    2135            2140              2145

Gly Gly Ala Ala Ala Ala Ala Ala Ala Ala Ala Gly Gly Ala
    2150            2155              2160

Gly Gln Gly Gly Tyr Gly Arg Gly Gly Ala Gly Gln Gly Gly Ala
    2165            2170              2175

Ala Ala Ala Ala Gly Ala Gly Gln Gly Gly Tyr Gly Gly Gln Gly
    2180            2185              2190

Ala Gly Gln Gly Gly Ala Gly Ala Ala Ala Ala Ala Ala Ala
    2195            2200              2205

Gly Gly Ala Gly Gln Gly Gly Gln Gly Gly Tyr Gly Arg Gly Gly
    2210            2215              2220

Tyr Gly Gln Gly Gly Ala Gly Gln Gly Gly Ala Gly Ala Ala Ala
    2225            2230              2235

Ala Ala Ala Ala Ala Gly Gly Ala Gly Gln Gly Gly Gln Gly Gly
    2240            2245              2250

Tyr Gly Gln Gly Gly Asn Gly Gln Gly Gly Ala Gly Gln Gly Gly
    2255            2260              2265

Ala Ala Ala Ala Ala Ala Ala Ala Gly Gly Ala Gly Gln Gly Gly
    2270            2275              2280

Tyr Gly Arg Gly Gly Ala Gly Gln Gly Gly Ala Ala Ala Ala Ala
    2285            2290              2295

Ala Ala Ala Ala Gly Ala Gly Gln Gly Gly Tyr Gly Gly Gln Gly
    2300            2305              2310

Ala Gly Gln Gly Gly Ala Gly Ala Ala Ala Ala Ala Ala Ala
    2315            2320              2325

Gly Gly Ala Gly Gln Gly Gly Gln Gly Gly Tyr Gly Arg Gly Gly
    2330            2335              2340

Tyr Gly Gln Gly Gly Ala Gly Gln Gly Gly Ala Gly Ala Ala Ala
    2345            2350              2355

Ala Ala Ala Ala Gly Gly Ala Ser Gln Gly Gly Gln Gly Gly
    2360            2365              2370

Tyr Gly Gln Gly Asp Tyr Gly Gln Gly Gly Ala Gly Gln Gly Gly
    2375            2380              2385

Ala Ala Ala Ala Ala Ala Ala Ala Gly Gly Ala Gly Gln Gly Gly
    2390            2395              2400

Tyr Gly Arg Gly Gly Ala Gly Gln Gly Gly Ala Ala Ala Ala Ala
    2405            2410              2415

Gly Ala Gly Gln Gly Gly Tyr Gly Gly Gln Gly Ala Gly Gln Gly
    2420            2425              2430

Gly Ala Gly Ala Ala Ala Ala Ala Ala Ala Gly Gly Ala Gly
    2435            2440              2445

Arg Gly Gly Gln Gly Gly Tyr Gly Arg Gly Gly Tyr Gly Gln Gly
    2450            2455              2460

```
Gly Ala Gly Gln Gly Gly Ala Gly Ala Ala Ala Ala Ala Ala
    2465                2470                2475

Ala Gly Gly Ala Gly Gln Gly Gly Gln Gly Gly Tyr Gly Gln Gly
    2480                2485                2490

Gly Tyr Gly Gln Gly Gly Ala Gly Gln Gly Gly Ala Ala Ala Ala
    2495                2500                2505

Ala Ala Ala Ala Ala Gly Gly Ala Gly Gln Gly Gly Tyr Gly Arg
    2510                2515                2520

Gly Gly Ala Gly Gln Gly Gly Ala Ala Ala Ala Gly Ala Gly
    2525                2530                2535

Gln Gly Gly Tyr Gly Gly Gln Gly Ala Gly Gln Gly Gly Ala Gly
    2540                2545                2550

Ala Ala Ala Ala Ala Ala Ala Gly Gly Ala Gly Arg Gly Gly
    2555                2560                2565

Gln Gly Gly Tyr Gly Arg Gly Gly Tyr Gly Gln Gly Gly Ala Gly
    2570                2575                2580

Gln Gly Gly Ala Gly Ala Ala Ala Ala Ala Ala Ala Gly Gly
    2585                2590                2595

Ala Gly Gln Gly Gly Gln Gly Gly Tyr Gly Gln Gly Gly Tyr Gly
    2600                2605                2610

Gln Gly Gly Ala Gly Gln Gly Gly Ala Ala Ala Ala Ala Ala
    2615                2620                2625

Ala Val Gly Gly Ala Gly Gln Gly Gly Tyr Gly Arg Gly Gly Ala
    2630                2635                2640

Gly Gln Gly Gly Ala Ala Ala Ala Ala Ala Ala Ala Ala Gly
    2645                2650                2655

Ser Gly Gln Gly Gly Tyr Gly Gly Gln Gly Ala Gly Gln Gly Gly
    2660                2665                2670

Ala Gly Ala Ala Ala Ala Ala Ala Ala Gly Gly Ala Gly Gln
    2675                2680                2685

Gly Gly Gln Gly Gly Tyr Gly Gly Gly Tyr Gly Gln Gly Gly
    2690                2695                2700

Ala Gly Gln Gly Gly Ala Gly Ala Ala Ala Ala Ala Ala Ala
    2705                2710                2715

Gly Gly Ala Gly Gln Gly Gly Gln Gly Gly Tyr Gly Gln Gly Gly
    2720                2725                2730

Tyr Gly Gln Gly Gly Ala Gly Gln Gly Gly Ala Ala Ala Ala
    2735                2740                2745

Ala Ala Ala Ala Gly Gly Ala Gly Gln Gly Gly Tyr Gly Arg Gly
    2750                2755                2760

Gly Ala Gly Gln Gly Gly Ala Ala Ala Ala Thr Gly Ala Gly Gln
    2765                2770                2775

Gly Gly Tyr Gly Gly Gln Gly Ala Gly Gln Gly Gly Ala Gly Ala
    2780                2785                2790

Ala Ala Ala Ala Ala Ala Gly Gly Ala Gly Gln Gly Gly Gln
    2795                2800                2805

Gly Gly Tyr Gly Arg Gly Gly Tyr Gly Gln Gly Gly Ala Gly Gln
    2810                2815                2820

Gly Gly Ala Gly Ala Ala Ala Ala Ala Ala Ala Gly Gly Ala
    2825                2830                2835

Gly Gln Gly Gly Gln Gly Gly Tyr Gly Gln Gly Gly Tyr Gly Gln
    2840                2845                2850

Gly Gly Ala Gly Gln Gly Gly Ala Ala Ala Ala Ala Ala Ala Ala
```

```
              2855                2860                2865
Gly  Gly  Ala  Gly  Gln  Gly  Gly  Tyr  Gly  Arg  Gly  Gly  Ala  Gly  Gln
         2870                2875                2880
Gly  Gly  Ala  Ala  Ala  Ala  Ala  Ala  Ala  Ala  Gly  Ala  Gly  Gln
         2885                2890                2895
Gly  Gly  Tyr  Gly  Gly  Gln  Gly  Ala  Gly  Gln  Gly  Ala  Gly  Ala
    2900                2905                2910
Ala  Ala  Ala  Ala  Ala  Ala  Ala  Gly  Gly  Ala  Gly  Gln  Gly  Gly  Gln
         2915                2920                2925
Gly  Gly  Tyr  Gly  Arg  Gly  Gly  Tyr  Gly  Gln  Gly  Gly  Ala  Gly  Gln
         2930                2935                2940
Gly  Gly  Ala  Gly  Ala  Ala  Ala  Gly  Gly  Ala  Gly  Gln  Gly  Gly
         2945                2950                2955
Gln  Gly  Gly  Tyr  Gly  Gln  Gly  Gly  Tyr  Gly  Gln  Gly  Gly  Ala  Gly
         2960                2965                2970
Gln  Gly  Gly  Ala  Ala  Ala  Ala  Ala  Ala  Ala  Ala  Ala  Gly  Gly
         2975                2980                2985
Ala  Gly  Gln  Gly  Gly  Tyr  Gly  Gly  Tyr  Gly  Gln  Gln  Gly  Gly  Ala
         2990                2995                3000
Gly  Ala  Ala  Ala  Ala  Ala  Ala  Ser  Gly  Pro  Gly  Gln  Ile  Tyr  Tyr
    3005                3010                3015
Gly  Pro  Gln  Ser  Val  Ala  Ala  Pro  Ala  Ala  Ala  Ala  Ser  Ala
    3020                3025                3030
Leu  Ala  Ala  Pro  Ala  Thr  Ser  Ala  Arg  Ile  Ser  Ser  His  Ala  Ser
         3035                3040                3045
Ala  Leu  Leu  Ser  Asn  Gly  Pro  Thr  Asn  Pro  Ala  Ser  Ile  Ser  Asn
         3050                3055                3060
Val  Ile  Ser  Asn  Ala  Val  Ser  Gln  Ile  Ser  Ser  Ser  Asn  Pro  Gly
         3065                3070                3075
Ala  Ser  Ala  Cys  Asp  Val  Leu  Val  Gln  Ala  Leu  Leu  Glu  Leu  Val
         3080                3085                3090
Thr  Ala  Leu  Leu  Thr  Ile  Ile  Gly  Ser  Ser  Asn  Ile  Gly  Ser  Val
         3095                3100                3105
Asn  Tyr  Asp  Ser  Ser  Gly  Gln  Tyr  Ala  Gln  Val  Val  Thr  Gln  Ser
         3110                3115                3120
Val  Gln  Asn  Ala  Phe  Ala
         3125

<210> SEQ ID NO 25
<211> LENGTH: 751
<212> TYPE: PRT
<213> ORGANISM: artificial
<220> FEATURE:
<223> OTHER INFORMATION: synthetic

<400> SEQUENCE: 25

Met  Arg  Arg  Met  Tyr  Ser  Leu  Ser  Ile  Gln  Ser  Asp  Phe  Pro  Thr  Thr
1                 5                  10                  15

Thr  Met  Thr  Trp  Ser  Thr  Arg  Leu  Ala  Leu  Ser  Phe  Phe  Ala  Val  Ile
              20                  25                  30

Cys  Thr  Gln  Ser  Ile  Tyr  Ala  Leu  Gly  Gln  Gly  Asn  Thr  Pro  Trp  Ser
         35                  40                  45

Thr  Lys  Ala  Asn  Ala  Asp  Asn  Phe  Met  Asn  Gly  Phe  Leu  Ser  Ala  Cys
    50                  55                  60

Ala  Gln  Ser  Gly  Val  Phe  Ser  Ala  Asp  Gln  Val  Asp  Asp  Met  Thr  Thr
```

```
             65                  70                  75                  80
        Ile Gly Lys Thr Leu Met Ile Ala Met Asp Lys Met Gly Gly Lys Ile
                         85                  90                  95
        Ser Ser Ser Lys Leu Gln Ala Leu Asp Met Ala Phe Ala Ser Ser Val
                        100                 105                 110
        Ala Glu Ile Ala Thr Ala Glu Gly Ala Asn Ile Asn Asp Ile Thr
                        115                 120                 125
        Asp Ala Ile Arg Tyr Ala Leu Gln Asn Ala Phe Tyr Gln Thr Thr Gly
                130                 135                 140
        Ala Val Asn Ser Lys Phe Ile Asn Glu Ile Ser Asn Leu Ile Tyr Met
        145                 150                 155                 160
        Phe Ala Gln Thr Asn Ile Asn Asp Val Asn Gly Gly Gly Gly Tyr Gly
                        165                 170                 175
        Gln Gly Gly Ala Gly Gln Gly Gly Ala Ala Ala Ala Ala Gly Gly
                        180                 185                 190
        Ala Gly Gln Gly Gly Tyr Gly Arg Gly Gly Ala Arg Gln Gly Gly Ala
                        195                 200                 205
        Ala Ala Ala Ala Gly Ala Gly Gln Gly Gly Tyr Gly Asp Gln Gly Ala
                210                 215                 220
        Gly Gln Gly Gly Ala Gly Ala Ala Ala Ala Ala Thr Ala Ser Gly
        225                 230                 235                 240
        Gly Ala Gly Gln Gly Gly Tyr Gly Arg Gly Gly Ala Gly Gln Gly Gly
                        245                 250                 255
        Ala Ala Ala Ala Ala Ala Ala Ala Gly Ala Gly Gln Gly Gly Tyr
                        260                 265                 270
        Gly Gly Gln Gly Ala Ala Gln Gly Gly Ala Gly Ala Ala Ala Ala
                        275                 280                 285
        Ala Ala Ala Gly Gly Ala Gly Leu Gly Gly Leu Gly Gly Tyr Gly Gln
                290                 295                 300
        Gly Gly Ser Gly Ala Ala Ala Ala Gly Gly Ala Gly Gln Gly Gly
        305                 310                 315                 320
        Glu Gly Gly Val Gly Gln Gly Gly Tyr Gly Gln Arg Gly Ala Gly Gln
                        325                 330                 335
        Gly Gly Val Gly Ala Ala Ala Ala Ala Ala Ala Ala Gly Gly Ala
                        340                 345                 350
        Gly Gln Gly Glu Tyr Gly Arg Gly Gly Ala Gly Lys Gly Gly Ala Ala
                        355                 360                 365
        Ala Ala Ala Ala Ala Ala Gly Ala Gly Gln Gly Gly Tyr Gly Gly
                370                 375                 380
        Gln Gly Gly Ala Gly Ala Ala Ala Ala Ala Ala Ala Gly Gly Ala
        385                 390                 395                 400
        Gly Leu Gly Gly Lys Gly Gly Tyr Gly Gln Gly Gly Ala Gly Ala Ala
                        405                 410                 415
        Ala Ala Ala Ala Ala Gly Gly Ala Gly Gln Gly Gly Gln Gly Gly
                        420                 425                 430
        Tyr Gly Arg Gly Gly Tyr Gly Arg Gly Gly Ala Gly Gln Gly Gly Ala
                        435                 440                 445
        Gly Ala Ala Ala Ala Ala Ala Ala Gly Gly Ala Gly Gln Val Gly
                450                 455                 460
        Gln Ser Gly Tyr Gly Gln Glu Gly Tyr Gly Gln Gly Gly Ala Gly Gln
        465                 470                 475                 480
        Gly Gly Ala Gly Ala Ala Ala Ala Ala Ala Ala Ala Gly Gly Ala
                        485                 490                 495
```

-continued

Gly Gln Gly Gly Tyr Gly Arg Gly Gly Ala Gly Gln Gly Glu Ala Ala
            500                 505                 510

Ala Ala Ala Ala Ala Ala Ala Gly Ala Gly Gln Gly Gly Tyr Gly Gly
        515                 520                 525

Gln Gly Ala Gly Gln Gly Arg Ala Gly Ala Ala Ala Ala Ala Ala Ala
        530                 535                 540

Ala Gly Gly Ala Gly Gln Gly Gly Gln Gly Gly Tyr Gly Gln Gly Gly
545                 550                 555                 560

Tyr Gly Gln Gly Gly Ser Gly Ala Ala Ala Ala Ala Ala Ala Ala Ala
                565                 570                 575

Gly Gly Ala Gly Gln Gly Gly Gln Gly Gly Tyr Gly Gln Gly Gly Tyr
        580                 585                 590

Gly Gln Gly Gly Ala Gly Gln Gly Gly Ala Ala Val Ala Ala Ala
        595                 600                 605

Ala Ala Ala Gly Gly Ala Gly Gln Gly Gly Tyr Gly Pro Gln Gly Gly
        610                 615                 620

Ala Gly Ala Thr Ala Ala Ser Ala Ser Gly Pro Val Gln Ile Tyr Tyr
625                 630                 635                 640

Gly Pro Gln Ser Val Val Ala Pro Ala Ala Ala Ala Ser Ala Leu
                645                 650                 655

Ala Ala Pro Ala Thr Ser Ala Arg Ile Ser Ser His Ala Ser Ala Leu
        660                 665                 670

Leu Ser Asn Gly Pro Thr Asn Pro Ala Ser Ile Ser Asn Val Ile Ser
        675                 680                 685

Asn Ala Val Ser Gln Ile Ser Ser Asn Pro Gly Ala Ser Ala Cys
        690                 695                 700

Asp Val Leu Val Gln Ala Leu Leu Glu Leu Val Thr Ala Leu Leu Thr
705                 710                 715                 720

Ile Ile Gly Ser Ser Asn Ile Gly Ser Val Asn Tyr Asp Ser Ser Gly
                725                 730                 735

Gln Tyr Ala Gln Val Val Thr Gln Ser Val Gln Asn Ala Phe Ala
        740                 745                 750

<210> SEQ ID NO 26
<211> LENGTH: 748
<212> TYPE: PRT
<213> ORGANISM: artificial
<220> FEATURE:
<223> OTHER INFORMATION: synthetic

<400> SEQUENCE: 26

Met Arg Arg Met Tyr Ser Leu Ser Ile Gln Ser Asp Phe Pro Thr Thr
1               5                   10                  15

Thr Met Thr Trp Ser Thr Arg Leu Ala Leu Ser Phe Phe Ala Val Ile
            20                  25                  30

Cys Thr Gln Ser Ile Tyr Ala Leu Gly Gln Gly Asn Thr Pro Trp Ser
        35                  40                  45

Thr Lys Ala Asn Ala Asp Asn Phe Met Asn Gly Phe Leu Ser Ala Cys
    50                  55                  60

Ala Gln Ser Gly Val Phe Ser Ala Asp Gln Val Asp Asp Met Thr Thr
65                  70                  75                  80

Ile Gly Lys Thr Leu Met Ile Ala Met Asp Lys Met Gly Gly Lys Ile
                85                  90                  95

Ser Ser Ser Lys Leu Gln Ala Leu Asp Met Ala Phe Ala Ser Ser Val
            100                 105                 110

```
Ala Glu Ile Ala Thr Ala Glu Gly Gly Ala Asn Ile Asn Asp Ile Thr
        115                 120                 125

Asp Ala Ile Arg Tyr Ala Leu Gln Asn Ala Phe Tyr Gln Thr Thr Gly
        130                 135                 140

Ala Val Asn Ser Lys Phe Ile Asn Glu Ile Ser Asn Leu Ile Tyr Phe
145                 150                 155                 160

Ala Gln Thr Asn Ile Asn Asp Val Asn Gly Gly Gly Tyr Gly Gln
        165                 170                 175

Gly Gly Ala Gly Gln Gly Gly Ala Ala Ala Ala Ala Gly Gly Ala
        180                 185                 190

Gly Gln Gly Gly Tyr Gly Arg Gly Gly Ala Arg Gln Gly Gly Ala Ala
        195                 200                 205

Ala Ala Ala Gly Ala Gly Gln Gly Gly Tyr Gln Gly Ala Gly Gln Gly
        210                 215                 220

Gly Ala Gly Ala Ala Ala Ala Ala Thr Ala Ser Gly Gly Ala Gly
225                 230                 235                 240

Gln Gly Gly Tyr Gly Arg Gly Gly Ala Gly Gln Gly Gly Ala Ala Ala
        245                 250                 255

Ala Ala Ala Ala Ala Ala Gly Ala Gly Gln Gly Gly Tyr Gly Gly Gln
        260                 265                 270

Gly Ala Ala Gln Gly Gly Ala Gly Ala Ala Ala Ala Ala Ala Ala
        275                 280                 285

Gly Gly Ala Gly Leu Gly Gly Leu Gly Gly Tyr Gly Gln Gly Gly Ser
        290                 295                 300

Gly Ala Ala Ala Ala Gly Gly Ala Gly Gln Gly Gly Glu Gly Gly
305                 310                 315                 320

Val Gly Gln Gly Gly Tyr Gly Gln Arg Gly Ala Gly Gln Gly Gly Val
        325                 330                 335

Gly Ala Ala Ala Ala Ala Ala Ala Gly Gly Ala Gly Gln Gly
        340                 345                 350

Glu Tyr Gly Arg Gly Gly Ala Gly Lys Gly Gly Ala Ala Ala Ala Ala
        355                 360                 365

Ala Ala Ala Ala Gly Ala Gly Gln Gly Gly Tyr Gly Gly Gln Gly Gly
        370                 375                 380

Ala Gly Ala Ala Ala Ala Ala Ala Ala Gly Gly Ala Gly Leu Gly
385                 390                 395                 400

Gly Lys Gly Gly Tyr Gly Gln Gly Gly Ala Gly Ala Ala Ala Ala
        405                 410                 415

Ala Ala Ala Gly Gly Ala Gly Gln Gly Gly Gln Gly Gly Tyr Gly Arg
        420                 425                 430

Gly Gly Tyr Gly Arg Gly Gly Ala Gly Gln Gly Gly Ala Gly Ala Ala
        435                 440                 445

Ala Ala Ala Ala Ala Gly Gly Ala Gly Gln Val Gly Gln Ser Gly
        450                 455                 460

Tyr Gly Gln Glu Gly Tyr Gly Gly Gly Ala Gly Gly Gly Gly Ala
465                 470                 475                 480

Gly Ala Ala Ala Ala Ala Ala Ala Ala Gly Gly Ala Gly Gln Gly
        485                 490                 495

Gly Tyr Gly Arg Gly Gly Ala Gly Gln Gly Glu Ala Ala Ala Ala
        500                 505                 510

Ala Ala Ala Ala Gly Ala Gly Gln Gly Gly Tyr Gly Gly Gln Gly Ala
        515                 520                 525
```

Gly Gln Gly Arg Ala Gly Ala Ala Ala Ala Ala Gly Gly
530                 535                 540

Ala Gly Gln Gly Gly Gln Gly Gly Tyr Gly Gln Gly Gly Tyr Gly Gln
545                 550                 555                 560

Gly Gly Ser Gly Ala Ala Ala Ala Ala Ala Ala Gly Gly Ala
                565                 570                 575

Gly Gln Gly Gly Gln Gly Gly Tyr Gly Gln Gly Gly Tyr Gly Gln Gly
                580                 585                 590

Gly Ala Gly Gln Gly Gly Ala Ala Val Ala Ala Ala Ala Ala
                595                 600                 605

Gly Gly Ala Gly Gln Gly Gly Tyr Gly Pro Gln Gly Gly Ala Gly Ala
610                 615                 620

Thr Ala Ala Ser Ala Ser Gly Pro Val Gln Ile Tyr Tyr Gly Pro Gln
625                 630                 635                 640

Ser Val Val Ala Pro Ala Ala Ala Ala Ser Ala Leu Ala Ala Pro
                645                 650                 655

Ala Thr Ser Ala Arg Ile Ser Ser His Ala Ser Ala Leu Leu Ser Asn
                660                 665                 670

Gly Pro Thr Asn Pro Ala Ser Ile Ser Asn Val Ile Ser Asn Ala Val
                675                 680                 685

Ser Gln Ile Ser Ser Ser Asn Pro Gly Ala Ser Ala Cys Asp Val Leu
690                 695                 700

Val Gln Ala Leu Leu Glu Leu Val Thr Ala Leu Leu Thr Ile Ile Gly
705                 710                 715                 720

Ser Ser Asn Ile Gly Ser Val Asn Tyr Asp Ser Ser Gly Gln Tyr Ala
                725                 730                 735

Gln Val Val Thr Gln Ser Val Gln Asn Ala Phe Ala
                740                 745

<210> SEQ ID NO 27
<211> LENGTH: 631
<212> TYPE: PRT
<213> ORGANISM: artificial
<220> FEATURE:
<223> OTHER INFORMATION: synthetic

<400> SEQUENCE: 27

Ser Arg Asp Phe Pro Thr Thr Thr Met Thr Trp Ser Thr Arg Leu Ala
1               5                   10                  15

Leu Ser Phe Leu Phe Val Leu Cys Thr Gln Ser Leu Tyr Ala Leu Ala
                20                  25                  30

Gln Ala Asn Thr Pro Trp Ser Ser Lys Ala Asn Ala Asp Ala Phe Ile
                35                  40                  45

Asn Ser Phe Ile Ser Ala Ala Ser Asn Thr Gly Ser Phe Ser Gln Asp
                50                  55                  60

Gln Met Glu Asp Met Ser Leu Ile Gly Asn Thr Leu Met Ala Ala Met
65                  70                  75                  80

Asp Asn Met Gly Gly Arg Ile Thr Pro Ser Lys Leu Gln Ala Leu Asp
                85                  90                  95

Met Ala Phe Ala Ser Ser Val Ala Glu Ile Ala Ala Ser Glu Gly Gly
                100                 105                 110

Asp Leu Gly Val Thr Thr Asn Ala Ile Ala Asp Ala Leu Thr Ser Ala
                115                 120                 125

Phe Tyr Gln Thr Thr Gly Val Val Asn Ser Arg Phe Ile Ser Glu Ile
                130                 135                 140

-continued

```
Arg Ser Leu Ile Gly Met Phe Ala Gln Ala Ser Ala Asn Asp Val Tyr
145                 150                 155                 160

Ala Ser Ala Gly Ser Ser Gly Gly Gly Tyr Gly Ala Ser Ser Ala
            165                 170                 175

Ser Ala Ala Ser Ala Ser Ala Ala Ala Pro Ser Gly Val Ala Tyr Gln
                180                 185                 190

Ala Pro Ala Gln Ala Gln Ile Ser Phe Thr Leu Arg Gly Gln Gln Pro
        195                 200                 205

Val Ser Tyr Gly Gln Gly Gly Ala Gly Pro Gly Gly Ala Gly Ala Ala
    210                 215                 220

Ala Ala Ala Ala Ala Ala Gly Gly Ala Gly Gln Gly Gly Gln Gly
225                 230                 235                 240

Gly Tyr Gly Gln Gly Gly Tyr Gly Gln Gly Gly Ala Gly Gln Gly Gly
                245                 250                 255

Ser Gly Ala Ala Ala Ala Ala Gly Gly Thr Gly Gln Gly Gly Ala Gly
            260                 265                 270

Gln Gly Gly Ala Gly Ala Ala Ala Ala Ala Ala Ala Ala Gly Gly
                275                 280                 285

Ala Gly Gln Gly Gly Gln Gly Gly Tyr Gly Gln Gly Gly Tyr Gly Gln
290                 295                 300

Gly Gly Thr Gly Gln Gly Gly Ala Gly Ala Ala Ala Arg Gly Gly Tyr
305                 310                 315                 320

Gly Gln Gly Gly Ala Gly Gln Gly Gly Ala Gly Ala Ala Ala Ala
                325                 330                 335

Ala Ala Ala Gly Gly Ala Gly Gln Gly Gly Gln Gly Gly Tyr Gly Gln
            340                 345                 350

Gly Gly Tyr Gly Gln Gly Gly Ala Gly Gln Gly Gly Ala Ala Ala Ala
            355                 360                 365

Ala Ala Ala Ala Gly Gly Ala Gly Gln Gly Gly Tyr Gly Arg Gly Gly
        370                 375                 380

Ala Gly Gln Gly Gly Ala Ala Ala Ala Ala Ala Ala Ala Gly Ala
385                 390                 395                 400

Gly Gln Gly Gly Tyr Gly Gly Gln Gly Ala Gln Gly Gly Ala Gly
                405                 410                 415

Ala Ala Ala Ala Ala Ala Ala Gly Gly Ala Gly Gln Gly Gly Gln
                420                 425                 430

Gly Tyr Gly Gly Tyr Gly Arg Gly Gly Tyr Gly Gln Gly Gly Ala Gly Gln Gly
            435                 440                 445

Gly Ala Gly Ala Ala Ala Ala Ala Ala Ala Gly Gly Ala Gly
    450                 455                 460

Gln Gly Gly Gln Gly Gly Tyr Gly Gln Gly Gly Tyr Gly Gln Gly Gly
465                 470                 475                 480

Ala Gly Gln Gly Gly Ala Ala Ala Ala Ala Ala Ala Ala Ala Gly
            485                 490                 495

Gly Ala Gly Gln Gly Gly Tyr Gly Gly Tyr Gly Gln Gln Gly Gly Ala
        500                 505                 510

Gly Ala Ala Ala Ala Ala Ser Gly Pro Gly Gln Ile Tyr Tyr Gly
        515                 520                 525

Pro Gln Ser Val Ala Ala Pro Ala Ala Ala Ser Ala Leu Ala
    530                 535                 540

Ala Pro Ala Thr Ser Ala Arg Ile Ser Ser His Ala Ser Ala Leu Leu
545                 550                 555                 560

Ser Asn Gly Pro Thr Asn Pro Ala Ser Ile Ser Asn Val Ile Ser Asn
```

```
                565                 570                 575
Ala Val Ser Gln Ile Ser Ser Asn Pro Gly Ala Ser Ala Cys Asp
            580                 585                 590

Val Leu Val Gln Ala Leu Leu Glu Leu Val Thr Ala Leu Leu Thr Ile
            595                 600                 605

Ile Gly Ser Ser Asn Ile Gly Ser Val Asn Tyr Asp Ser Ser Gly Gln
            610                 615                 620

Tyr Ala Gln Val Val Thr Gln
625                 630

<210> SEQ ID NO 28
<211> LENGTH: 697
<212> TYPE: PRT
<213> ORGANISM: artificial
<220> FEATURE:
<223> OTHER INFORMATION: synthetic

<400> SEQUENCE: 28

Met Tyr Ser Leu Ser Ile Gln Ser Asp Phe Pro Thr Thr Thr Met Thr
1               5                   10                  15

Trp Ser Thr Arg Leu Ala Leu Ser Phe Phe Ala Val Ile Cys Thr Gln
            20                  25                  30

Ser Ile Tyr Ala Leu Gly Gln Gly Asn Thr Pro Trp Ser Thr Lys Ala
            35                  40                  45

Asn Ala Asp Asn Phe Met Asn Gly Phe Leu Ser Ala Cys Ala Gln Ser
        50                  55                  60

Gly Val Phe Ser Ala Asp Gln Val Asp Met Thr Thr Ile Gly Lys
65                  70                  75                  80

Thr Leu Met Ile Ala Met Asp Lys Met Gly Gly Lys Ile Ser Ser Ser
                85                  90                  95

Lys Leu Gln Ala Leu Asp Met Ala Phe Ala Ser Ser Val Ala Glu Ile
            100                 105                 110

Ala Thr Ala Glu Gly Gly Ala Asn Ile Asn Asp Ile Thr Asp Ala Ile
            115                 120                 125

Arg Tyr Ala Leu Gln Asn Ala Phe Tyr Gln Thr Thr Gly Ala Val Asn
        130                 135                 140

Ser Lys Phe Ile Asn Glu Ile Ser Asn Leu Ile Tyr Met Phe Ala Gln
145                 150                 155                 160

Thr Asn Ile Asn Asp Val Asn Gly Gly Gly Tyr Gly Gln Gly Gly
            165                 170                 175

Ala Gly Gln Gly Gly Ala Ala Ala Ala Gly Gly Ala Gly Gln
            180                 185                 190

Gly Gly Tyr Gly Arg Gly Gly Ala Gln Gly Gly Ala Ala Ala
            195                 200                 205

Ala Gly Ala Gly Gln Gly Gly Tyr Gly Asp Gln Gly Ala Gly Gln Gly
        210                 215                 220

Gly Ala Gly Ala Ala Ala Ala Thr Ala Ser Gly Gly Ala Gly
225                 230                 235                 240

Gln Gly Gly Tyr Gly Arg Gly Gly Ala Gly Gln Gly Gly Glu Ala Ala
                245                 250                 255

Ala Ala Ala Ala Ala Gly Ala Gln Gly Gly Tyr Gly Gln
            260                 265                 270

Glu Ala Ala Gln Gly Gly Ala Gly Ala Ala Ala Ala Ala Ala Ala
            275                 280                 285

Gly Gly Ala Gly Leu Gly Gly Leu Gly Gly Tyr Gly Gln Gly Gly Ser
```

```
            290                 295                 300
Gly Ala Ala Ala Ala Gly Ala Gly Gln Gly Glu Gly Gly
305                 310                 315                 320

Val Gly Gln Gly Gly Tyr Gly Gln Arg Gly Ala Gly Gln Gly Gly Ala
                325                 330                 335

Gly Ala Ala Ala Ala Ala Gly Gly Ala Gly Gln Gly Glu Tyr Gly
                340                 345                 350

Arg Gly Gly Ala Gly Gln Gly Arg Ala Ala Ala Ala Ala Ala
            355                 360                 365

Ala Gly Ala Gly Gln Gly Ser Tyr Gly Gly Gln Gly Ala Gly Gly Tyr
            370                 375                 380

Gly Arg Gly Gly Ala Gly Gln Gly Gly Ala Gly Ala Ala Ala Ala
385                 390                 395                 400

Ala Ala Ala Gly Gly Ala Gly Gln Val Gly Gln Ser Gly Tyr Gly Gln
                405                 410                 415

Glu Gly Tyr Gly Gln Gly Gly Ala Gly Gln Gly Gly Ala Gly Ala Ala
                420                 425                 430

Ala Ala Ala Ala Ala Ala Gly Gly Ala Gly Gln Gly Gly Tyr Gly
            435                 440                 445

Arg Gly Gly Ala Gly Gln Gly Gly Ala Ala Ala Ala Ala Ala Ala
            450                 455                 460

Ala Gly Ala Gly Gln Gly Gly Tyr Gly Gly Gln Gly Ala Gly Gln Gly
465                 470                 475                 480

Gly Ala Gly Ala Ala Ala Ala Ala Ala Gly Trp Ala Gly Gln
                485                 490                 495

Gly Gly Gln Gly Gly Tyr Gly Gln Gly Gly Tyr Gly Gln Gly Gly Ser
                500                 505                 510

Gly Ala Ala Ala Ala Ala Ala Ala Gly Gly Ala Gly Gln Gly
            515                 520                 525

Gly Gln Gly Gly Tyr Gly Gln Gly Gly Tyr Asp Gln Gly Gly Ala Gly
            530                 535                 540

Gln Gly Gly Ala Ala Val Ala Ala Ala Ala Ala Gly Gly Ala
545                 550                 555                 560

Gly Gln Gly Gly Tyr Gly Pro Gln Gly Gly Ala Gly Ala Ala Ala
                565                 570                 575

Ser Ala Ser Gly Pro Val Gln Ile Tyr Tyr Gly Pro Gln Ser Val Ala
                580                 585                 590

Ala Pro Ala Ala Ala Ala Ser Ala Leu Ala Pro Ala Thr Ser
            595                 600                 605

Ala Arg Ile Ser Ser His Ala Ser Ala Leu Leu Ser Asn Gly Pro Thr
            610                 615                 620

Asn Pro Ala Ser Ile Ser Asn Val Ile Ser Asn Ala Val Ser Gln Ile
625                 630                 635                 640

Ser Ser Ser Asn Pro Gly Ala Ser Ala Cys Asp Val Leu Val Gln Ala
                645                 650                 655

Leu Leu Glu Leu Val Thr Ala Leu Leu Thr Ile Ile Gly Ser Ser Asn
                660                 665                 670

Ile Gly Ser Val Asn Tyr Asp Ser Ser Gly Gln Tyr Ala Gln Val Val
                675                 680                 685

Thr Gln Ser Val Gln Asn Ala Phe Ala
            690                 695

<210> SEQ ID NO 29
```

<211> LENGTH: 675
<212> TYPE: PRT
<213> ORGANISM: artificial
<220> FEATURE:
<223> OTHER INFORMATION: synthetic

<400> SEQUENCE: 29

```
Met Thr Trp Ser Thr Arg Leu Ala Leu Ser Phe Leu Leu Val Leu Cys
1               5                   10                  15

Thr Gln Ser Ile Tyr Ala Leu Ala Gln Ala Asn Thr Pro Trp Ser Ser
            20                  25                  30

Lys Ala Asn Ala Asp Ala Phe Ile Asn Ser Phe Ile Ser Ala Ala Ser
        35                  40                  45

Asn Thr Gly Ser Phe Ser Gln Asp Gln Met Glu Asp Met Ser Leu Ile
    50                  55                  60

Gly Asn Thr Leu Met Ala Ala Met Asp Asn Met Gly Gly Arg Ile Thr
65                  70                  75                  80

Pro Ser Lys Leu Gln Ala Leu Asp Met Ala Phe Ala Ser Ser Val Ala
                85                  90                  95

Glu Ile Ala Ala Ser Glu Gly Gly Asp Leu Gly Val Thr Thr Asn Ala
            100                 105                 110

Ile Ala Asp Ala Leu Thr Ser Ala Phe Tyr Gln Thr Thr Gly Val Val
        115                 120                 125

Asn Ser Arg Phe Ile Ser Glu Ile Arg Ser Leu Ile Gly Met Phe Ala
    130                 135                 140

Gln Ala Ser Ala Asn Asp Val Tyr Ala Ser Ala Gly Ser Ser Gly Gly
145                 150                 155                 160

Gly Gly Tyr Gly Ala Ser Ser Ala Ser Ala Ala Ser Ala Ser Ala Ala
                165                 170                 175

Ala Pro Ser Gly Val Ala Tyr Gln Ala Pro Ala Gln Ala Gln Ile Ser
            180                 185                 190

Phe Ser Leu Arg Gly Gln Gln Pro Val Gly Tyr Gly Gln Gly Gly Ala
        195                 200                 205

Ser Ala Ala Ser Gly Ala Ala Ala Gly Gln Gly Gly Ala Gly Pro Gly
    210                 215                 220

Gly Ala Gly Ala Ala Ala Ala Gly Gly Ala Gly Gln Gly Gly Gln Gly
225                 230                 235                 240

Gly Tyr Gly Gln Gly Gly Tyr Gly Gln Gly Gly Ala Gly Gln Gly Gly
                245                 250                 255

Ser Gly Ala Ala Ala Ala Ala Ala Ala Ala Gly Gly Thr Gly Gln
            260                 265                 270

Gly Gly Ala Gly Gln Gly Gly Ala Gly Ala Ala Ala Ala Ala Ala
        275                 280                 285

Ala Ala Gly Gly Ala Gly Gln Gly Gly Gln Gly Gly Tyr Gly Gln Gly
    290                 295                 300

Gly Tyr Gly Gln Gly Gly Ser Gly Ala Ala Ala Ala Ala Ala Ala
305                 310                 315                 320

Ala Gly Gly Ala Gly Gln Gly Gly Gln Gly Gly Asp Tyr Gly Gln Gly
                325                 330                 335

Tyr Gly Gln Gly Gly Ala Gly Gln Gly Gly Ala Gly Ala Ala Ala Ala
            340                 345                 350

Ala Ala Ala Ala Ala Gly Gly Ala Gly Gln Gly Gly Tyr Gly Arg Gly
        355                 360                 365

Ala Ala Ala Ala Ala Ala Ala Gly Gly Ala Gly Gln Gly Gly Gln
    370                 375                 380
```

```
Gly Gly Tyr Gly Gln Gly Gly Tyr Gly Gln Gly Gly Ser Gly Ala Ala
385                 390                 395                 400

Ala Ala Ala Ala Ala Ala Gly Gly Ala Gly Gln Gly Gly Gln Gly
            405                 410                 415

Gly Tyr Gly Gln Gly Gly Tyr Gly Gln Gly Gly Ser Gly Ala Ala Ala
                420                 425                 430

Ala Ala Ala Ala Ala Ala Gly Gly Ala Gly Gln Gly Gly Gln Gly Gly
            435                 440                 445

Tyr Gly Gln Gly Gly Tyr Gly Gln Gly Gly Ala Gly Gln Gly Gly Ala
        450                 455                 460

Gly Ala Ala Ala Ala Ala Ala Ala Gly Gly Ala Gly Gln Gly
465                 470                 475                 480

Gly Tyr Gly Arg Gly Gly Ala Gly Gln Gly Gly Ala Ala Ala Ala
            485                 490                 495

Ala Ala Ala Ala Gly Ala Gly Gln Arg Gly Tyr Gly Gly Gln Gly Ala
            500                 505                 510

Gly Gln Gly Gly Ala Gly Ala Ala Ala Ala Ala Ala Gly Gly
        515                 520                 525

Ala Gly Gln Gly Gly Gln Arg Gly Tyr Gly Gln Gly Gly Tyr Gly Gln
        530                 535                 540

Gly Gly Ser Gly Ala Ala Ala Ala Ala Ala Ser Gly Pro Gly
545                 550                 555                 560

Gln Val Tyr Tyr Gly Pro Gln Ser Phe Ala Ala Pro Ala Ala Ala
            565                 570                 575

Ala Ser Ala Leu Ser Ala Pro Ala Thr Ser Ala Arg Ile Ser Ser His
            580                 585                 590

Ala Ser Ala Leu Leu Ser Ser Gly Pro Thr Asn Pro Ala Ser Ile Ser
            595                 600                 605

Asn Val Ile Ser Asn Ala Val Ser Gln Ile Ser Ser Ser Asn Pro Gly
        610                 615                 620

Ala Ser Ala Cys Asp Val Leu Val Gln Ala Leu Leu Glu Leu Val Thr
625                 630                 635                 640

Ala Leu Leu Thr Ile Ile Gly Ser Ser Asn Ile Gly Ser Val Asn Tyr
                645                 650                 655

Asp Ser Ser Gly Gln Tyr Ala Gln Val Val Thr Gln Ser Val Gln Asn
            660                 665                 670

Val Phe Gly
        675

<210> SEQ ID NO 30
<211> LENGTH: 605
<212> TYPE: PRT
<213> ORGANISM: artificial
<220> FEATURE:
<223> OTHER INFORMATION: synthetic

<400> SEQUENCE: 30

Met Thr Trp Ser Thr Arg Leu Ala Leu Ser Phe Leu Phe Val Leu Cys
1               5                   10                  15

Thr Gln Ser Leu Tyr Ala Leu Ala Gln Ala Asn Thr Pro Trp Ser Ser
            20                  25                  30

Lys Ala Asn Ala Asp Ala Phe Ile Asn Ser Phe Ile Ser Ala Ala Ser
        35                  40                  45

Asn Thr Gly Ser Phe Ser Gln Asp Gln Met Glu Asp Met Ser Leu Ile
    50                  55                  60
```

```
Gly Asn Thr Leu Met Ala Ala Met Asp Asn Met Gly Arg Ile Thr
 65                  70                  75                  80

Pro Ser Lys Leu Gln Ala Leu Asp Met Ala Phe Ala Ser Ser Val Ala
                 85                  90                  95

Glu Ile Ala Ala Ser Glu Gly Gly Asp Leu Gly Val Thr Thr Asn Ala
            100                 105                 110

Ile Ala Asp Ala Leu Thr Ser Ala Phe Tyr Gln Thr Thr Gly Val Val
        115                 120                 125

Asn Ser Arg Phe Ile Ser Glu Ile Arg Ser Leu Ile Gly Met Phe Ala
130                 135                 140

Gln Ala Ser Ala Asn Asp Val Tyr Ala Ser Ala Gly Ser Ser Gly Gly
145                 150                 155                 160

Gly Gly Tyr Gly Ala Ser Ser Ala Ser Ala Ser Ala Ser Ala Ala
                165                 170                 175

Ala Pro Ser Gly Val Ala Tyr Gln Ala Pro Ala Gln Ala Gln Ile Ser
            180                 185                 190

Phe Thr Leu Arg Gly Gln Gln Pro Val Ser Tyr Gly Gln Gly Gly Ala
        195                 200                 205

Gly Pro Gly Gly Ala Gly Ala Ala Ala Ala Ala Ala Ala Ala Gly
210                 215                 220

Gly Ala Gly Gln Gly Gly Gln Gly Gly Tyr Gly Gln Gly Gly Tyr Gly
225                 230                 235                 240

Gln Gly Gly Ala Gly Gln Gly Ser Gly Ala Ala Ala Ala Gly
            245                 250                 255

Gly Thr Gly Gln Gly Gly Ala Gly Gln Gly Gly Ala Gly Ala Ala Ala
            260                 265                 270

Ala Ala Ala Ala Ala Ala Gly Gly Ala Gly Gln Gly Gly Gln Gly Gly
            275                 280                 285

Tyr Gly Gln Gly Gly Tyr Gly Gln Gly Gly Thr Gly Gln Gly Gly Ala
290                 295                 300

Gly Ala Ala Ala Ala Ala Ala Ala Gly Gly Ala Gly Gln Gly Gly
305                 310                 315                 320

Gln Gly Gly Tyr Gly Gln Gly Gly Tyr Gly Gln Gly Gly Ser Gly Ala
            325                 330                 335

Ala Ala Ala Ala Ala Ala Ala Gly Gly Ala Gly Gln Gly Gly Gln
            340                 345                 350

Gly Gly Tyr Gly Gln Gly Gly Tyr Gly Gln Gly Gly Ala Gly Gln Gly
            355                 360                 365

Gly Ala Gly Ala Ala Gly Gln Gly Gly Tyr Gly Gln Gly Gly Tyr Gly
        370                 375                 380

Gln Gly Gly Ala Gly Gln Gly Gly Ala Ala Ala Ala Ala Ala Ala
385                 390                 395                 400

Gly Gly Ala Gly Gln Gly Gly Tyr Gly Arg Gly Gly Ala Gly Gln Gly
            405                 410                 415

Gly Ala Ala Ala Ala Ala Ala Ala Ala Gly Ala Gly Gln Gly Gly
            420                 425                 430

Tyr Gly Gly Gln Gly Ala Gly Gln Gly Gly Ala Gly Ala Ala Ala
            435                 440                 445

Ala Ala Ala Gly Gly Ala Gly Gln Gly Gly Gln Gly Gly Tyr Gly
        450                 455                 460

Arg Gly Gly Tyr Asp Gln Gly Gly Ala Gly Gln Gly Gly Ala Gly Ala
465                 470                 475                 480
```

```
Ala Ala Ala Ala Ala Ala Ala Gly Gly Ala Gly Gln Gly Gly Gln
                    485                 490             495

Gly Gly Tyr Gly Gln Gly Gly Tyr Gly Gln Gly Gly Ala Gly Gln Gly
            500                 505                 510

Gly Ala Ala Ala Ala Ala Ala Ala Ala Gly Gly Ala Gly Gln
        515                 520                 525

Gly Gly Tyr Gly Gly Tyr Gly Gln Gln Gly Gly Ala Gly Ala Ala Ala
            530                 535                 540

Ala Ala Ala Ser Gly Pro Gly Gln Ile Tyr Tyr Gly Pro Gln Ser Val
545                 550                 555                 560

Ala Ala Pro Ala Ala Ala Ala Ser Ala Leu Ala Ala Pro Ala Thr
                565                 570                 575

Ser Ala Arg Ile Ser Ser His Ala Ser Ala Leu Leu Ser Asn Gly Pro
                580                 585                 590

Thr Asn Pro Ala Ser Ile Ser Asn Val Ile Ser Asn Ala
                595                 600                 605

<210> SEQ ID NO 31
<211> LENGTH: 729
<212> TYPE: PRT
<213> ORGANISM: artificial
<220> FEATURE:
<223> OTHER INFORMATION: synthetic

<400> SEQUENCE: 31

Met Thr Trp Ser Thr Arg Leu Ala Leu Ser Phe Leu Phe Val Leu Cys
1               5                   10                  15

Thr Gln Ser Leu Tyr Ala Leu Ala Gln Ala Asn Thr Pro Trp Ser Ser
            20                  25                  30

Lys Ala Asn Ala Asp Ala Phe Ile Asn Ser Phe Ile Ser Ala Ala Ser
        35                  40                  45

Asn Thr Gly Ser Phe Ser Gln Asp Gln Met Glu Asp Met Ser Leu Ile
    50                  55                  60

Gly Asn Thr Leu Met Ala Ala Met Asp Asn Met Gly Gly Arg Ile Thr
65                  70                  75                  80

Pro Ser Lys Leu Gln Ala Leu Asp Met Ala Phe Ala Ser Ser Val Ala
                85                  90                  95

Glu Ile Ala Ala Ser Glu Gly Gly Asp Leu Gly Val Thr Thr Asn Ala
            100                 105                 110

Ile Ala Asp Ala Leu Thr Ser Ala Phe Tyr Gln Thr Thr Gly Val Val
        115                 120                 125

Asn Ser Arg Phe Ile Ser Glu Ile Arg Ser Leu Ile Gly Met Phe Ala
    130                 135                 140

Gln Ala Ser Ala Asn Asp Val Tyr Ala Ser Ala Gly Ser Ser Gly Gly
145                 150                 155                 160

Gly Gly Tyr Gly Ala Ser Ser Ala Ser Ala Ser Ala Ser Ala Ala
                165                 170                 175

Ala Pro Ser Gly Val Ala Tyr Gln Ala Pro Ala Gln Ala Gln Ile Ser
            180                 185                 190

Phe Thr Leu Arg Gly Gln Gln Pro Val Ser Tyr Gly Gln Gly Ala
        195                 200                 205

Gly Pro Gly Gly Ala Gly Ala Ala Ala Ala Ala Ala Ala Gly
    210                 215                 220

Gly Ala Gly Gln Gly Gly Gln Gly Gly Tyr Gly Gln Gly Gly Tyr Gly
225                 230                 235                 240
```

-continued

Gln Gly Gly Ala Gly Gln Gly Gly Ser Gly Ala Ala Ala Ala Gly
            245                 250                 255

Gly Thr Gly Gln Gly Gly Ala Gly Gln Gly Gly Ala Gly Ala Ala
            260                 265                 270

Ala Ala Ala Ala Ala Gly Gly Ala Gly Gln Gly Gly Gln Gly Gly
            275                 280                 285

Tyr Gly Gln Gly Gly Tyr Gly Gln Gly Gly Thr Gly Gln Gly Gly Ala
            290                 295                 300

Gly Ala Ala Ala Ala Ala Ala Ala Gly Ala Gly Gln Gly Gly
305                 310                 315                 320

Gln Gly Gly Tyr Gly Gln Gly Gly Tyr Gly Gln Gly Gly Ser Gly Ala
            325                 330                 335

Ala Ala Ala Ala Ala Ala Gly Gly Ala Gly Gln Gly Gly Gln
            340                 345                 350

Gly Gly Tyr Gly Gln Gly Gly Tyr Gly Gln Gly Gly Ala Gly Gln Gly
            355                 360                 365

Gly Ala Gly Ala Ala Ala Ala Ala Ala Ala Gly Gly Ala Gly
            370                 375                 380

Gln Gly Gly Tyr Gly Arg Gly Gly Ala Gly Gln Gly Gly Ala Ala Ala
385                 390                 395                 400

Ala Ala Ala Ala Ala Gly Ala Gly Gln Gly Gly Tyr Gly Gly Gln
            405                 410                 415

Gly Ala Gly Gly Ala Gly Ala Ala Ala Ala Ala Ala Gly Gly
            420                 425                 430

Ala Gly Gln Gly Gly Gln Gly Gly Tyr Gly Gln Gly Gly Tyr Gly Gln
            435                 440                 445

Gly Gly Ala Gly Gln Gly Gly Ala Ala Ala Ala Ala Ala Ala Gly
            450                 455                 460

Gly Ala Gly Gln Gly Gly Tyr Gly Arg Gly Gly Ala Gly Gln Gly Gly
465                 470                 475                 480

Ala Ala Ala Ala Ala Ala Ala Ala Gly Ala Gly Gln Gly Gly Tyr
            485                 490                 495

Gly Gly Gln Gly Ala Gly Gln Gly Gly Ala Gly Ala Ala Ala Ala
            500                 505                 510

Ala Ala Ala Gly Gly Ala Gly Gln Gly Gly Gln Gly Gly Tyr Gly Arg
            515                 520                 525

Gly Gly Tyr Asp Gln Gly Gly Ala Gly Gln Gly Gly Ala Gly Ala Ala
            530                 535                 540

Ala Ala Ala Ala Ala Ala Gly Gly Ala Gly Gln Gly Gly Gln Gly
545                 550                 555                 560

Gly Tyr Gly Gln Gly Gly Tyr Gly Gln Gly Gly Ala Gly Gln Gly Gly
            565                 570                 575

Ala Ala Ala Ala Ala Ala Ala Ala Gly Gly Ala Gly Gln Gly
            580                 585                 590

Gly Tyr Gly Gly Tyr Gly Gln Gln Gly Gly Ala Gly Ala Ala Ala Ala
            595                 600                 605

Ala Ala Ser Gly Pro Gly Gln Ile Tyr Tyr Gly Pro Gln Ser Val Ala
            610                 615                 620

Ala Pro Ala Ala Ala Ala Ser Ala Leu Ala Pro Ala Thr Ser
625                 630                 635                 640

Ala Arg Ile Ser Ser His Ala Ser Ala Leu Leu Ser Asn Gly Pro Thr
            645                 650                 655

Asn Pro Ala Ser Ile Ser Asn Val Ile Ser Asn Ala Val Ser Gln Ile

```
                        660                 665                 670
Ser Ser Ser Asn Pro Gly Ala Ser Ala Cys Asp Val Leu Val Gln Ala
                675                 680                 685

Leu Leu Glu Leu Val Thr Ala Leu Leu Thr Ile Ile Gly Ser Ser Asn
            690                 695                 700

Ile Gly Ser Val Asn Tyr Asp Ser Ser Gly Gln Tyr Ala Gln Val Val
705                 710                 715                 720

Thr Gln Ser Val Gln Asn Ala Phe Ala
                725

<210> SEQ ID NO 32
<211> LENGTH: 285
<212> TYPE: PRT
<213> ORGANISM: artificial
<220> FEATURE:
<223> OTHER INFORMATION: synthetic

<400> SEQUENCE: 32

Met Thr Trp Ser Thr Arg Leu Ala Leu Ser Phe Leu Leu Val Leu Cys
1               5                   10                  15

Thr Gln Ser Ile Tyr Ala Leu Ala Gln Ala Asn Thr Pro Trp Ser Ser
                20                  25                  30

Lys Ala Asn Ala Asp Ala Phe Ile Gly Ser Phe Ile Ser Ser Ala Gln
            35                  40                  45

Asn Thr Gly Ala Phe Ser Thr Asp Gln Met Asp Asp Met Ser Leu Ile
        50                  55                  60

Gly Asn Thr Leu Met Ala Ala Met Asp Asn Met Gly Gly Arg Ile Thr
65              70                  75                  80

Pro Ser Lys Leu Gln Ala Leu Asp Met Ala Phe Ala Ser Ser Val Ala
                85                  90                  95

Glu Ile Ala Ala Ala Glu Gly Gly Asp Leu Gly Val Thr Thr Asn Ala
            100                 105                 110

Ile Ala Asp Ala Leu Thr Ser Ala Phe Tyr Gln Thr Thr Gly Val Val
        115                 120                 125

Asn Ser Arg Phe Ile Ser Glu Ile Arg Ser Leu Ile Asn Met Phe Ala
130                 135                 140

Gln Ala Ser Ala Asn Asp Val Tyr Ala Ser Ala Gly Ser Ser Gly Gly
145                 150                 155                 160

Gly Gly Tyr Gly Ala Ala Ser Ser Ala Ser Ala Ala Ser Ser
                165                 170                 175

Ser Ala Ser Ala Ala Pro Ser Gly Val Ser Tyr Gln Ala Pro Ala
            180                 185                 190

Gln Ala Gln Ile Ser Phe Ser Leu Thr Arg Gln Gln Pro Val Asn
                195                 200                 205

Tyr Gly Gln Ser Gly Ala Ser Ala Ser Ala Ala Ala Gly Gly
        210                 215                 220

Ala Gly Gln Gly Gly Tyr Gly Gln Gly Gly Ala Gly Gln Gly Gly Ala
225                 230                 235                 240

Gly Ala Ala Ala Ala Ala Ala Ala Gly Gly Ala Gly Gln Gly Gly
            245                 250                 255

Gln Gly Gly Tyr Gly Gln Gly Gly Gly Gln Gly Gly Ala Ala Ala
                260                 265                 270

Ala Ala Ala Ala Ala Gly Gly Ala Gly Gln Gly Gly Gln
            275                 280                 285
```

```
<210> SEQ ID NO 33
<211> LENGTH: 22
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: X is A or G
<220> FEATURE:
<221> NAME/KEY: MISC_FEATURE
<222> LOCATION: (2)..(2)
<223> OTHER INFORMATION: X is SG or GG
<220> FEATURE:
<221> NAME/KEY: MISC_FEATURE
<222> LOCATION: (6)..(6)
<223> OTHER INFORMATION: X is GQ or absent
<220> FEATURE:
<221> NAME/KEY: MISC_FEATURE
<222> LOCATION: (11)..(11)
<223> OTHER INFORMATION: X is G or absent
<220> FEATURE:
<221> NAME/KEY: MISC_FEATURE
<222> LOCATION: (13)..(13)
<223> OTHER INFORMATION: X is G or S
<220> FEATURE:
<221> NAME/KEY: MISC_FEATURE
<222> LOCATION: (17)..(17)
<223> OTHER INFORMATION: X is SP or GR or absent

<400> SEQUENCE: 33

Xaa Xaa Ser Gly Pro Xaa Gly Gly Tyr Gly Xaa Pro Xaa Gln Gly Pro
1               5                   10                  15

Xaa Gly Gly Tyr Gly Pro
            20

<210> SEQ ID NO 34
<211> LENGTH: 6
<212> TYPE: PRT
<213> ORGANISM: Artificial
<220> FEATURE:
<223> OTHER INFORMATION: Synthetic peptide

<400> SEQUENCE: 34

Pro Gly Gly Tyr Gly Pro
1               5

<210> SEQ ID NO 35
<211> LENGTH: 36
<212> TYPE: PRT
<213> ORGANISM: Artificial
<220> FEATURE:
<223> OTHER INFORMATION: Synthetic peptide

<400> SEQUENCE: 35

Ser Gly Pro Gly Gly Tyr Gly Pro Gly Ser Gln Gly Pro Ser Gly Pro
1               5                   10                  15

Gly Gly Tyr Gly Pro Gly Gly Pro Gly Ser Ser Ala Gly Ala Gly Ala
            20                  25                  30

Gly Ala Ala Ala
        35

<210> SEQ ID NO 36
<211> LENGTH: 36
<212> TYPE: PRT
<213> ORGANISM: Artificial
<220> FEATURE:
<223> OTHER INFORMATION: Synthetic peptide
```

<400> SEQUENCE: 36

Ser Gly Pro Gly Gly Tyr Pro Gly Ser Gln Gly Pro Ser Gly Pro
1               5                   10                  15
Gly Gly Tyr Gly Pro Gly Pro Gly Ser Ser Ala Gly Ala Gly Ala
                20                  25                  30
Gly Ala Gly Ala
        35

<210> SEQ ID NO 37
<211> LENGTH: 29
<212> TYPE: PRT
<213> ORGANISM: Artificial
<220> FEATURE:
<223> OTHER INFORMATION: Synthetic peptide

<400> SEQUENCE: 37

Ser Gly Ser Gly Pro Gly Gly Tyr Gly Pro Gly Gly Gln Gly Pro Gly
1               5                   10                  15
Gly Tyr Gly Pro Gly Gly Gln Gly Pro Tyr Gly Pro Gly
                20                  25

<210> SEQ ID NO 38
<211> LENGTH: 36
<212> TYPE: PRT
<213> ORGANISM: Artificial
<220> FEATURE:
<223> OTHER INFORMATION: Synthetic peptide

<400> SEQUENCE: 38

Ser Gly Ser Gly Pro Gly Gly Tyr Gly Pro Gly Gly Gln Gly Pro Gly
1               5                   10                  15
Gly Tyr Gly Pro Gly Gly Gln Gly Pro Tyr Gly Pro Gly Ala Ala Ala
                20                  25                  30
Ala Ala Ala Ala
        35

<210> SEQ ID NO 39
<211> LENGTH: 29
<212> TYPE: PRT
<213> ORGANISM: Artificial
<220> FEATURE:
<223> OTHER INFORMATION: Synthetic peptide

<400> SEQUENCE: 39

Gly Gly Ser Gly Pro Gly Gly Tyr Gly Pro Gly Gly Gln Gly Pro Gly
1               5                   10                  15
Gly Tyr Gly Pro Gly Gly Gln Gly Pro Tyr Gly Pro Gly
                20                  25

<210> SEQ ID NO 40
<211> LENGTH: 36
<212> TYPE: PRT
<213> ORGANISM: Artificial
<220> FEATURE:
<223> OTHER INFORMATION: Synthetic pepide

<400> SEQUENCE: 40

Gly Gly Ser Gly Pro Gly Gly Tyr Gly Pro Gly Gly Gln Gly Pro Gly
1               5                   10                  15
Gly Tyr Gly Pro Gly Gly Gln Gly Pro Tyr Gly Pro Gly Ala Ala Ala
                20                  25                  30
Ala Ala Ala Ala

-continued

<210> SEQ ID NO 41
<211> LENGTH: 27
<212> TYPE: PRT
<213> ORGANISM: Artificial
<220> FEATURE:
<223> OTHER INFORMATION: Synthetic pepide

<400> SEQUENCE: 41

Ser Gly Pro Gly Gln Gly Gly Tyr Gly Gly Pro Gly Gly Gln Gly Pro
1               5                   10                  15

Gly Arg Gly Gly Tyr Gly Pro Gly Ala Gly Ser
            20                  25

<210> SEQ ID NO 42
<211> LENGTH: 36
<212> TYPE: PRT
<213> ORGANISM: Artificial
<220> FEATURE:
<223> OTHER INFORMATION: Synthetic pepide

<400> SEQUENCE: 42

Ser Gly Pro Gly Gln Gly Gly Tyr Gly Gly Pro Gly Gly Gln Gly Pro
1               5                   10                  15

Gly Arg Gly Gly Tyr Gly Pro Gly Ala Gly Ser Ala Ala Ala Ala
            20                  25                  30

Ala Ala Ala Ala
        35

<210> SEQ ID NO 43
<211> LENGTH: 37
<212> TYPE: PRT
<213> ORGANISM: Artificial
<220> FEATURE:
<223> OTHER INFORMATION: Synthetic pepide

<400> SEQUENCE: 43

Ala Arg Thr Ile Phe Ile Cys Ile Ala Leu Gly Gly Pro Gly Gln Gly
1               5                   10                  15

Gly Tyr Gly Gly Pro Gly Gly Gln Gly Pro Gly Arg Gly Gly Tyr Gly
            20                  25                  30

Pro Gly Ala Gly Ser
        35

<210> SEQ ID NO 44
<211> LENGTH: 27
<212> TYPE: PRT
<213> ORGANISM: Artificial
<220> FEATURE:
<223> OTHER INFORMATION: Synthetic peptide

<400> SEQUENCE: 44

Gly Gly Pro Gly Gln Gly Gly Tyr Gly Gly Pro Gly Gly Gln Gly Pro
1               5                   10                  15

Gly Arg Gly Gly Tyr Gly Pro Gly Ala Gly Ser
            20                  25

<210> SEQ ID NO 45
<211> LENGTH: 108
<212> TYPE: DNA
<213> ORGANISM: Artificial
<220> FEATURE:
<223> OTHER INFORMATION: Synthetic

```
<400> SEQUENCE: 45
tccggacccg gtggctacgg acctggttct cagggcccca gcggaccagg tggctacgga        60
cctggtggcc caggatcctc agctggtgcc ggcgctggtg ccgctgca                   108

<210> SEQ ID NO 46
<211> LENGTH: 108
<212> TYPE: DNA
<213> ORGANISM: Artificial
<220> FEATURE:
<223> OTHER INFORMATION: Synthetic

<400> SEQUENCE: 46
tccggttctg gccccggagg ttacggccct ggtggccagg gaccaggtgg ctacggaccg        60
ggtggccaag gacccctacgg tcctggcgct gccgctgccg cggctgca                  108

<210> SEQ ID NO 47
<211> LENGTH: 108
<212> TYPE: DNA
<213> ORGANISM: artificial
<220> FEATURE:
<223> OTHER INFORMATION: Synthetic

<400> SEQUENCE: 47
tccggtccag gccaaggagg ttacggcgga cctggtggcc agggaccogg tcgtggcgga        60 tacggtccgg gcgctggatc tgctgccgcg gcagctgccg cggctgca                   108
```

The invention claimed is:

1. A composition comprising a mixture of proteins comprising between 4 and 32 types of proteins of differing molecular weight, wherein each protein in said mixture comprises, independently, 2 to 70 repeats of a repetitive region of an ADF-4 protein, comprising an amino acid sequence as set forth in SEQ ID NO: 1

$(X_1)_ZX_2GPGGYGPX_3X_4X_5GPX_6GX_7GGX_8GP$
$GGPGX_9X_{10}$ wherein $X_1$ is, independently, at each instance A or G wherein at least 50% of $(X_1)_Z$ is A, Z is an integer between 5 to 30; $X_2$ is S or G; $X_3$ is G or E; $X_4$ is G, S or N; $X_5$ is Q or Y; $X_6$ is G or S; $X_7$ is P or R; $X_8$ is Y or Q; $X_9$ is G or S; and $X_{10}$ is S or G, wherein said mixture is characterized by molecular weight increment of 2 kDa to 3.5 kDa, between at least two proteins in said mixture.

2. The composition of claim 1, wherein each repeat has a molecular weight in the range of 2 kDa to 3.5 kDa.

3. The composition of claim 1, wherein said repetitive region has a first moiety and contiguous thereto a second moiety, the first moiety is an amino acid sequence of 5-30 amino acids comprising at least 50% alanine residues, the second moiety is an amino acid sequence of 20-60 amino acids comprising at least 80% residues selected from the group consisting of glycine, serine, proline and tyrosine, optionally wherein the second moiety comprises at most two glutamine residues.

4. The composition of claim 1, comprising a protein having the amino acid sequence as set forth in SEQ ID NO: 33

$(X_1)_ZX_2SGPX_3GGYGX_4PX_5QGPX_6GGYGP$ wherein $X_1$ is, independently, at each instance A or G wherein at least 50% of $(X_1)_Z$ is A, Z is an integer between 5 to 30; $X_2$ is S-G or absent; $X_3$ is G-Q or absent; $X_4$ is G or absent; $X_5$ is S or G; $X_6$ is S-P, G-R, or absent.

5. The composition of claim 1, wherein said repetitive region comprises the amino acid sequence selected from the group consisting of SEQ ID NO: 2 (SGPG-GYGPGSQGPSGPGGYGPGGPGSS) and SEQ ID NO: 3 (AAAAAAAASGPGGYGPGSQGPSGPG-GYGPGGPGSS).

6. The composition of claim 1, wherein each protein of said mixture further comprises a single N-terminal region selected from the group consisting of:

SEQ ID NO: 5 (MSYYHHHHHHDYDIPTTENLYFQGAMDPE-FKGLRRRAQLV),

SEQ ID NO: 6 (MSYYHHHHHHDYDIPTTENLYFQGAMDPE-FKGLRRRAQLVRPLSNLDNA),

SEQ ID NO: 7 MSYYHHHHHHDYDIPTTENLYFQGAMDPE-FKGLRRRAQLVDPPGCRNSARAGSS), and a sequence sharing at least 70% sequence identity with any one of SEQ ID NOs: 5-7.

7. The composition of claim 1, wherein each protein of said mixture further comprises a single C-terminal region as set forth in SEQ ID NO: 9 (GPSGPGAYGPSP-SASASVAASRLSSPAASSRVSSAVSSLVSSGPTN-GAAVSGALNSLVSQISASN PGLSGCDALVQAL-LELVSALVAILSSASIGQVNVSSVSQSTQMISQALS), or a sequence sharing at least 70% sequence identity with SEQ ID NO: 9.

8. The composition of claim 1, wherein any one of:
(i) one or more proteins of said mixture further comprises at least one tag sequence;

(ii) said mixture of proteins further comprises ADF-3 or MASP-2 proteins;
(iii) is characterized by a DSC pattern exhibiting at least an endothermic peak in the range of from 250° C. to 330° C., optionally wherein said DSC pattern further comprises an endothermic peak in the range of 220° C. to 250° C.;
(iv) further comprising a carrier, diluent or excipient; and
(v) any combination of (i)-(iv).

9. An article or a fiber comprising the composition of claim 1.

10. An isolated nucleic acid sequence encoding 4 to 32 proteins of differing molecular weight,
wherein each protein comprises, independently, 2 to 70 repeats of a repetitive region of an ADF-4 protein, comprising an amino acid sequence as set forth in SEQ ID NO: 1

$(X_1)ZX_2GPGGYGPX_3X_4X_5GPX_6GX_7GGX_8GPGGPGX_9X_{10}$ wherein $X_1$ is, independently, at each instance A or G wherein at least 50% of $(X_1)Z$ is A, Z is an integer between 5 to 30; $X_2$ is S or G; $X_3$ is G or E; $X_4$ is G, S or N; $X_5$ is Q or Y; $X_6$ is G or S; $X_7$ is P or R; $X_8$ is Y or Q; $X_9$ is G or S; and $X_{10}$ is S or G, wherein said proteins of differing molecular weight are characterized by molecular weight increment of 2 kDa to 3.5 kDa between at least two proteins.

11. An expression vector comprising the nucleic acid sequence of claim 10, wherein said nucleic acid sequence is under expression control of an operably linked promoter and, optionally, regulatory sequences.

12. A host cell transformed with the expression vector according to claim 11.

* * * * *